(12) United States Patent
Wilks et al.

(10) Patent No.: US 8,450,368 B2
(45) Date of Patent: May 28, 2013

(54) HEME OXYGENASE INHIBITORS, SCREENING METHODS FOR HEME OXYGENASE INHIBITORS AND METHODS OF USE OF HEME OXYGENASE INHIBITORS FOR ANTIMICROBIAL THERAPY

(75) Inventors: Angela Wilks, Baltimore, MD (US); Alexander MacKerrel, Jr., Baltimore, MD (US); Lena Furci, Grove City, OH (US); Pedro Lopes, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 869 days.

(21) Appl. No.: 12/374,964

(22) PCT Filed: Jul. 24, 2007

(86) PCT No.: PCT/US2007/074233
§ 371 (c)(1),
(2), (4) Date: Nov. 2, 2009

(87) PCT Pub. No.: WO2008/014266
PCT Pub. Date: Jan. 31, 2008

(65) Prior Publication Data
US 2010/0081661 A1    Apr. 1, 2010

Related U.S. Application Data

(60) Provisional application No. 60/945,710, filed on Jun. 22, 2007, provisional application No. 60/832,892, filed on Jul. 24, 2006.

(51) Int. Cl.
*A01N 37/10* (2006.01)
*A61K 31/19* (2006.01)

(52) U.S. Cl.
USPC ........................... 514/557; 514/568; 514/569

(58) Field of Classification Search
USPC ................................. 514/243, 557, 568, 569
See application file for complete search history.

(56) References Cited

U.S. PATENT DOCUMENTS

| | | | |
|---|---|---|---|
| 5,010,073 | A | 4/1991 | Kappas et al. |
| 5,217,997 | A | 6/1993 | Levere et al. |
| 5,595,753 | A | 1/1997 | Hechtman |
| 5,872,104 | A | 2/1999 | Vermeulen et al. |
| 6,066,333 | A | 5/2000 | Willis et al. |
| 6,066,628 | A | 5/2000 | Stojiljkovic et al. |
| 6,727,240 | B1 | 4/2004 | Neurath et al. |
| 7,026,488 | B2 | 4/2006 | Maeda et al. |
| 7,045,140 | B2 | 5/2006 | Motterlini et al. |
| 7,049,334 | B2 | 5/2006 | Fu et al. |
| 7,358,359 | B2 | 4/2008 | Andersen et al. |
| 2003/0225126 | A1 | 12/2003 | Markham et al. |
| 2004/0062721 | A1 * | 4/2004 | Montgomery .................. 424/46 |
| 2004/0110963 | A1 | 6/2004 | Burri et al. |
| 2004/0229955 | A1 | 11/2004 | Andersen et al. |
| 2005/0043369 | A1 | 2/2005 | Markham et al. |
| 2005/0136444 | A1 | 6/2005 | Scully et al. |
| 2007/0244197 | A1 | 10/2007 | Andersen et al. |
| 2008/0269221 | A1 | 10/2008 | Andersen et al. |
| 2009/0163496 | A1 | 6/2009 | Andersen et al. |
| 2009/0247506 | A1 | 10/2009 | Andersen et al. |

FOREIGN PATENT DOCUMENTS

| | | |
|---|---|---|
| WO | 96/20010 A1 | 7/1996 |
| WO | WO 01/16357 A2 * | 3/2001 |
| WO | 01/70213 A2 | 9/2001 |
| WO | 02/070464 A2 | 9/2002 |
| WO | 03/078386 A1 | 9/2003 |
| WO | 2004/062601 A2 | 7/2004 |

OTHER PUBLICATIONS

Communication with Supplementary European Search Report dated Nov. 25, 2009, issued in corresponding European Patent Application No. 07840495.1.
Sahoo, S. K. et al; "Pegylated Zinc Protoporphyrin: A Water-Soluble Heme Oxygenase Inhibitor with Tumour-Targeting Capacity"; Bioconjugate Chemistry, 2002, vol. 13, No. 5, pp. 1031-1038.
De La Fuente, R. et al: "Small molecules with antimicrobial activity against *E. coli* and *P. aeruginose* identified by high-throughput screening" British Journal of Pharmacolohy, 2006, vol. 149, 551-559.
Vilahakis, Jason Z. et al.; Imidazole-Dioxolane Compounds as Isozyme-Selective Heme Oxygenase Inhibitors; Journal of Medicinal Chemistry, Jul. 13, 2006, vol. 49, No. 14, pp. 4437-4441.
Office Action issued on Mar. 30, 2010 in corresponding European Patent Application 07840495.1-2123.
Office Action issued on Sep. 1, 2010 in corresponding Canadian Patent Application 2,658,877.
Office Action issued on Jan. 27, 2011 in corresponding European Patent Application 07840495.1-2123.
Office Action issued May 4, 2011 in corresponding Canadian Patent Application 2,658,877.
Office Action issued Dec. 14, 2011 in corresponding Canadian Patent Application 2,658,877.
Lena M Furci et al., "Inhibition of the Bacterial Heme Oxygenases from *Pseudomonas aeruginosa* and *Neisseria meningitidis*: Novel Antimicrobial Targets", American Chemical Society, 2007, J. Med Chem 50,3804-3813, 2007.
Form PCT/ISA/210 "International Search Report", dated Sep. 16, 2008.
Form PCT/ISA/237 "Written Opinion of the International Searching Authority", dated Sep. 16, 2008.
Australia Office Action dated Feb. 8, 2010, issued in corresponding Australia Patent Application No. 2007276763.

* cited by examiner

*Primary Examiner* — Yong Chong
(74) *Attorney, Agent, or Firm* — Westerman, Hattori, Daniels & Adrian, LLP

(57) ABSTRACT

Inhibitors of microbial heme oxygenase and their use for treatment of microbial infections and bioremediation. The inhibitors of microbial heme oxygenase are useful against a new class of antimicrobial agents to target infections that are persistently difficult to combat with the current spectrum of antimicrobial agents. Screening methods for selecting inhibitors of microbial heme oxygenase.

5 Claims, 7 Drawing Sheets

1          2 apo-HO          holo-HO

HEME OXYGENASE INHIBITORS, SCREENING METHODS FOR HEME OXYGENASE INHIBITORS AND METHODS OF USE OF HEME OXYGENASE INHIBITORS FOR ANTIMICROBIAL THERAPY

STATEMENT REGARDING FEDERALLY SPONSORED RESEARCH OR DEVELOPMENT

This invention was made with the support of the U.S. government under Grant Number AI055912 from the National Institute of Health (NIH). The U.S. government has certain rights in this invention.

CROSS REFERENCE TO RELATED APPLICATIONS

This application is a National Stage of International Application No. PCT/US07/074,233, filed Jul. 24, 2007 which claims the benefit of U.S. Provisional Application No. 60/945,710, filed Jun. 22, 2007, and U.S. Provisional Application No. 60/832,892, filed Jul. 24, 2006, both of which are hereby incorporated by reference.

NAMES OF PARTIES OF A JOINT RESEARCH AGREEMENT

Not Applicable

INCORPORATION BY REFERENCE OF MATERIAL SUBMITTED ON A COMPACT DISC

Not Applicable

FIELD OF THE INVENTION

The present invention is directed to fields of chemistry and medicine. More specifically, the present invention is directed to the inhibition of heme utilization in pathogenic microbes as a target for antimicrobial therapy and compounds having such biological activity.

BACKGROUND OF THE INVENTION

Since antibiotics and other antimicrobial drugs first became widely used in the World War II era, they have saved countless lives and blunted serious complications of many feared diseases and infections. The success of antimicrobials against disease-causing microbes is among modern medicine's great achievements. After more than 50 years of widespread use, however, many antimicrobials are not as effective as they used to be.

Over time, some bacteria have developed ways to circumvent the effects of antibiotics. Widespread use of antibiotics is thought to have spurred evolutionarily adaptations that enable bacteria to survive these powerful drugs. Other microbes such as viruses, fungi, and parasites have developed resistance as well. Antimicrobial resistance provides a survival benefit to microbes and makes it harder to eliminate infections from the body. Ultimately, the increasing difficulty in fighting off microbes leads to an increased risk of acquiring infections in a hospital or other setting.

Diseases such as tuberculosis, gonorrhea, malaria, and childhood ear infections are now more difficult to treat than they were just a few decades ago. Drug resistance is an especially difficult problem for hospitals harboring critically ill patients who are less able to fight off infections without the help of antibiotics. Heavy use of antibiotics in these patients selects for changes in bacteria that bring about drug resistance. Unfortunately, this worsens the problem by producing bacteria with greater ability to survive even in the presence of our strongest antibiotics. These even stronger drug-resistant bacteria continue to prey on vulnerable hospital patients.

According to CDC statistics:
* Nearly 2 million patients in the United States get an infection in the hospital each year;
* About 90,000 of those patients die each year as a result of their infection, up from 13,300 patient deaths in 1992;
* More than 70 percent of the bacteria that cause hospital-acquired infections are resistant to at least one of the antibiotics most commonly used to treat them; and
* People infected with antibiotic-resistant organisms are more likely to have longer hospital stays and require treatment with second- or third-choice medicines that may be less effective, more toxic, and more expensive.

In short, antimicrobial resistance is driving up health care costs, increasing the severity of disease, and increasing the death rates from certain infections. Therefore, there is a long-felt need in the art for new antimicrobial therapies and particularly therapies that target alternative mechanisms of action.

The need to develop new antimicrobials, as well as new potential drug targets, is especially acute in the case of *P. aeruginosa* infections in CF patients, where the natural antibiotic resistance of the organism and the ability to form biofilms (bacteria encapsulated in a polymeric matrix) accounts for significant mortality in such patients[1-3]. The inhibitors of the present invention provide a new class of antimicrobial agents to target infections that are persistently difficult to combat with the current spectrum of antimicrobial agents. *P. aeruginosa* is one example of a bacteria that is resistant to many antibiotics and has acquired resistance to others and is classified as having broad spectrum resistance. Most recently reports on the epidemiology of bactermia in early bone marrow transplant patients indicated numerous multi-drug resistant (MDR) gram negative strains, defined as an isolate with resistance to at least two of the following: third- or fourth-generation cephalosporins, carbapenems or piperacillin-tazobactam. Of 411 transplant recipients fever occurred in 333, and 91 developed bacteremia (118 isolates): 47% owing to Gram-positive, 37% owing to Gram-negative, and 16% caused by Gram-positive and Gram-negative bacteria. *Pseudomonas aeruginosa* (22%), *Klebsiella pneumoniae* (19%) and *Escherichia coli* (17%) accounted for the majority of Gram-negative isolates, and 37% were MDR[4].

The final step in heme utilization and iron acquisition in many pathogens is the oxidative cleavage of heme by heme oxygenase (HO), yielding iron, biliverdin and carbon monoxide. The present invention is based on iron being an essential requirement and HO being a therapeutic target for antimicrobial drug development.

BRIEF SUMMARY OF THE INVENTION

The present invention is directed to compositions and methods of use in treating an indication directly or indirectly related and/or caused by an organism, wherein the organism requires heme oxygenase (HO) to cleave heme yielding iron, biliverdin and carbon monoxide.

In certain embodiments, the compositions of the present invention are employed to treat infectious disease. In another embodiment, the compounds of the present invention are employed to purify and/or sanitize water sources, including natural and man-made sources. In yet another embodiment, the compositions of the present invention are employed to reduce, minimize, ameliorate the adverse impact of an undesired organism requiring heme oxygenase (HO) to cleave heme yielding iron, biliverdin and carbon monoxide on the environment.

Further the present invention is directed to a new antimicrobial class with broad-spectrum activity. The compositions and methods of use of the present invention provide an alternative to the current antimicrobials. Further, they may be used against microbes that have developed resistance profiles to the current antimicrobial drug classes and therapy.

These molecules inhibit the ability of the organism to obtain iron, a necessary requirement for survival and virulence. The inhibition of heme utilization is contemplated as a therapeutic target or as a bioremediation means.

The present invention is further directed to molecules identified in computer aided drug design (CADD) screening as inhibitors of an enzyme required for heme utilization by microbial pathogens and a method of screening for inhibitors of an enzyme in heme utilization by microbial pathogens. The enzyme is heme oxygenase (HO) or heme-chaperone.

As used herein, the term "heme utilization" refers to transfer of hemoglobin to a heme oxygenase, including the binding of heme to either a heme-chaperone or the heme oxygenase in a host microbial cell. The microbial may be fungal, viral, prion, protist or bacterial. In an exemplary embodiment, the PhuS protein of *P. aeruginosa* is the heme-chaperone and permits transfer of at least one heme molecule from PhuS to a pa-HO (heme oxygenase of *P. aeruginosa*).

Also contemplated herein is the administration of compounds that inhibit heme utilization as a pharmaceutical composition. The administration includes to a cell, a tissue, an organ and/or an animal. The compound may be administered externally, orally, systemically, intranasally, intravenously and/or subcutaneously or a combination thereof. Embodiments of administration include a tablet, a pill, a powder for suspension in aqueous solution, a powder for dissolution in aqueous solution, a topical preparation further comprising an oil, a wax, a gel, a cream, an emulsion, and a sterile solution for injection.

The compounds of the present invention may be used in combination with other agents, such as antimicrobials, e.g., with other known antibiotic agents; chemotherapeutics, radionuclides and/or immunosuppressants, e.g. to treat a microbial infection in a patient having a suppressed immune system (immunocompromised) either as a consequence of receiving a separate treatment such as chemotherapy, radiation, antiviral regiment, and the like or as a consequence of having another condition non-related to hosting an organism requiring HO (such as, but not limited to, elderly, post-surgery, stress, etc). It is not necessary but the use in a combination therapy may have a synergistic affect. The combination therapy methods of the present invention are contemplated to be administered at a separate or the same time to a subject in need thereof.

The animal contemplated includes birds, reptiles, fish, mammals, including companion, domestic and food-producing animals. The mammal may be a human.

Also contemplated herein is the use of compounds that inhibit heme utilization as bioremediation. The present invention can be used in areas where microbials may be encountered. For example, in environmental products and uses, the treatment of microbials in water (e.g. water purification, drinking water, ground water, waste water, sewage or treatment facility ponds, and cooling tower water supplies), water sources at risk or plagued with microbial contamination or colonization, soil (e.g. contaminated soil, landfills, sediments, etc.), air, germ warfare, environmental control and pollution detection to name a few.

The compositions of the present invention may be used in materials, such as on, in or impregnating materials. For example, plastics, tubing, medical devices (e.g. surgical instruments, teeth, prosthetics, medical tubing, etc), food preparation and safety areas, air filtration media and supply materials, countertops, and generally surfaces in which microbial-free environment is desired or required.

The compositions of the present invention may be used in the treatment of food-producing animals, companion animals, and in all pet and veterinary uses in which a desire to ameliorate any adverse impact of organisms requiring heme oxygenase (HO) to cleave heme yielding iron, biliverdin and carbon monoxide on said animals.

The microbes contemplated include viruses, fungi, yeast, molds, parasites, bacteria, including eubacteria and archaea, or any pathogenic microbe. The microbe may be a Gram-negative bacteria. The microbe may be *Psudomonas, Yersinia, Shigella, Staphylococcus, Aspergillus, Candida, Streptococci* (i.e., *S. pneumoniae*), *Legionella* (i.e., *L. pneumophila L. micdadei*), *Vibrio, Escherichia, Mycobacterium, Salmonella* (i.e., *S. Typhi*), *Haemophilus* (i.e. *H. influenzae*), *Shigella Klebsiella, Enterobacter* sp, *Proteus* sp, and the like. In other embodiments, the microbe is a Gram-negative bacteria, such as, but not limited to *Klebsiella, Pseudomonas aeruginosa, Enterobacter* sp, *Proteus* sp, and *Escherichia coli*. Alternatively, the microbe is a Gram-positive bacteria and the skilled artisan is aware of well-known methods to determine if a bacteria is Gram-positive or Gram-negative as well as well-known methods of classifying and/or characterizing any bacteria (see, for example, Baron, Samuel (1996). Medical Microbiology, $4^{th}$ ed, The University of Texas Medical Branch at Galveston; Madigan M., Martinko, J. (editors), (2005), Brock Biology of Microorganisms, $11^{th}$ ed, Prentice Hall). The present invention is advantageously used and particularly suited for a microbe having resistance to one or more antimicrobial therapies.

The compositions of the present invention may be used externally and/or topically in any instance in which minimization, reduction or ameoliration of the adverse impact of an organism requiring heme oxygenase (HO) to cleave heme yielding iron, biliverdin and carbon monoxide is desired, such as a hand wash or sterilizer and for treatment of wounds, etc. The compositions of the present invention may be used in wash or disinfectant materials, single use materials, e.g., as wipes and towelettes.

The compositions of the present invention may be used in treating conditions associated with inflammation. The compositions of the present invention may be used inflammation in the central nervous system (CNS).

The compositions of the present invention may be used in treating conditions cancers that have a microbial origin, such as a viral origin.

The compositions of the present invention may be used in treating infection in the central nervous system, for example, spinal menigitis.

The compositions of the present invention may be used in treating *Mycobacterium* infection, for example *Mycobacterium tuberculosis* (tuberculosis), treating sepsis, treating Methicillin-resistant *Staphylococcus aureus* (MRSA), Nosocomial infections (e.g. *Enterococcus* spp., *Escherichia coli, Pseudomonas* spp., *Staphylococcus aureus*, urinary tract, surgical wounds, respiratory tract, skin (especially burns), blood (bacteremia), gastrointestinal tract, and central nervous system), and malaria (e.g., *Plasmodium falciparum, P. vivax, P. ovale* and *P. malariae*).

The methods of the present invention may be carried out in vitro, in vivo, in situ, ex vivo, and/or in utero.

In one embodiment, the methods of the present invention include contacting a cell with a heme utilization-inhibiting amount of a compound, wherein the cell comprises a heme chaperone and a heme oxygenase.

In one embodiment, the methods of the present invention are directed to inhibition of heme utilization in a microbial cell which includes disruption, either partially or completely, of the transfer of heme in situ from a heme chaperone to a heme oxygenase. Alternatively, the inhibition can include the disruption, either partially or completely, of attaching heme in situ to either the chaperone or the oxygenase.

In an exemplary embodiment, the method is directed to contacting a cell with a heme utilization-inhibiting amount of a compound wherein the compound disrupts at least one of (i) heme transfer from PhuS to pa-HO; (ii) heme binding to PhuS; or (iii) heme binding to pa-HO, wherein the cell is *P. aeruginosa*.

In other embodiments, the compounds and methods of the present invention are directed to administering to the pulmonary cavity of a mammal to treat the mammal for a microbial infection in a lung. This treatment may be desirable in cases in which the mammal has an existing disease or disorder, such as cystic fibrosis.

The ability of bacterial pathogens to acquire iron is essential for both their survival and infectivity. In order to acquire iron, bacteria have evolved specialized systems to directly utilize iron from the host's iron and heme containing proteins[5-9]. In a significant number of bacterial pathogens, the final step in heme utilization is the heme oxygenase (HO)-dependent oxidative cleavage of the porphyrin macrocycle to biliverdin and carbon monoxide with the release of iron[10,11]. Accordingly, due to the step in iron-utilization from heme, the bacterial HO's provide a unique therapeutic antimicrobial target.

A variety of gram-negative pathogens, including those that cause many endemic and life threatening diseases such as *Neisseria meningitidis*[12] and *Haemophilus influenzae*[13], the causative agents of some forms of meningitis, and enteric pathogens such as *Vibrio cholerae*[14, 15] and *Shigella dysenteriae*[16, 17], have evolved sophisticated mechanisms of iron acquisition that involve direct utilization of heme-containing proteins. *Neisseria meningitides*, an obligate human pathogen, is usually restricted to the nasopharynx but can invade the bloodstream and cause infections in the meninges and occasionally the synovial membranes of joints[18]. Although little is known on the bioavailability of heme on human mucosal surfaces, *Neisseria* spp. show phase-variation in the type of iron and heme-receptors expressed in response to physiological and environmental conditions[19]. This allows the bacteria to establish infections in environments where the heme availability may be extremely low through a combination of hemolysis and high-affinity outer-membrane heme-receptors which internalize the heme.

Heme uptake and utilization is also employed by opportunistic pathogens such as *Pseudomonas aeruginosa*, which has multiple systems for iron-uptake, including two Fur-regulated heme uptake operons[20]. *P. aeruginosa* has become an increasing cause of nosocomial infections in immune compromised patients, and is the primary cause of chronic lung infections in individuals with cystic fibrosis (CF) disease[1, 3]. In CF patients the virulence of *P. aeruginosa* is heightened by its ability to form biofilms[21-24] leading to antibiotic resistance profiles due to the inability to effectively eliminate the infective agent from such biofilms[23]. Approximately 40% of CF patients succumb to fatal infection due to antibiotic resistant *P. aeruginosa* infections[1]. Notably, a knockout of the heme oxygenase gene in *P. aeruginosa* (pigA:gen) develops heme toxicity when heme is the sole iron source[25], suggesting that inhibiting pa-HO in vivo will result in toxicity and ultimately decreased virulence of the pathogen.

An important consideration in the design of a novel therapeutic is its specificity for the target protein. In the present case this consideration is in the context of the bacterial versus the human forms of heme oxygenase. Comparison of heme oxygenase from *N. meningitidis* (nm-HO) with the mammalian enzymes shows the solvent accessible surface to be significantly smaller in both nm-HO and pa-HO, ~7.5 $Å^3$, when compared to their mammalian counterparts, which range from 43.6 to 59.7 $Å^3$ [26-29]. Such a structural difference suggests that low-molecular weight inhibitors of nm-HO can be identified that are specific for the bacterial over the human protein, and thus may act as antimicrobial compounds.

A second consideration in development of an antibiotic is its spectrum of activity. While the majority of heme oxygenases have a regioselectivity for the α-meso carbon, which is released as CO to yield δ-biliverdin, the iron-regulated heme oxygenase of *P. aeruginosa* (pa-HO) is regioselective for the δ-meso carbon[25]. However, pa-HO shares 33% identity with nm-HO while both bacterial HO's have less than 15% homology with the mammalian enzymes, increasing the probability of identifying inhibitors specific for the bacterial enzymes. The present invention includes the development of novel antibiotics targeting nm-HO that may be specific for other pathogens while having the necessary specificity for bacterial over mammalian HOs.

A further consideration in exploiting HO inhibition as the basis for antibiotic development is the presence of siderophores secreted by many gram-negative pathogens. Siderophores are high-affinity iron chelating complexes that sequester iron and actively transport the ferri-siderophore complex into the cell via a specific outer-membrane receptor[30]. However, the availability of iron for microbial assimilation within the human host is extremely limited with the majority of iron sequestered in hemoglobin and other hemeproteins (e.g. over 95.5%). Therefore, despite the presence of alternate mechanisms for iron uptake, during infection blocking heme utilization has the potential to decrease the virulence of *N. meninigitidis* and *P. aeruginosa*, as well as other gram negative bacteria.

The present application includes the use of CADD combined with experimental analysis to identify novel inhibitors of the bacterial heme oxygenases. The inhibitors of the bacterial heme oxygenases can cross the cell membrane and specifically inhibit the growth of organisms, for example, *N. meningitidis* and *P. aeruginosa*.

Discovery of novel inhibitors for a target protein can be greatly facilitated by the use of computer-aided drug design (CADD). In particular, Applicants used a virtual database screening approach to identify novel chemical entities with a high probability of binding to a target protein. Other studies have used CADD[31, 32 33-35]. The present invention includes using CADD with 3D structural information on the target protein, information for a number of heme oxygenases, including those of the human as well as the *N. meningitidis, C. diphtheriae* and *P. aeruginosa* bacterial enzymes. In the present invention, by using the 3D crystal structure of HO combined with CADD approaches and experimental assays Applicants have identified novel inhibitors of HO. For example, by using the 3D crystal structure of nm-HO combined with CADD approaches Applicants have identified novel inhibitors of nm-HO. In addition, these compounds also inhibit the heme oxygenase from the opportunistic pathogen *P. aeruginosa*, indicating their potential for development into novel broad spectrum antibiotics.

DETAILED DESCRIPTION OF THE INVENTION

Figure 1:
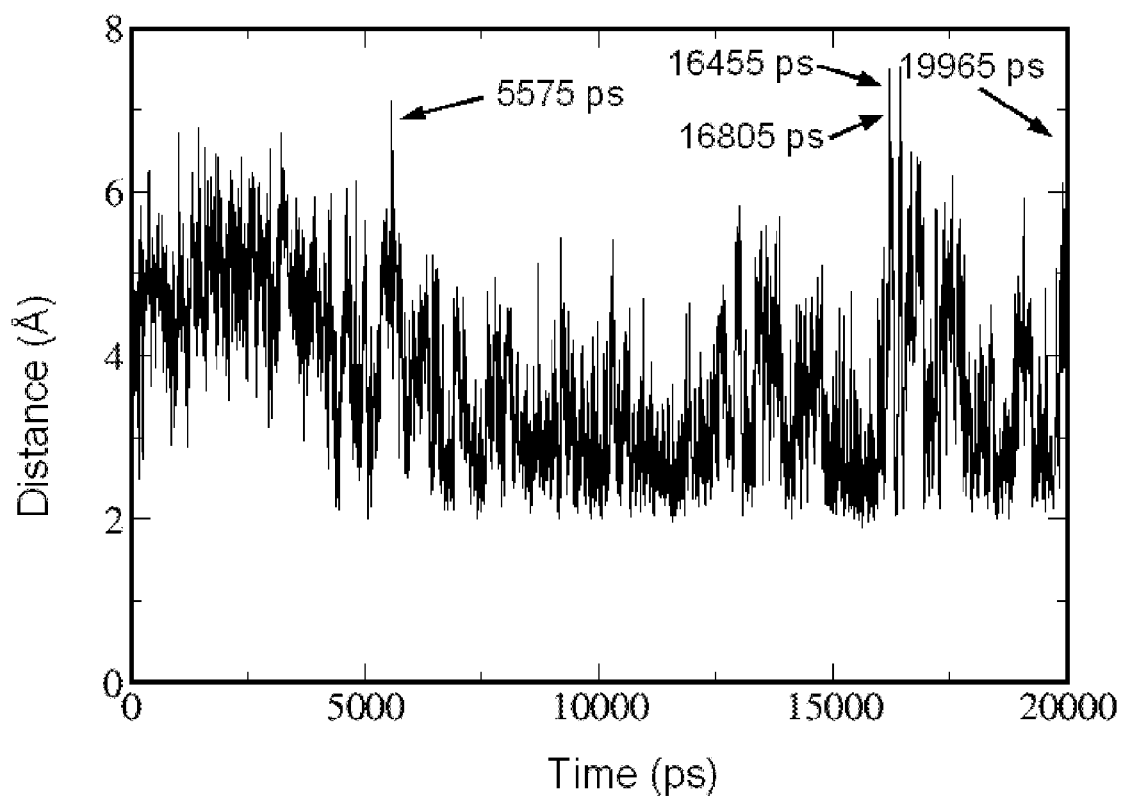
FIG. 1. Distance between His-23 and Gly-116 as a function of time from the MD simulation of apo-nm-HO. Snapshots with the largest separations were selected for the docking procedures and are indicated by arrows.

As used herein, "treat" means alter, apply, effect, improve, care for or deal with medically or surgically, ameliorate, cure, and or stop an undesired biological (pathogenic) process. The skilled artisan is aware that a treatment may or may not cure.

As used herein, the effective amount or "therapeutically effective amounts" of the compound of the present invention to be used are those amounts effective to produce beneficial results, particularly with respect to antimicrobial treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

A therapeutically effective amount of a compound of the present invention as a treatment varies depending upon the host treated and the particular mode of administration. In one embodiment of the invention as it applies to administering to a subject in need thereof, the dose range will be about 0.5 mg/kg body weight to about 500 mg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 1 mg/kg body weight to 450 mg/kg body weight, 2 mg/kg body weight to 400 mg/kg body weight, 3 mg/kg body weight to 350 mg/kg body weight, 4 mg/kg body weight to 300 mg/kg body weight, 5 mg/kg body weight to 250 mg/kg body weight, 6 mg/kg body weight to 200 mg/kg body weight, 7 mg/kg body weight to 150 mg/kg body weight, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for compound of the present invention.

Results

Database Screening.

In silico database screening was performed to identify low molecular weight compounds with a high probability of binding to the heme pocket of nm-HO. To initiate this process it was necessary to obtain conformations of the apo form of nm-HO (i.e. heme not bound) in which the heme binding pocket was in an "open" or accessible state. These were obtained via a molecular dynamics (MD) simulation of the apo protein from the crystal structure of nm-HO[29] (as outlined in the Experimental Section below). To identify such conformations the accessibility of the heme binding pocket was monitored by following the His-23 to Gly-116 distance as a function of time (FIG. 1). From this plot it is evident that more accessible conformations of the binding pocket are sampled at the 5,575, 16,455, 16,805 and 19,965 ps snapshots. Accordingly, these four conformations of nm-HO were selected for the database screening calculations.

As an example of a screening method of the present application, a primary screening of an 800,000 compound database of low molecular weight compounds (compounds with molecular weight less than 500 Da) that have drug like characteristics was performed using a single conformation; the 5,575 ps structure from the MD simulation. The top 50,000 compounds were selected from the primary screen based on the N normalized van der Waals (vdW) attraction interaction energy. The normalization procedure corrects for the tendency of scoring based on interaction energies to bias towards the selection of higher MW species[36] and use of the vdW attractive energy selects compounds that have good steric overlap with the protein and avoiding compounds that have very favorable electrostatics but do not have shape complimentarity with the binding pocket. The selection procedure yielded a distribution with an average MW of 279±77 Daltons; a value that is ideal for studies in which lead compounds are to be identified[37]. The selection of smaller MW compounds may facilitate lead optimization of the active compounds, a process that tends to lead to the increase of the molecular weight during the optimization process. In addition, by increasing the number of low molecular weight compounds selected, the absorption and disposition properties of the selected compounds may be improved[38,39].

The 50,000 compounds from the primary screen were then subjected to a secondary screen. In this screen conformational flexibility of the protein is partially taken into account by screening the 50,000 compounds against four protein conformations. Moreover, additional energy minimization is included during the secondary docking to improve the accuracy of the docked poses and scores from the initial screen. As compounds dominated by favorable electrostatics were excluded in the primary screen, scoring for the secondary screen was performed using the total interaction energy along with $N^{3/5}$ normalization to obtain a desirable MW distribution[36]. From this process the top 1000 compounds were selected.

Compounds selected from the DOCK based database screening may be assumed to all structurally complement the target binding site and, thus, have the potential to bind to the protein. It is desirable to select compounds from the top 1000 that have maximal chemical diversity, an approach that has been used successfully by us in previous studies[40,41]. Obtaining diverse compounds was performed via similarity clustering based on chemical fingerprints. This process lead to approximately 100 clusters following which one or two compounds were selected from each cluster for biological assay. This selection process emphasized identifying compounds that followed Lipinski's rule of 5, although in cases where all compounds in a cluster did not meet the criteria, a compound was still selected for assay. From this process a total of 153 compounds were selected and then obtained from commercial vendors. Table 2 lists the structural formulae, the vendor identification no., the MW, a10, d5 and Log P for the 153 Compounds. Table 2 also lists the fluorescence binding, minimum inhibition concentration, NMR sta. transfer, *E. coli* assay and *C. elegans* assay for some of the compounds. Initial experimental screening of those 153 compounds showed 37 to be soluble in either buffer or DMSO; these compounds were subjected to further experimental studies.

The compounds of the present invention also include pharmaceutically acceptable salts, esters, solvates, analogs, derivatives, prodrugs, isomers and hydrates thereof.

Tables 3A-6 below show data for selected compounds.

TABLE 3A

Analysis of compounds from the 1-153 identified in the initial screen and chemical diversity analysis.

Figure 2:
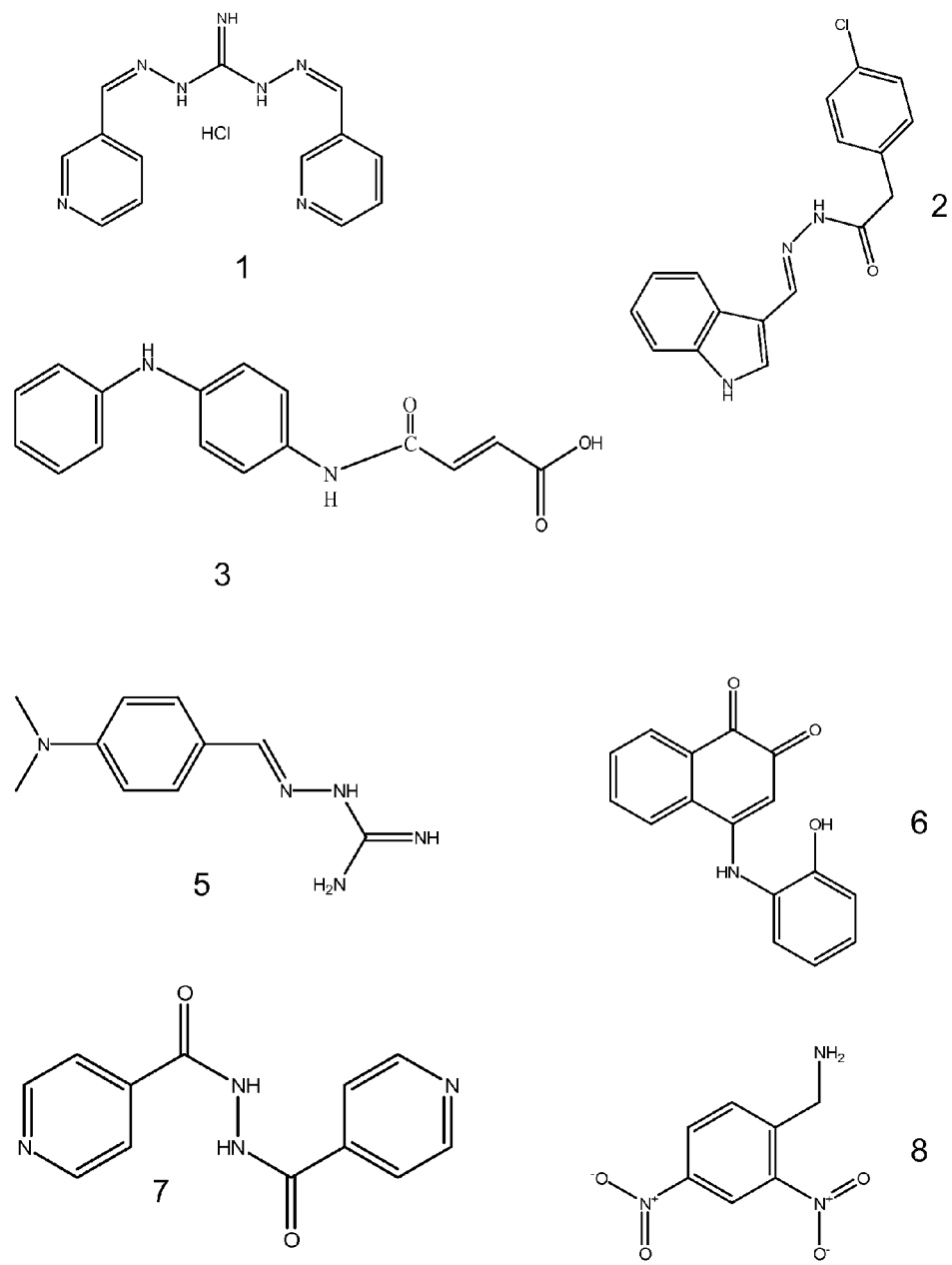
FIG. 2. Chemical Structures of the active inhibitors Compounds 1-8.

| No in master list | Alias | Compound ID | Fluorescence nm-HO Kd (uM) | Fluorescence pa-HO Kd (uM) | NMR pa-HO | Biliverdin detection from *E. coli* Assay | MIC 50 (ug/ml) | *C. elegans* | No. in FIG. 2 |
|---|---|---|---|---|---|---|---|---|---|
| 1 | CB-5 | 5173151 | 22.9 +/− 2.88 | 30.05 +/− 1.81 | + | White pellet | >160 | prolong life in infected worms | 5 |
| 75 | CB-7 | 5191821 | 15.6 +/− 1.94 | 20.10 +/− 1.80 | Nd | White pellet | >1000 | no effect | 3 |
| 126 | CB-18 | 5474974 | 14.1 +/− 2.60 | 15.79 +/− 0.98 | Nd | White pellet | no antibact activity | — | 2 |
| 148 | CB-31 | 5928257 | 12.2 +/− 0.99 | 15.87 +/− 1.07 | Nd | White pellet | no antibact activity | — | 1 |
| 22 | CB-35 | 6141274 | 20.9 +/− 4.56 | 6.09 +/− 0.54 | Nd | White pellet | >380 | no effect | 4 |
| 44 | CD-22 | 8003-8606 | 12.3 +/− 1.58 | nd | Ambig | nd | nd | — | |
| 114 | MayB6 | BTB 13061 | 28.8 +/− 3.26 | nd | Nd | Toxic | nd | — | 6 |
| 13 | Spec1 | AF-628/30886065 | 238.7 +/− 20.88 | nd | Nd | Toxic | nd | — | 8 |
| 133 | CB-9 | 5242836 | nd | nd | Nd | Green Pellet | >380 | — | |
| 8 | CB-38 | 6633579 | nd | nd | Nd | Green Pellet | >750 | — | |
| 24 | CD-18 | K781-2231 | 33.5 +/− 4.08 | nd | Nd | Green Pellet | nd | — | 7 |
| 150 | CD-2 | 0139-0251 | nd | nd | + | nd | no antibact activity | — | |
| 107 | CD-10 | 2825-0171 | nd | nd | + | nd | no antibact activity | — | |
| 59 | CD-12 | 4696-0935 | nd | nd | + | nd | >1000 | — | |
| 131 | CD-14 | 8010-0630 | nd | nd | + | nd | >250 | — | |
| 85 | SpecA | AK-968/37055109 | nd | nd | + | nd | no antibact activity | — | |
| 103 | SpecC | AI-942/25034862 | nd | nd | + | nd | >250 | — | |
| 152 | SpecD | AB-323/13887454 | nd | nd | + | nd | no antibact activity | — | |
| not in the list | SpecE | AC-364/37357066 | nd | nd | + | nd | no antibact activity | — | |

TABLE 3A-continued

Analysis of compounds from the 1-153 identified in the initial screen and chemical diversity analysis.

| No in master list | Alias | Compound ID | Fluorescence nm-HO Kd (uM) | Fluorescence pa-HO Kd (uM) | NMR pa-HO | Biliverdin detection from E. coli Assay | MIC 50 (ug/ml) | C. elegans | No. in FIG. 2 |
|---|---|---|---|---|---|---|---|---|---|
| 115 | SpecG | AE-641/13303057 | nd | nd | + | nd | no antibact activity | — | — |
| 87 | SpecH | AF-399/40768858 | nd | nd | + | nd | >125 | Inconclusive | — |
| 127 | SpecJ | AM-814/41093338 | nd | nd | + | nd | >1000 | — | — |
| 101 | CB-6 | 5173235 | nd | nd | + | nd | no antibact activity | — | — |
| 36 | CB-21 | 5509623 | nd | nd | + | nd | no antibact activity | — | — |
| 83 | CB-29 | 5881261 | nd | nd | + | nd | no antibact activity | — | — |
| 61 | CB-32 | 5940661 | nd | nd | + | nd | no antibact activity | — | — |

Shows binding by NMR method = +
nd = not determined
Ambig = ambiguous

TABLE 3B

Select compounds MIC50's for P. aeruginosa and inhibition of nm-HO activity in an E. coli expression system.

| Compound ID | | Biliverdin detection from E. coli Assay | MIC 50 (ug/ml) |
|---|---|---|---|
| CB-5 | 5173151 | White pellet | >160 |
| CB-7 | 5191821 | White pellet | >1000 |
| CB-18 | 5474974 | White pellet | >1000 |
| CB-31 | 5928257 | White pellet | >1000 |
| CB-35 | 6141274 | White pellet | >380 |
| CB-9 | 5242836 | Green Pellet | >380 |
| CB-38 | 6633579 | Green Pellet | >750 |
| ChemDiv 18 | K781-2231 | Green Pellet | nd |
| MayB6 | BTB 13061 | Toxic | nd |
| Spec1 | AF-628/30886065 | Toxic | nd |
| ChemDiv2 | 0139-0251 | nd | >1000 |
| ChemDiv10 | 2825-0171 | nd | >1000 |
| ChemDiv12 | 4696-0935 | nd | >1000 |
| ChemDiv14 | 8010-0630 | nd | >250 |
| SpecA | AK-968/37055109 | nd | >1000 |
| SpecC | AI-942/25034862 | nd | >250 |
| SpecD | AB-323/13887454 | nd | >1000 |
| SpecE | AC-364/37357066 | nd | >1000 |
| SpecG | AE-641/13303057 | nd | >1000 |
| SpecH | AF-399/40768858 | nd | >125 |
| SpecJ | AM-814/41093338 | nd | >1000 |

TABLE 4

Solubility and select data for Compounds from ChemBridge Co.
ChemBridge compounds

| | Compound ID | Formula | MW | Solvent | Solubility | Kd (uM) | E. coli assay |
|---|---|---|---|---|---|---|---|
| CB-1 | 5101730 | C18H16O4 | 296.32582 | MeOH | I | — | — |
| CB-2 | 5105134 | C14H8N2O8 | 332.22846 | MeOH | I | — | — |
| CB-3 | 5128372 | C16H10O6 | 298.2545 | MeOH | I | — | — |
| CB-4 | 5140501 | C10H7NO4 | 205.17159 | MeOH | S | — | — |
| CB-5 | 5173151 | C10H15N5 | 205.26455 | MeOH | S | 22.9 +/− 2.8826 | White pellet |
| CB-6 | 5173235 | C13H10N3NaO5S | 343.29555 | MeOH | I | — | — |
| CB-7 | 5191821 | C16H14N2O3 | 282.30158 | MeOH | S | 15.6 +/− 1.9387 | White pellet |
| CB-8 | 5233381 | C11H9NO5 | 235.19808 | MeOH | S | — | — |
| CB-9 | 5242836 | C12H15N3O2 | 233.27225 | MeOH | S | — | Green Pellet |
| CB-10 | 5261767 | C19H24N2 | 280.41653 | MeOH | I | — | — |
| CB-11 | 5317991 | C8H8N6O | 204.19256 | MeOH | I | — | — |
| CB-12 | 5345917 | C16H22N2 | 242.36714 | MeOH | I | — | — |
| CB-13 | 5350435 | C16H26N2O | 262.39842 | MeOH | I | — | — |
| CB-14 | 5351316 | C15H24N6O2 | 320.39753 | MeOH | S | — | — |
| CB-15 | 5373938 | C9H9N5O2 | 219.20438 | MeOH | S | — | — |
| CB-16 | 5405901 | C15H8ClNO4 | 301.68831 | MeOH | S | — | — |
| CB-17 | 5469632 | C16H13NO5 | 299.28571 | MeOH | I | — | — |
| CB-18 | 5474974 | C17H14ClN3O | 311.77363 | MeOH | S | 14.1 +/− 2.6014 | White pellet |
| CB-19 | 5483362 | C9H7N7O4 | 277.20064 | MeOH | I | — | — |
| CB-20 | 5491548 | C20H18N4O2 | 346.39206 | MeOH | I | — | — |
| CB-21 | 5509623 | C10H8N2O2S | 220.25146 | MeOH | I | — | — |
| CB-22 | 5538509 | C15H13N3O4 | 299.28856 | MeOH | I | — | — |
| CB-23 | 5546064 | C15H10N2O2 | 250.25915 | MeOH | I | — | — |
| CB-24 | 5549127 | C12H10ClN3O | 247.686 | MeOH | I | — | — |
| CB-25 | 5614227 | C18H15N3O6 | 369.33675 | MeOH | S | — | — |
| CB-26 | 5650366 | C16H11N3O4 | 309.28377 | MeOH | I | — | — |
| CB-27 | 5753497 | C18H16N6O | 332.36782 | MeOH | I | — | — |
| CB-28 | 5773916 | C14H11N5S | 281.34127 | MeOH | I | — | — |
| CB-29 | 5881261 | C13H17N3O6 | 311.29694 | MeOH | S | — | — |

TABLE 4-continued

Solubility and select data for Compounds from ChemBridge Co.
ChemBridge compounds

|       | Compound ID | Formula     | MW        | Solvent | Solubility | Kd (uM)         | *E. coli* assay |
|-------|-------------|-------------|-----------|---------|------------|-----------------|-----------------|
| CB-30 | 5914078     | C14H18N2O2  | 246.31176 | MeOH    | I          | —               | —               |
| CB-31 | 5928257     | C13H14ClN7  | 303.75643 | MeOH    | S          | 12.2 +/− 0.9882 | White pellet    |
| CB-32 | 5940661     | C15H12O4    | 256.26049 | MeOH    | S          | —               | —               |
| CB-33 | 6098968     | C14H15N5O2  | 285.30795 | MeOH    | S          | —               | —               |
| CB-34 | 6139643     | C13H13NO4   | 247.25286 | MeOH    | I          | —               | —               |
| CB-35 | 6141274     | C20H14N4O3  | 358.35958 | MeOH    | S          | 20.9 +/− 4.55628| White pellet    |
| CB-36 | 6157486     | C16H16O5    | 288.30292 | MeOH    | I          | —               | —               |
| CB-37 | 6526505     | C16H16N2O3  | 284.31752 | MeOH    | I          | —               | —               |
| CB-38 | 6633579     | C11H9ClN2O4 | 268.65838 | MeOH    | S          | —               | Green Pellet    |
| CB-39 | 6636465     | C12H11NO6   | 265.22457 | MeOH    | S          | —               | —               |

Note:
S = soluble, I = Insoluble
Indicates binding = +

TABLE 5

Solubility and select biological data for Compounds from Chemical Diversity Co.
Chemical diversity compounds

|          | Compound ID | Formula      | MW       | Solvent     | Solubility | Km (uM)         | *E. coli* Assay |
|----------|-------------|--------------|----------|-------------|------------|-----------------|-----------------|
| ChemDiv 1  | 0091-0260 | C16H11N3O6   | 341.2826 | EtOH        | I          | —               | —               |
| ChemDiv 2  | 0139-0251 | C10H7NO4     | 205.1716 | EtOH        | S          | +               | —               |
| ChemDiv 3  | 0173-0031 | C9H11N4O3    | 223.213  | EtOH        | I          | —               | —               |
| ChemDiv 4  | 0812-1008 | C15H8N2O3    | 264.2426 | EtOH        | I          | —               | —               |
| ChemDiv 5  | 1300-0270 | C10H10N2O2   | 190.2034 | EtOH        | S          | —               | —               |
| ChemDiv 6  | 1824-0926 | C10H9FN4O2   | 236.2072 | EtOH        | I          | —               | —               |
| ChemDiv 7  | 1988-0303 | C12H10N6O5   | 318.2507 | EtOH        | I          | —               | —               |
| ChemDiv 8  | 2181-0037 | C18H16N4O    | 304.3544 | EtOH        | I          | —               | —               |
| ChemDiv 9  | 2226-0401 | C10H11N3O2   | 205.2181 | EtOH        | S          | —               | —               |
| ChemDiv 10 | 2825-0171 | C15H11NO3    | 253.2598 | EtOH        | I          | —               | —               |
| ChemDiv 11 | 4335-0782 | C15H11N3O3   | 281.2732 | EtOH        | I          | —               | —               |
| ChemDiv 12 | 4696-0935 | C12H14O4     | 222.243  | EtOH        | S          | +               | —               |
| ChemDiv 13 | 8005-4121 | C13H13NO3    | 231.2535 | MeOH        | S          | +               | —               |
| ChemDiv 14 | 8010-0630 | C14H13Cl2NO  | 282.1718 | MeOH        | S          | —               | —               |
| ChemDiv 15 | 8010-3066 | C12H17N7O    | 275.3156 | MeOH        | S          | +               | —               |
| ChemDiv 16 | 8010-5978 | C15H11N3O2S  | 297.3378 | MeOH        | I          | —               | —               |
| ChemDiv 17 | 8012-4154 | C9H6N6O3     | 246.1866 | MeOH        | I          | —               | —               |
| ChemDiv 18 | K781-2231 | C12H10N4O2   | 242.2931 | MeOH        | S          | 33.5 +/− 4.0829 | Green Pellet    |
| ChemDiv 19 | R152-0479 | C8H19N3      | 157.2607 | MeOH        | S          | —               | —               |
| ChemDiv 20 | 0795-0144 | C13H11N3O3   | 257.2509 | MeOH        | I          | —               | —               |
| ChemDiv 21 | 2235-0060 | C14H13N5O2   | 283.292  | MeOH        | S          | —               | —               |
| ChemDiv 22 | 8003-8606 | C13H12N2O2   | 228.2528 | MeOH        | S          | 12.3 +/− 1.5759 | —               |
| ChemDiv 23 | 8007-8333 | C14H12N2O4   | 272.2627 | EtOH + MeOH | I          | —               | —               |
| ChemDiv 24 | 8011-1056 | C10H9N3O4S   | 267.2649 | MeOH        | S          | +               | —               |

Note:
S = soluble, I = Insoluble
Indicates binding = +

TABLE 6

Solubility and select biological data for Compounds from Maybridge Co.
Maybridge compounds

|       | Compound ID | MW       | Solvent | Solubility | Km (uM)         | *E. coli* Assay |
|-------|-------------|----------|---------|------------|-----------------|-----------------|
| MayB1 | JFD 01266   | 203.1993 | EtOH    | S          | +               | —               |
| MayB2 | GK 01678    | 204.2084 | EtOH    | S          | +               | —               |
| MayB3 | RFJ 00785   | 229.2404 | EtOH    | I          | —               | —               |
| MayB4 | BTB 02612   | 314.2625 | EtOH    | I          | —               | —               |
| MayB5 | CD 01521    | 241.2023 | EtOH    | I          | —               | —               |
| MayB6 | BTB 13061   | 265.271  | EtOH    | S          | 28.8 +/− 3.2626 | Toxic           |
| MayB7 | BTB 12037   | 278.3133 | EtOH    | I          | —               | —               |
| MayB8 | SEW 04440   | 294.3315 | EtOH    | I          | —               | —               |

TABLE 6-continued

Solubility and select biological data for Compounds from Maybridge Co.

Maybridge compounds

| | Compound ID | MW | Solvent | Solubility | Km (uM) | *E. coli* Assay |
|---|---|---|---|---|---|---|
| MayB9 | SB 02108 | 175.1916 | EtOH | I | — | — |
| MayB10 | NH 00373 | 244.255 | EtOH | S | — | — |

Note:
S = soluble, I = Insoluble
Indicate binding = +

Cluster of Compounds Including Formula 1 of FIG. 2 and General Formulae

Compound 1 in paper
chembridge0153140 77% 42cpds

| COMP_NAME | Weight | logP(o/w) |
|---|---|---|
| asinex45418 | 275.315 | 6.1475301 |
| asinex59401 | 684.77197 | 10.566 |
| asinex59402 | 382.431 | 5.0040002 |
| asinex59405 | 415.888 | 6.8649998 |
| asinex102624 | 396.418 | 8.42906 |
| asinex102630 | 574.612 | 10.90859 |
| asinex102736 | 276.30301 | 4.9155302 |
| asinex105583 | 309.75998 | 6.7395301 |
| asinex105607 | 309.75998 | 6.7765298 |
| asinex105635 | 275.315 | 6.1475301 |
| asinex116520 | 276.30301 | 4.8765302 |
| asinex05601 | 381.44299 | 6.2360001 |
| asinex05602 | 415.888 | 6.8280001 |
| chembridge039491 | 381.44299 | 6.2360001 |
| chembridge039511 | 415.888 | 6.8280001 |
| chembridge0111250 | 337.76099 | 9.8269997 |
| chembridge0111252 | 459.573 | 11.117 |
| chembridge0153140 | 303.75699 | 7.0549998 |
| chembridge0153310 | 303.75699 | 7.0570002 |
| chemdiv080008 | 415.888 | 6.8280001 |
| chemdiv095168 | 382.431 | 5.0029998 |
| chemdiv152115 | 382.431 | 5.0040002 |
| chemdiv172421 | 684.77197 | 10.566 |
| chemdiv0232796 | 381.44299 | 6.2360001 |
| chemdiv0285940 | 248.289 | 5.4099998 |
| nanosyn012844 | | |
| nanosyn014943 | | |
| nci0056134 | 267.29599 | 5.9629998 |
| nci0081371 | 213.244 | 3.8069999 |
| nci0086886 | 266.30798 | 4.204 |
| nci0109167 | 284.34698 | 5.6669998 |
| nci0165219 | 284.34698 | 5.6669998 |
| nci0201508 | 284.34698 | 5.743 |
| nci0206128 | 249.705 | 5.152 |
| nci0206131 | 340.81799 | 6.027 |
| nci0231493 | 384.82999 | 7.8835301 |
| nci0237251 | 284.34698 | 5.6669998 |
| specs0109062 | 415.888 | 6.8280001 |
| specs4040481 | 318.34399 | 9.0130596 |
| timtt214320 | 381.44299 | 6.2360001 |
| timtt4002241 | 415.888 | 6.8280001 |
| timtt4028714 | 684.77197 | 10.566 | chembridge0153140 78% 21cpds

| COMP_NAME | Weight | logP(o/w) |
|---|---|---|
| asinex59401 | 684.77197 | 10.566 |
| asinex59405 | 415.888 | 6.8649998 |
| asinex102624 | 396.418 | 8.42906 |
| asinex105583 | 309.75998 | 6.7395301 |
| asinex105607 | 309.75998 | 6.7765298 |
| asinex05602 | 415.888 | 6.8280001 |
| chembridge039511 | 415.888 | 6.8280001 |
| chembridge0153140 | 303.75699 | 7.0549998 |
| chembridge0153310 | 303.75699 | 7.0570002 |
| chemdiv080008 | 415.888 | 6.8280001 |
| chemdiv172421 | 684.77197 | 10.566 |
| nanosyn012844 | | |
| nci0056134 | 267.29599 | 5.9629998 |
| nci0081371 | 213.244 | 3.8069999 |
| nci0206128 | 249.705 | 5.152 |
| nci0206131 | 340.81799 | 6.027 |
| nci0231493 | 384.82999 | 7.8835301 |
| specs0109062 | 415.888 | 6.8280001 |
| specs4040481 | 318.34399 | 9.0130596 |
| timtt4002241 | 415.888 | 6.8280001 |
| timtt4028714 | 684.77197 | 10.566 |

General Formulae related to Cluster of Compounds Including Formula 1 of FIG. 2

General Formula I

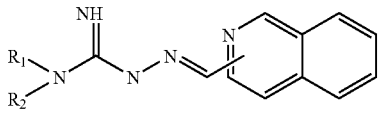

Where $R_1$ and $R_2$ are independently hydrogen or

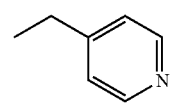

General Formula II

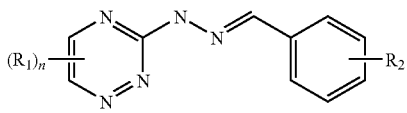

where n is 1 or 2

$R_1$ and $R_2$ are independently aryl, halogen, Cl,

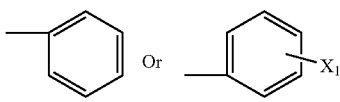

Where X is halogen or Cl,
or when n is 2, two $R_1$ groups may form a heteraryl ring General Formula III

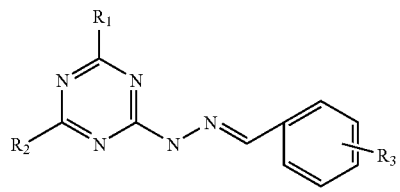

Where $R_1$ and $R_2$ are

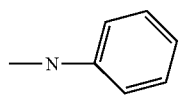

and $R_3$ is halogen or Cl.

General Formula IV

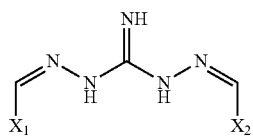

Where $X_1$ and $X_2$ are

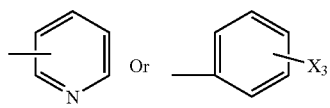

where $X_3$ is halogen, Br or F.

Cluster of Compounds Including Formula 2 of FIG. 2 and General Formulae

| Compound 2 in paper chembridge047908 86% 28cpds | | |
|---|---|---|
| COMP_NAME | Weight | logP(o/w) |
| asinex134998 | 297.745 | 4.651 |
| asinex135027 | 277.327 | 4.1469998 |
| chembridge011461 | 297.745 | 4.6880002 |
| chembridge047163 | 311.772 | 4.7399998 |
| chembridge047908 | 311.772 | 4.7389998 |
| chembridge048652 | 346.21698 | 5.3670001 |
| chembridge055166 | 356.22299 | 4.9819999 |
| chembridge060191 | 273.72299 | 3.1400001 |
| chembridge065602 | 295.31699 | 4.3369999 |
| chembridge087076 | 346.21698 | 5.3660002 |

| Compound 2 in paper chembridge047908 86% 28cpds | | |
|---|---|---|
| COMP_NAME | Weight | logP(o/w) |
| chemdiv024075 | 360.24399 | 5.2919998 |
| chemdiv026253 | 327.38699 | 5.3670001 |
| chemdiv043952 | 346.21698 | 5.3270001 |
| chemdiv110850 | 311.772 | 4.7389998 |
| chemdiv117558 | 277.327 | 4.1469998 |
| chemdiv117768 | 297.745 | 4.651 |
| chemdiv122071 | 406.28299 | 6.1630001 |
| chemdiv126462 | 297.745 | 4.6880002 |
| chemdiv0232015 | 295.31699 | 4.3000002 |
| chemdiv0232101 | 356.22299 | 4.9450002 |
| chemdiv4046525 | 327.38699 | 5.3670001 |
| nanosyn004275 | | |
| nanosyn006430 | | |
| nanosyn017813 | | |
| specs4022026 | 346.21698 | 5.3270001 |
| specs4061287 | 356.22299 | 4.9819999 |
| specs4061288 | 311.772 | 4.737 |
| timtt4027154 | 346.21698 | 5.3270001 |

General Formulae related to Cluster of Compounds Including Formula 2 of FIG. 2

General Formula V

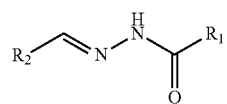

where one of $R_1$ or $R_2$ is

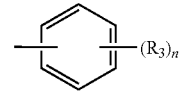

where n is 0-5
$R_3$ is halogen, Cl, Br, F or two $R_3$s together form a naphthyl ring
and the other is

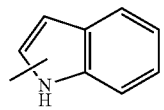

Preferably, one of $R_1$ or $R_2$ is

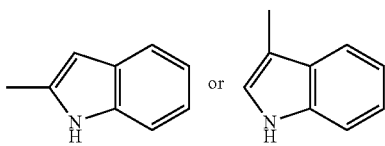

Cluster of Compounds including Formula 3 of FIG. 2 and General Formulae

| Compound 3 in paper chembridge010392 92% 91cpds | | |
|---|---|---|
| COMP_NAME | Weight | logP(o/w) |
| asdi0020059 | 380.35599 | 2.494 |
| asdi0037122 | 256.26099 | 1.938 |
| asinex40600 | 256.26099 | 1.864 |
| asinex46264 | 404.37799 | 3.24 |
| asinex51224 | 354.31799 | 1.752 |
| asinex52013 | 404.37799 | 3.277 |
| asinex56231 | 394.383 | 2.582 |
| asinex56940 | 564.54999 | 4.8520002 |
| asinex56958 | 434.40399 | 2.767 |
| asinex56970 | 311.293 | 2.9679999 |
| asinex120733 | 492.396 | 2.7420001 |
| asinex114220 | 256.26099 | 1.938 |
| asinex93016 | 331.371 | 4.3060002 |
| asinex137373 | 380.35599 | 2.494 |
| asinex132199 | 492.396 | 2.779 |
| asinex132346 | 611.51898 | 3.806 |
| mdd012497 | 281.311 | 3.5150001 |
| mdsi0004923 | 267.284 | 3.217 |
| mdsi0005850 | 380.35599 | 2.494 |
| mdsi0006340 | 404.37799 | 3.1659999 |
| mdsi0006341 | 404.37799 | 3.2030001 |
| mdsi0006342 | 404.37799 | 3.277 |
| mdsi0006595 | 331.371 | 4.3060002 |
| mdsi0007042 | 331.371 | 4.2690001 |
| mdsi0008153 | 267.284 | 3.217 |
| mdsi0011785 | 256.26099 | 1.864 |
| chembridge004734 | 241.24599 | 2.4400001 |
| chembridge004793 | 241.24599 | 2.4790001 |
| chembridge009285 | 404.37799 | 3.1659999 |
| chembridge009286 | 404.37799 | 3.24 |
| chembridge009288 | 404.37799 | 3.2030001 |
| chembridge009289 | 404.37799 | 3.277 |
| chembridge009807 | 311.293 | 2.9679999 |
| chembridge010392 | 282.29898 | 2.602 |
| chembridge012760 | 267.284 | 3.1800001 |
| chembridge013348 | 267.284 | 3.217 |
| chembridge014715 | 380.35599 | 2.494 |
| chembridge016339 | 492.396 | 2.779 |
| chembridge016367 | 611.51898 | 3.806 |
| chembridge018248 | 293.32199 | 3.8239999 |
| chembridge019639 | 331.371 | 4.3060002 |
| chembridge021875 | 267.284 | 3.217 |
| chembridge079619 | 256.26099 | 1.901 |
| chembridge101012 | 241.24599 | 2.573 |
| chembridge0121454 | 354.31799 | 1.752 |
| chembridge0251182 | 492.396 | 2.7420001 |
| chembridge0291235 | 241.24599 | 2.4400001 |
| chemdiv045962 | 450.49399 | 5.2589998 |
| chemdiv055486 | 241.24599 | 2.573 |
| chemdiv055989 | 256.26099 | 1.864 |
| chemdiv060567 | 241.24599 | 2.536 |
| chemdiv073662 | 331.371 | 4.3060002 |
| chemdiv078253 | 267.284 | 3.217 |
| chemdiv098023 | 241.24599 | 2.4400001 |
| chemdiv098024 | 354.31799 | 1.752 |
| chemdiv121639 | 241.24599 | 2.4790001 |
| chemdiv121641 | 293.32199 | 3.8239999 |
| chemdiv160266 | 311.293 | 2.9679999 |
| chemdiv164089 | 404.37799 | 3.1659999 |
| chemdiv164540 | 404.37799 | 3.2030001 |
| chemdiv164825 | 267.284 | 3.1800001 |
| chemdiv166491 | 404.37799 | 3.277 |
| chemdiv174205 | 331.371 | 4.2690001 |
| maybridge0437703 | | |
| maybridge0445740 | | |
| nanosyn000327 | | |
| nanosyn018823 | | |
| nanosyn021101 | | |
| nanosyn027586 | | |
| nanosyn051055 | | |

| Compound 3 in paper chembridge010392 92% 91cpds | | |
|---|---|---|
| COMP_NAME | Weight | logP(o/w) |
| nci0012510 | 354.31799 | 1.752 |
| nci0021935 | 241.24599 | 2.4400001 |
| nci0035677 | 241.24599 | 2.4400001 |
| nci0040728 | 394.383 | 2.582 |
| nci0046361 | 404.37799 | 3.1659999 |
| nci0055729 | 267.284 | 3.1800001 |
| nci0059951 | 241.24599 | 2.536 |
| nci0066338 | 241.24599 | 2.573 |
| nci0086175 | 394.383 | 2.582 |
| nci0122691 | 241.24599 | 2.4400001 |
| specs0136285 | 404.37799 | 3.277 |
| specs4010034 | 404.37799 | 3.1659999 |
| specs4029389 | 331.371 | 4.3060002 |
| specs4029506 | 267.284 | 3.1800001 |
| st004068 | 281.311 | 3.5150001 |
| timtt004666 | 281.311 | 3.5150001 |
| timtt018772 | 331.371 | 4.2690001 |
| timtt018773 | 331.371 | 4.3060002 |
| timtt037049 | 404.37799 | 3.2030001 |
| timtt054936 | 282.29898 | 2.602 |
| timtt4077074 | 241.24599 | 2.573 |

| chembridge010392 93% 10cpds | | |
|---|---|---|
| COMP_NAME | Weight | logP(o/w) |
| mdsi0004923 | 267.284 | 3.217 |
| mdsi0008153 | 267.284 | 3.217 |
| chembridge010392 | 282.29898 | 2.602 |
| chembridge013348 | 267.284 | 3.217 |
| chembridge018248 | 293.32199 | 3.8239999 |
| chembridge021875 | 267.284 | 3.217 |
| chemdiv078253 | 267.284 | 3.217 |
| chemdiv121641 | 293.32199 | 3.8239999 |
| nanosyn051055 | | |
| timtt054936 | 282.29898 | 2.602 |

General Formulae related to Cluster of Compounds Including Formula 3 of FIG. 2

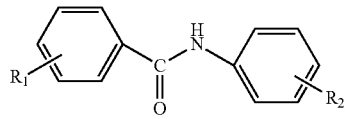

General Formula VI wherein $R_1$ and $R_2$ are independently H, N(—$NH_2$),

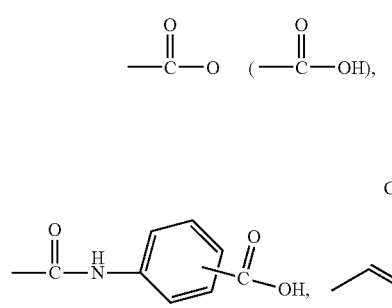

General Formula VII

-continued

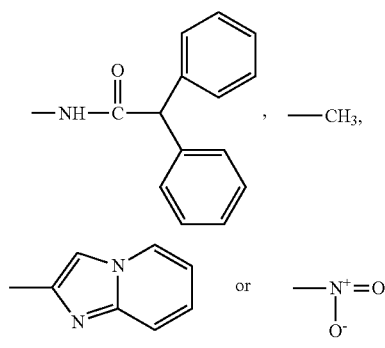

Where n is 1 or 2
R is

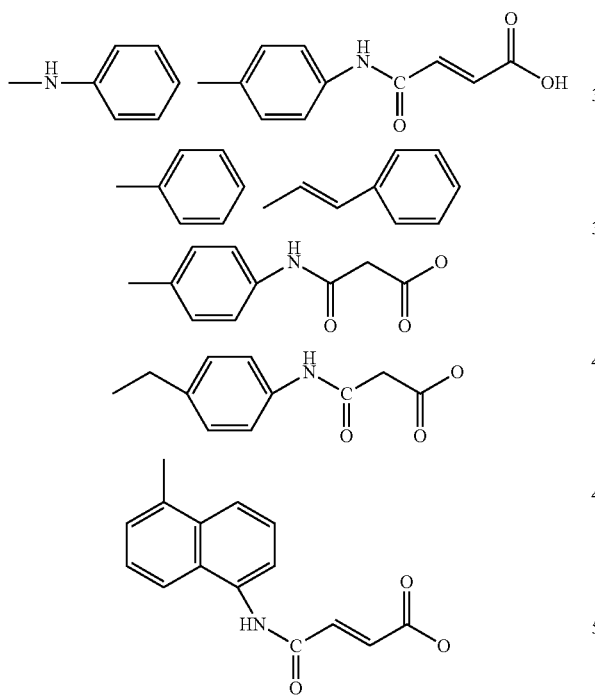

Or two Rs form a naphthyl ring.

General Formula VIII

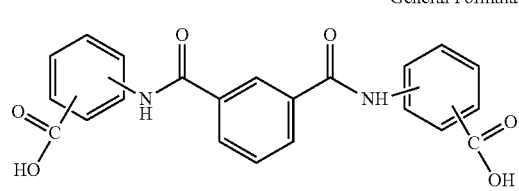

-continued

General Formula IX

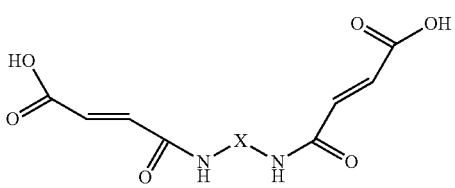

Where X is

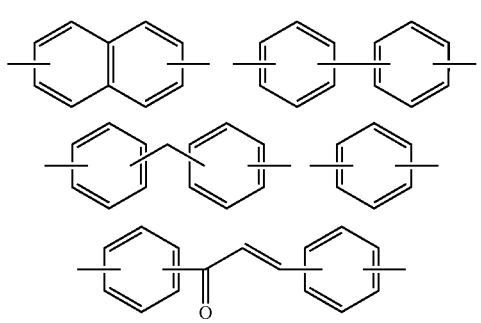

Cluster of Compounds including Formula 5 of FIG. 2 and General Formulae

| chembridge008493 78% 32 cpds Compound 5 in paper | | |
|---|---|---|
| COMP_NAME | Weight | logP(o/w) |
| mdd009726 | 222.31599 | 3.5550001 |
| mdsi0009589 | 248.354 | 4.1989999 |
| chembridge008493 | 205.265 | 3.773 |
| chembridge015566 | 258.77701 | 4.6490002 |
| chembridge0121736 | 222.31599 | 3.5550001 |
| chembridge0144445 | 222.31599 | 3.326 |
| chembridge0176644 | 205.265 | 2.165 |
| chemdiv042412 | 206.24899 | 1.234 |
| chemdiv064772 | 205.265 | 3.773 |
| chemdiv074619 | 222.31599 | 3.5550001 |
| chemdiv170000 | 298.414 | 5.6090002 |
| chemdiv0309465 | 252.326 | −0.877 |
| maybridge0403597 | | |
| maybridge0409051 | | |
| maybridge0438624 | | |
| maybridge0446502 | | |
| nanosyn004772 | | |
| nanosyn012449 | | |
| nci0001584 | 206.24899 | 1.234 |
| nci0003243 | 222.31599 | 3.5550001 |
| nci0053514 | 233.319 | 4.4549999 |
| nci0053904 | 205.265 | 3.773 |
| nci0058422 | 102.141 | −0.685 |
| nci0058433 | 233.319 | 3.997 |
| nci0104186 | 192.26599 | 0.597 |
| nci0115300 | 269.21298 | 4.3530002 |
| nci0136373 | 204.27699 | 3.1559999 |
| nci0142845 | 298.414 | 5.6090002 |
| nci0200577 | 341.483 | 5.0580001 |
| specs4130775 | 298.414 | 5.6090002 |
| st001085 | 222.31599 | 3.5550001 |
| timtt001256 | 222.31599 | 3.5550001 |

General Formulae related to Cluster of Compounds Including Formula 5 of FIG. 2

Cluster of Compounds including Formula 7 of FIG. 2 and General Formulae

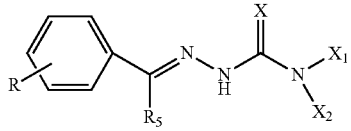

General Formula X

Wherein X is S, O, N(NH)

$X_1$ and $X_2$ are independently halogen, Cl, —$CH_3$, H or

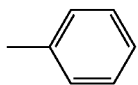

R is

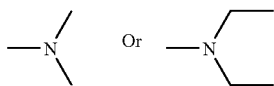

$R_5$ is H or

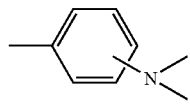

Preferably R is in the para position.

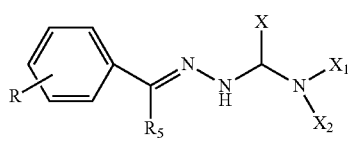

General Formula XI

Where X is SH or

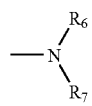

Where $R_6$ and $R_7$ are independently H, —$CH_3$, or

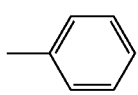

And R, $R_5$, $X_1$ and $X_2$ are as shown in General Formula X.

| Comp. 7 in paper chemdiv0324743 86% 45cpds | | |
|---|---|---|
| COMP_NAME | Weight | logP(o/w) |
| asdi0009550 | 372.388 | 3.016 |
| asinex46918 | 242.23799 | 0.053 |
| asinex06955 | 372.388 | 3.016 |
| bionet0025752 | 242.23799 | 0.054 |
| mdd0502977 | 255.27699 | 1.5829999 |
| mdd0527911 | 241.25 | 1.285 |
| mdd003181 | 255.27699 | 1.5829999 |
| chembridge004397 | 179.179 | −0.376 |
| chembridge006273 | 255.27699 | 1.5829999 |
| chembridge013643 | 255.27699 | 1.584 |
| chembridge032358 | 372.388 | 3.016 |
| chembridge054485 | 267.28799 | 1.929 |
| chembridge103932 | 241.25 | 1.285 |
| chemdiv004507 | 267.28799 | 1.929 |
| chemdiv056645 | 179.179 | −0.376 |
| chemdiv091324 | 242.23799 | 0.053 |
| chemdiv099069 | 255.27699 | 1.5829999 |
| chemdiv099142 | 241.25 | 1.285 |
| chemdiv0300173 | 255.27699 | 1.6210001 |
| chemdiv0306184 | 241.25 | 1.286 |
| chemdiv0306979 | 242.23799 | 0.052 |
| chemdiv0324743 | 242.23799 | 0.054 |
| chemdiv0324745 | 242.23799 | 0.015 |
| chemdiv4026289 | 268.276 | 0.85352999 |
| maybridge0421835 | | |
| maybridge0432152 | | |
| nanosyn001769 | | |
| nanosyn009502 | | |
| nanosyn010080 | | |
| nanosyn010232 | | |
| nanosyn015890 | | |
| nci0031408 | 179.179 | −0.376 |
| nci0034151 | 242.23799 | 0.054 |
| nci0044839 | 242.23799 | 0.054 |
| nci0050300 | 404.38599 | 0.66600001 |
| nci0071634 | 241.25 | 1.247 |
| nci0071639 | 242.23799 | −0.024 |
| nci0191381 | 342.358 | 2.8440001 |
| nci0236899 | 241.29399 | 2.1199999 |
| nci0245446 | 242.23799 | −0.024 |
| specs4043821 | 331.375 | 2.98 |
| specs4130684 | 381.435 | 5.0110002 |
| timtt2003348 | 255.27699 | 1.5829999 |
| timtt2029430 | 241.25 | 1.285 |
| timtt4022381 | 241.25 | 1.286 |

| chemdiv0324743 88% 26cpds | | |
|---|---|---|
| COMP_NAME | Weight | logP(o/w) |
| asinex46918 | 242.23799 | 0.052999999 |
| bionet0025752 | 242.23799 | 0.054000001 |
| mdd0527911 | 241.25 | 1.285 |
| chembridge013643 | 255.27699 | 1.584 |
| chembridge103932 | 241.25 | 1.285 |
| chemdiv091324 | 242.23799 | 0.052999999 |
| chemdiv099142 | 241.25 | 1.285 |
| chemdiv0300173 | 255.27699 | 1.6210001 |
| chemdiv0306184 | 241.25 | 1.286 |
| chemdiv0306979 | 242.23799 | 0.052000001 |
| chemdiv0324743 | 242.23799 | 0.054000001 |
| chemdiv0324745 | 242.23799 | 0.015 |
| maybridge0421835 | | |
| nanosyn001769 | | |
| nanosyn010080 | | |
| nanosyn010232 | | |

-continued chemdiv0324743 88% 26cpds

| COMP_NAME | Weight | logP(o/w) |
|---|---|---|
| nci0034151 | 242.23799 | 0.054000001 |
| nci0044839 | 242.23799 | 0.054000001 |
| nci0050300 | 404.38599 | 0.66600001 |
| nci0071634 | 241.25 | 1.247 |
| nci0071639 | 242.23799 | −0.024 |
| nci0191381 | 342.358 | 2.8440001 |
| nci0245446 | 242.23799 | −0.024 |
| specs4043821 | 331.375 | 2.98 |
| timtt2029430 | 241.25 | 1.285 |
| timtt4022381 | 241.25 | 1.286 |

General Formulae related to Cluster of Compounds Including Formula 7 of FIG. 2

General Formula XII

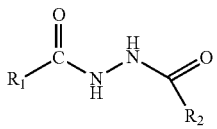

Where $R_1$ and $R_2$ are independently —$CH_3$, heteroaryl, aryl,

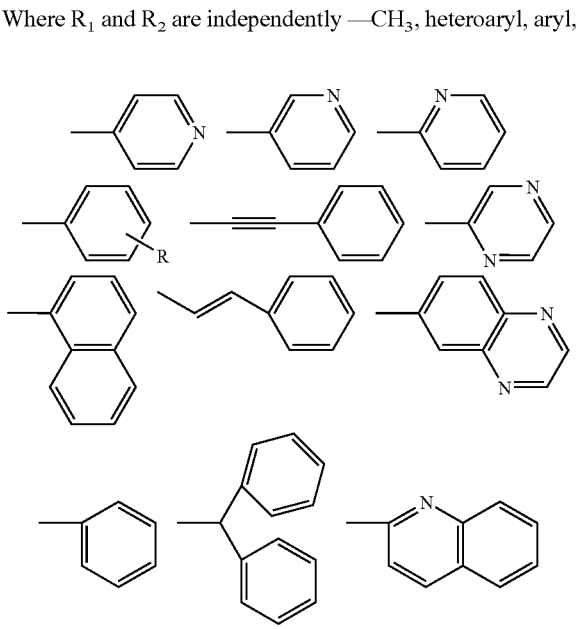

Where R is selected from alkyl and —$CH_3$.

General Formula XIII

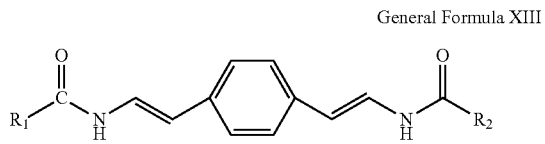

Wherein $R_1$ and $R_2$ are the same in General Formula XII.

General Formula XIV

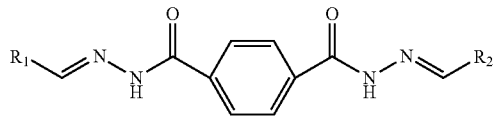

Wherein $R_1$ and $R_2$ are the same in General Formula XII.

Experimental Studies.

A series of experiments were undertaken on the 37 soluble compounds to identify those that both bind to HO in vitro and inhibit HO activity in vivo. In these experiments both nm-HO and pa-HO were tested for binding affinity and ability to inhibit enzymatic activity either in an *E. coli* expression system (nm-HO), or in the bacterial strain itself (pa-HO). Accordingly, systems for in vitro and in vivo selection were employed for both proteins in identifying biologically active compounds targeted to an inherently virulent pathogen *N. meningitidis* and an important opportunistic pathogen *P. aeruginosa*.

Binding Affinities ($K_D$) of Selected Inhibitors.

The initial experimental selection criteria was the ability of the inhibitors to bind to heme oxygenase, as determined by fluorescence quenching of the protein. Compounds were first tested for their excitation/emission spectral profiles to ensure they would not interfere with the emission profile of the purified protein. Of the 37 compounds, 8 were shown to have no intrinsic fluorescence associated with the compound but reduced protein (tryptophan) fluorescence when added in 10-fold excess. It should be noted that preclusion by fluorescence screening or insolubility by NMR methods and MIC50 assays with *P. aeruginosa* does not necessarily exclude compounds from being HO inhibitors.

The structures of the compounds that quenched protein fluorescence (Compounds 1-8) are shown in FIG. 2. Compounds 1-8 of FIG. 2 correspond to Compounds 148, 126, 75, 22, 1, 114, 24 and 13 of Table 2, respectively. The binding affinities ($K_D$'s) of the selected compounds calculated by the fluorescence titrations against both pa-HO and nm-HO are given in Table 1. The binding affinities for the selected compounds were all in the micromolar range. These 8 compounds were then subjected to additional experimental analysis as described below.

Inhibition of Biliverdin Production in an *E. coli* System Expressing nm-HO.

Figure 3:
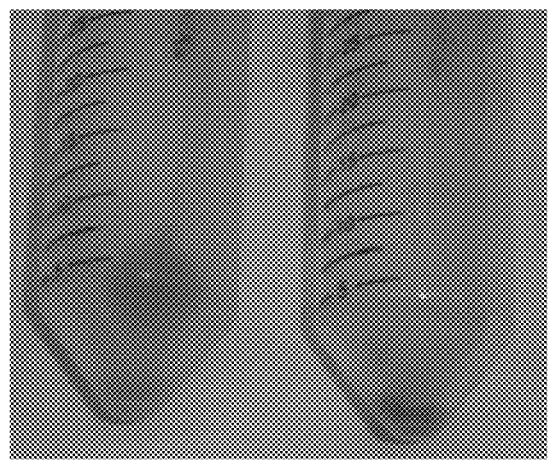
FIG. 3. Inhibition of nm-HO in an *E. coli* expression system.
A. Cell pellets of cultures either treated with 1500 μM Inhibitor 3 (1) or untreated (2).
B. HPLC analysis of the extracted products of the compound treated (- - - - -) and untreated (—) cultures. The peak observed at 3-5 min in the treated cultures is due to the extracted compound. The shoulder on the internal standard peak is due to β-biliverdin. Extraction and HPLC analysis were carried out as described in the Experimental Section.
Figure 3:
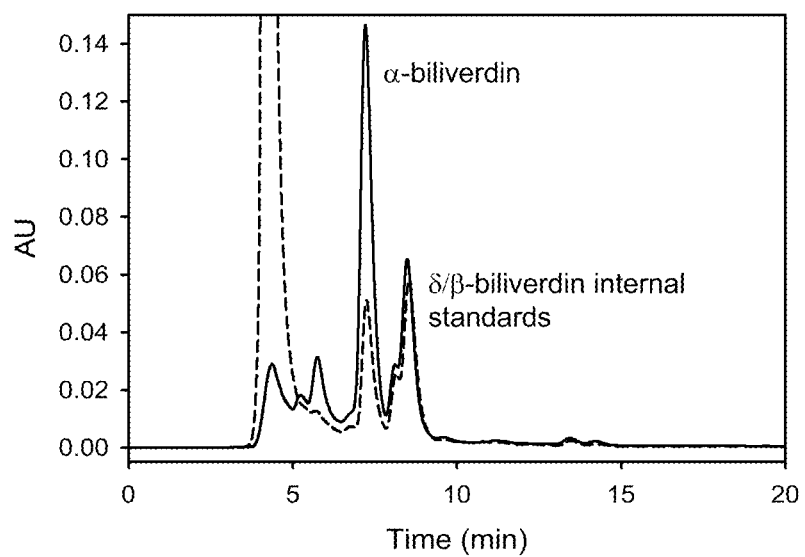

The eight compounds were next assessed for their ability to inhibit the production of α-biliverdin in *E. coli* cells expressing nm-HO. Several of the compounds (Compounds 1-5 of FIG. 2) inhibited the production of α-biliverdin in an *E. coli* expression system as judged by the lack of pigmentation in the cells (Table 1 and FIG. 3A). Extraction and HPLC analysis of the products from untreated cells or cells treated with Compound 3 of FIG. 2 confirmed that the lack of pigmentation was due to the inhibition of α-biliverdin production (FIG. 3B). As an internal standard, the product of the pa-HO reaction, which is a 30:70 ratio of β/δ-biliverdin, was added to the lysed cells prior to extraction of the reaction products. As shown in FIG. 3B the extraction of biliverdin from untreated and cells treated with Compound 3 of FIG. 2 yielded similar levels of the internal standard (β/δ-biliverdin). In stark contrast, a marked decrease in the nm-HO catalyzed α-biliverdin product is observed in the cells treated with Compound 3 of FIG. 2. Integration of the α-biliverdin peak from the control culture compared to the treated cells (accounting for the levels of the extracted internal standard) estimated a 60% decrease in α-biliverdin product as a consequence of nm-HO inhibition.

Growth Inhibition of *P. aeruginosa* MPA01.

Figure 4:
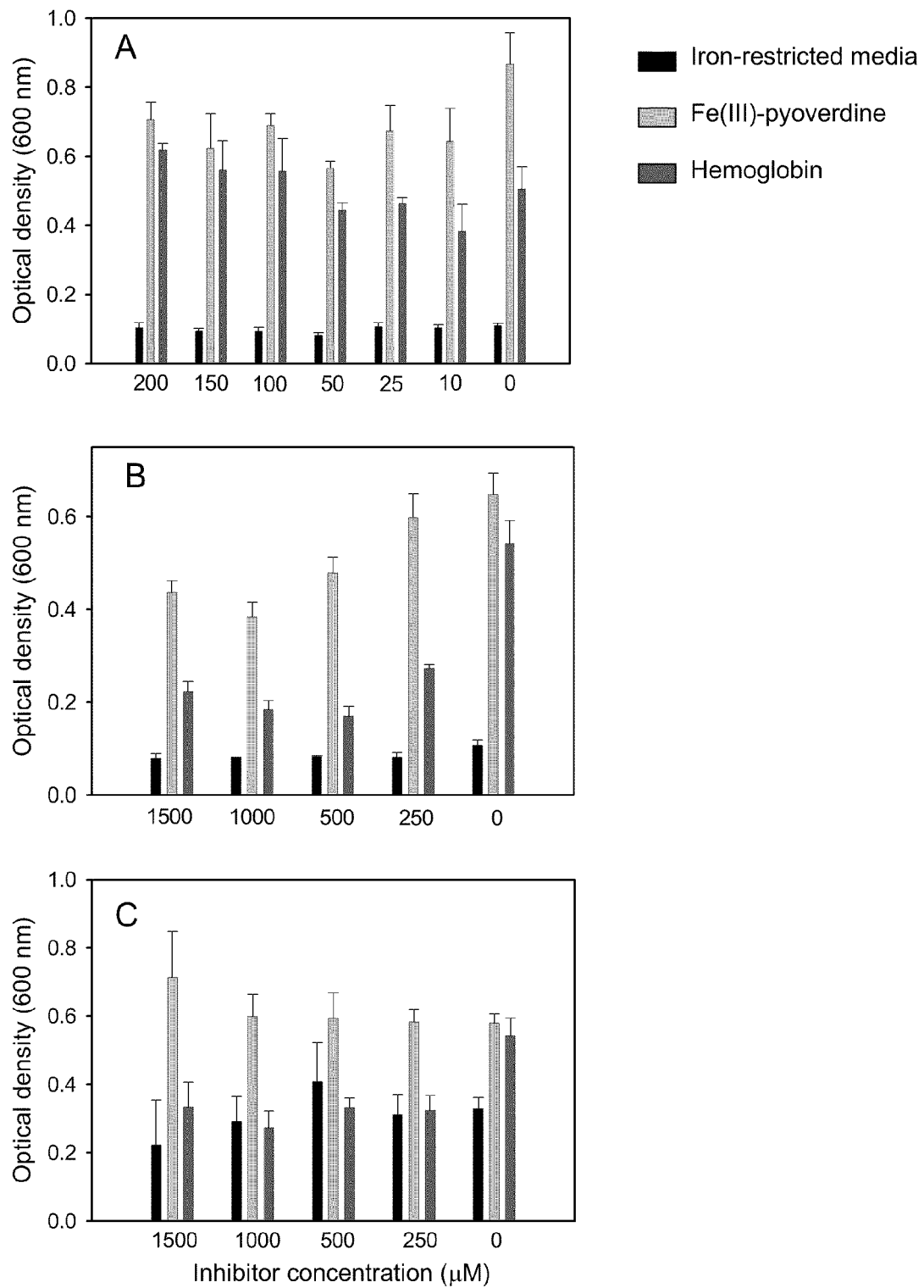
FIG. 4. Growth analysis of *P. aeruginosa* MPA01 in the presence of various concentrations of Compound 3 of FIG. 2 as a function of iron source.
Cultures (10 ml) were grown from an initial $OD_{600}$ of 0.05 for 10 hours in iron-restricted SM-medium in the presence or absence of compound at various concentrations. Where indicated the cells were supplemented with Fe(III)-pyoverdine or hemoglobin as an iron source.
A. Compound 3 of FIG. 2 at 0-200 μM concentrations.
B. Compound 3 of FIG. 2 at 0-1500 μM concentrations.
C. Compound 3 of FIG. 2 at 0-1500 μM concentrations.
Figure 5:
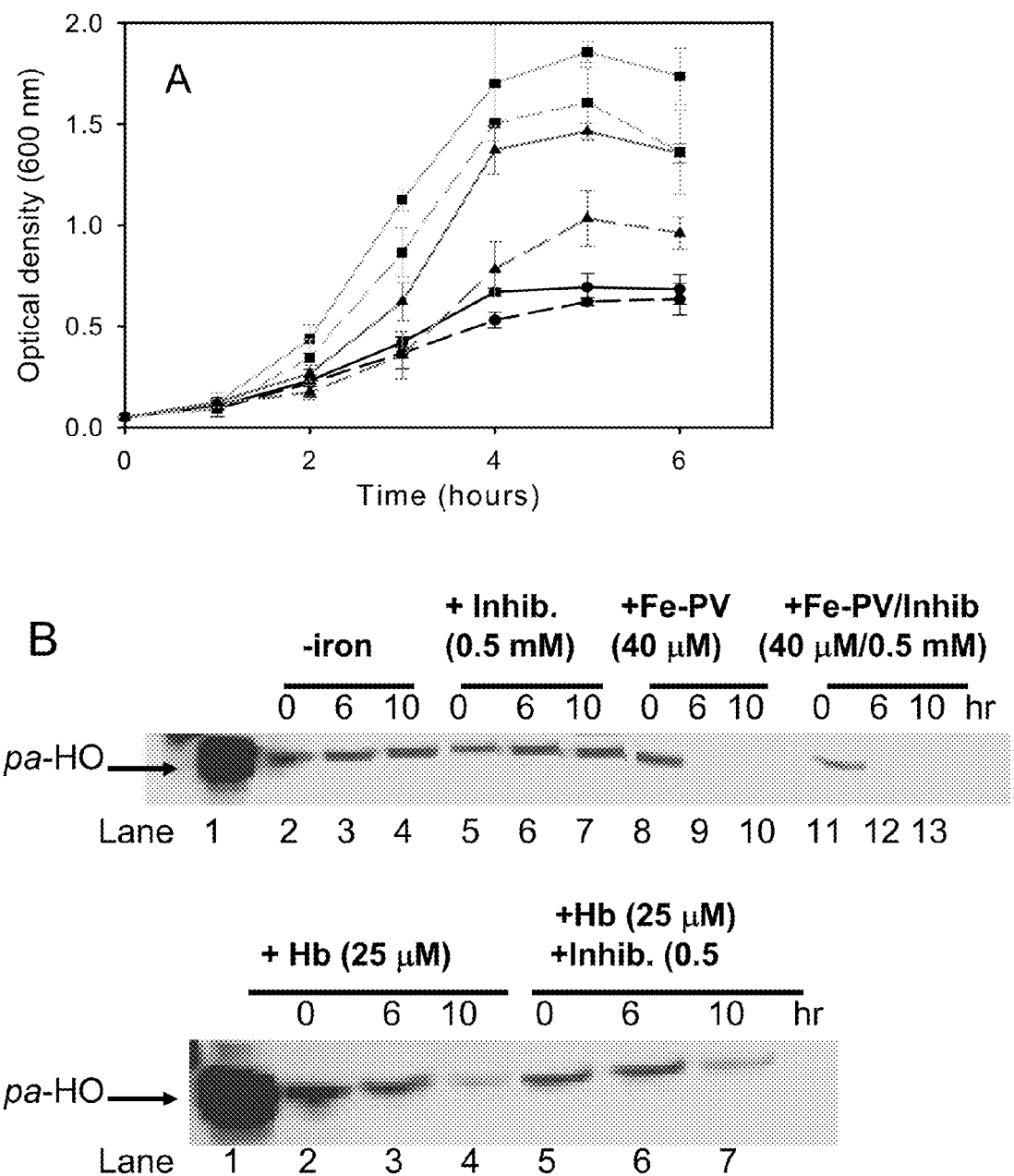
FIG. 5. Growth inhibition and pa-HO protein expression levels of *P. aeruginosa* MPA01 in the presence of Compound 3 of FIG. 2.
Cultures of *P. aeruginosa* PA01 (15 ml) at a starting $OD_{600}$ of 0.05 were grown over a 6 hour growth period in iron-restricted media in the presence or absence of Compound 3 of FIG. 2 (500 μM). The data are the average of three separate experiments.
A. Growth curve of MPAO1 in iron restricted media in the absence of compound (—) or in the presence of compound (- - - -); MPAO1 supplemented with 40 μM Fe(III)-pyoverdine (—) or 40 μM Fe(III)-pyoverdine in the presence of compound (- - - -); MPAO1 supplemented with 25 μM hemoglobin as the iron source (—) or 25 μM hemoglobin in the presence of compound (- - - -).
B. Western blot analysis of pa-HO expression levels with or without Compound 3 of FIG. 2 when supplemented with 40 μM Fe(III)-pyoverdine.
C. Western blot of pa-HO expression with or without Compound 3 of FIG. 2 supplemented with 25 μM hemoglobin.

Compounds 1 through 8 of FIG. 2 were further analyzed for their ability to inhibit the growth of MPA01 when given heme as the sole source of iron. MPA01 growth inhibition when heme is the iron source is a strong indication that HO activity plays a central role in obtaining iron necessary for cell viability. Concentrations of Compounds 1 through 8 of FIG. 2 at concentrations of 10-1500 μM were assessed for the ability to inhibit growth in 96-well growth assays. None of the compounds tested inhibited the growth of MPAO1 below 250 μM, whereas compounds 2 and 3 of FIG. 2 appeared to significantly decrease the growth of MPA01 at concentrations >250 μM (data not shown). In order to determine if the growth end-points observed in the 96-well assays resulted from a slower growth rate versus cell death, the growth of MPA01 in the presence of Compounds 2 or 3 of FIG. 2 was monitored in larger cultures at a single 10 hour time point and over the complete growth curve (FIGS. 4 and 5).

The growth inhibition of MPA01 in the presence of Compounds 2 or 3 of FIG. 2 was monitored at a final 10 hour time point with selected inhibitor concentrations ranging from 10-1500 μM. MPA01 cultures grown under iron-restricted conditions in the absence or presence of the compounds did not show a significant difference in growth, indicating that the compounds themselves were not toxic to the cells (FIG. 4). Furthermore, inhibitory effects of Compound 2 or 3 of FIG. 2 at 250 μM and above could be overcome on addition of Fe(III)-pyoverdine (40 μM), an alternate iron source not dependant on HO activity, to the cultures. At concentrations of Inhibitor 3 at 500 μM and above a slight inhibitory effect was observed even in the presence of Fe(III)-pyoverdine (FIG. 4B). In contrast when hemoglobin was provided as the sole iron source, the cultures in the absence of Compounds 2 or 3 of FIG. 2 attained optical densities similar to iron-replete media, whereas those in the presence of the inhibitor recovered approximately 40% of the growth of the control cultures provided Fe(III)-pyoverdine as an iron-source (FIGS. 4B and C). The present data is consistent with the observation presented above in which reduction of the α-biliverdin product in the *E. coli* expression system in the presence of inhibitor Compound 3 of FIG. 2, suggesting direct inhibition of HO activity is also responsible for the growth inhibition observed in the MPA01 strain.

It was further determined that the inhibition of growth of MPA01 in vivo was due to a slower growth rate over a 6 hour period. As shown in FIG. 5A in the presence of Compound 3 of FIG. 2 (500 μM) the slower growth rate in iron-restricted media could be largely overcome on addition of Fe(III)-pyoverdine. However, in the presence of hemoglobin as the sole iron source, the inhibition of growth was not overcome nor restored to the levels observed for the Fe(III)-pyoverdine supplemented cultures. In addition the slow growth rate of the bacterial cultures was shown to be due to inhibition of enzymatic activity of HO and not altered levels of protein expression as judged by Western blot analysis (FIG. 5B). Under iron-restricted conditions the HO levels are up-regulated. Additionally, it was noted that in the presence or absence of inhibitor Compound 3 of FIG. 2 no significant difference in protein expression levels was observed. However, when supplied with Fe(III)-pyoverdine the HO levels decrease significantly and are undetectable after 6 hours as the cells begin to utilize the iron provided by the siderophore uptake pathway (FIG. 5B). Similarly, the levels of HO expression decrease over time when hemoglobin is provided as the source of iron (FIG. 5C). The uptake and utilization of heme increases the cellular iron levels, initiating the Fur-dependent down regulation of the heme uptake genes, including HO. However, the protein levels are still detectable after 6 hours in the presence of hemoglobin versus Fe(III)-pyoverdine, as heme appears to be a positive regulator of HO expression, whereas when iron is supplied via the siderophore pathway the heme uptake genes are down-regulated more rapidly. These results taken together indicate that the inhibitor, when taken up by the bacteria cells, has no direct effect on the expression levels of the HO protein, further confirming that the decrease in biliverdin is solely due to inhibition of HO enzyme activity.

The CADD described in the present invention selects small molecule inhibitors of the HO apoprotein, for example, nm-HO apoprotein (apo-nm-HO), that are not analogs of heme or utilize coordination via the iron of the heme. This is in contrast to previous studies where it has been shown that metal substituted porphyrins are effective competitive inhibitors of mammalian heme oxygenase[42-45]. Some of these inhibitors, such as Zn(II)-protoporphyrin IX and Sn(IV)-protoporphyrin IX, have been used as therapeutic agents in the treatment of neonatal jaundice, a condition attributed to increased HO activity in newborn infants. However, because of the identical structural motif of the porphyrin macrocycle, such inhibitors have limited selectivity, in that other heme containing proteins including the cytochromes P450 (CYP), nitric oxide synthase (NOS) and soluble guanylate cyclase (sGC), are susceptible to metalloporphyrin inhibition[46-48].

The compounds of the present invention are not competitive inhibitors of heme oxygenase (i.e., are not competitors of heme oxygenase for heme and do not bind to heme). Rather, they bind with HO at the heme binding site so that HO is no longer active to heme.

One goal is the selective microbial and bacterial HO inhibition and not to target the protein of the infected organism (i.e., animal or human), which has been the focus of other patents.

The compounds of the present invention are not structural analogs of FePP (e.g., metal analogs and porphyrin analogs (e.g., mesoporphyrins and diiododeuteroporphyrins)).

The compounds of the present invention are not porphyrins or derivatives of porphyrins. The compounds of the present invention are not metal porphyrins or metal protoporphyrins or derivatives of metal porphyrins or metal protoporphyrins.

Heme oxygenase inhibitors developed more recently include the imidazole-dioxolones which have been shown to selectively inhibit the mammalian HO-1 (inducible) versus HO-2 (constitutive) isoform[49]. The diaxolone inhibitors were developed by synthetic modification of the lead compound azalanstat, an inhibitor of lanosterol 14 α-demethylase, a fungal CYP and a critical enzyme in the lanosterol biosynthetic pathway[50]. These inhibitors are selective in that inhibition of sGC, NOS and the CYP isoforms 3A1/3A2 and CYP2E1 were not observed in vitro.

Applicants' invention includes small-molecule inhibitors that bind specifically to the apoprotein (i.e., protein not bound to heme) rather than compounds that coordinate to the heme iron, and thus the selectivity toward HO can be increased. This approach, combined with the dramatic difference in active site volume between the bacterial nm-HO and pa-HO versus the mammalian enzymes has been shown to be effective in the present invention, where the eight compounds (FIG. 2) have been shown to bind to HO in vitro.

Figure 6:
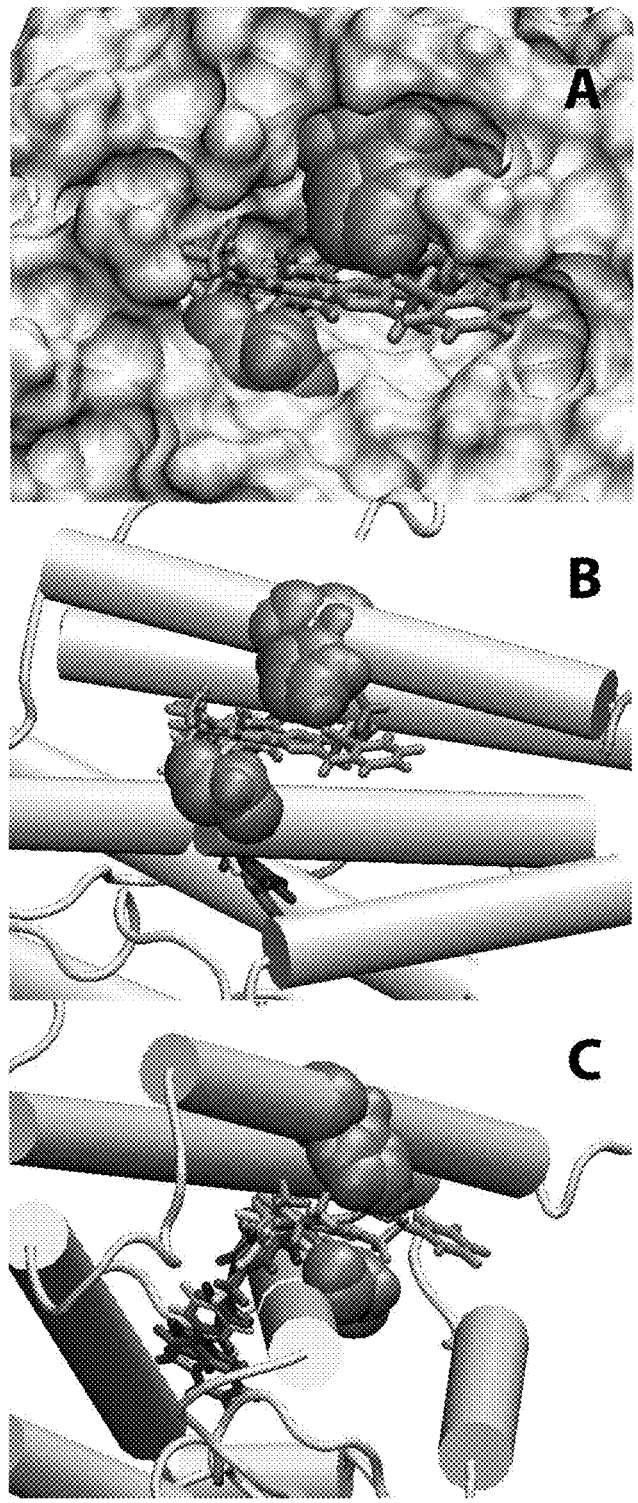
FIG. 6. Images of selected active compounds bound to the heme oxygenase conformation from the 19,965 ps snapshot of the trajectory.
Compounds shown include 1, 2, 5, 7 and 8 of FIG. 2 and are those that were selected in the secondary screen based on the most favorable interaction energy. Residues His-23 and Gly-116 are shown as purple space filling representations and the 6 compounds are shown in licorice format with each compound assigned a separate color.
A) Surface representation of heme oxygenase viewing directly into the heme binding pocket;
B) Cartoon representation in an orientation similar to that of A with the scale decreased and
C) cartoon representation that is an approximately 90° rotation of the view in B.
Figure 7:
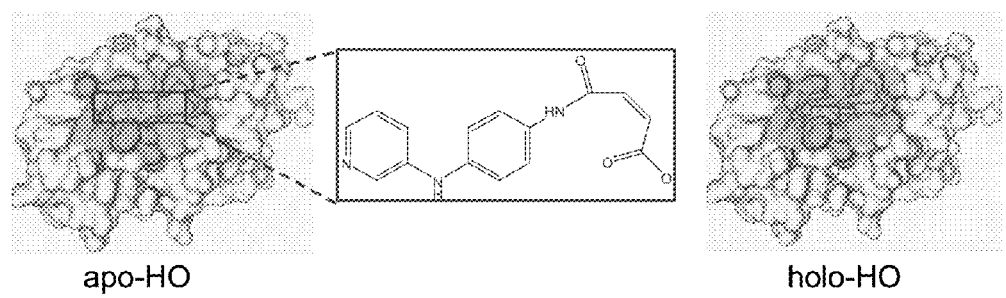
FIG. 7. Schematic representation of the proposed binding site of inhibitors directed toward the bacterial heme oxygenases.

The predicted orientations of active compounds 1, 2, 5, 7 and 8 of FIG. 2 bound to apo nm-HO are shown in FIG. 6. Analysis of FIG. 6A shows two of the compounds to span the heme binding pocket, residing between His-23 and Gly-116, taking advantage of a range of interactions within the binding pocket. Several of the compounds bind in a region in the back of the heme pocket previously identified in several bacterial crystal structure(s). The extent to which these compounds sample that region is particularly clear in FIG. 6C where it is seen that the compounds wrap around the proximal helix, binding well below the heme binding region. Binding to this region is particularly interesting in that it may facilitate the identification of compounds that bind specifically to HO's without having significant interactions with other heme binding proteins that do not contain such a pocket. Furthermore, this region of the pocket is significantly larger in the mammalian HO enzymes where a pronounced channel runs from the back of the cavity to the surface of the protein[28]. The lead compounds with this binding site may be a means of identifying inhibitors that are selective toward the bacterial[27, 29] versus the human HO[28].

The compounds of the present invention are the first compounds developed to target bacterial HOs, and the apo-form of the enzyme. The compounds and methods of the present invention compounds provide a novel step in the development of antimicrobials that specifically target heme utilization as a mechanism of antimicrobial drug development. The compounds and methods of the present invention compounds represent a new drug that is not covered by any of the current antimicrobial classes.

Clustering of the lead compounds may provide a framework for drug development.

Several of the compounds were shown to bind to both pa-HO and nm-HO with binding affinities ($K_D$) in the micromolar range (Table 1 and FIG. 2). The affinity of heme for the bacterial HO's ranges from 1-5 µM[25, 51-53], however, it should be noted that in vivo heme is delivered to HO by a heme-trafficking protein indicating "free" heme binding affinities may not be relevant to the in vivo mechanism of heme inhibition[54, 55]. Further biological screening of the inhibitors revealed that in addition to in vitro binding to the HO proteins, many of the inhibitors also inhibited α-biliverdin production in *E. coli* cells expressing nm-HO (Table 1 and FIG. 3). The decrease in biliverdin production in cells expressing nm-HO was confirmed on biliverdin extraction and HPLC analysis of the product compared with that of cells in the absence of the inhibitor (FIG. 3B). *E. coli* expressing nm-HO were not subjected to iron-restriction and therefore no significant decrease in cell density was observed between the untreated and treated cell. This data taken together suggests that the compounds are taken up by the bacterial cell and specifically target the HO enzyme as judged by decreased biliverdin formation.

The ability of the selected compounds to accumulate in cells and to inhibit endogenous pa-HO was further evaluated in the laboratory strain MPA01. The initial screening of Compounds 1-7 of FIG. 2 all indicated some degree of inhibition in the presence of heme as the sole source of iron (data not shown). The only exception was Compound 8 of FIG. 2 which was toxic to the cells at concentrations above 250 µM (data not shown). Further analysis of Compounds 2 and 3 of FIG. 2 confirmed that the inhibition was specific to heme utilization and did not disrupt iron uptake via the siderophore-uptake pathways when iron was supplied in the form of FeIII-pyoverdine (FIG. 4A-C). One key factor in the present invention is the ability of the inhibitors, presumably by passive diffusion, to cross the bacterial cell membrane and directly target the HO protein.

Although the in vitro $K_D$ values were in the 5-30 µM range and the growth rates of MPA01 were inhibited at values greater than 250 µM, it is evident that the concentration of Compounds 2, 3 and 5 of FIG. 2 being reached within the cell are sufficient to compete with exogenously acquired heme for binding to HO.

Additionally, it was noted that there was no significant difference in HO protein expression levels between cultures grown in the presence of the inhibitor and those in the absence of inhibitor. The iron-restricted conditions employed in the current studies mimic the iron-limited environment encountered by the organism on colonization and infection. Thus, the current data suggests that in an environment where heme may be the primary source of iron the ability of the organism to establish an infection may be compromised. Indeed, it has recently been shown that for *Staphylococcus aureus* heme is the preferred source of iron during the initial stages of infection[56]. However, while the levels of heme available to pathogens under different physiological conditions and disease states is not known, the high-affinity outer-membrane receptors allow bacteria to survive in environments where the heme may be extremely low. This is evident in the case of *Haemophilus influenzae* and *Porphyromonas gingivalis*, both of which have an absolute requirement for heme, as they lack the heme biosynthesis genes, and yet can successfully colonize the naso- and oro-pharynx, respectively[57, 58]. Therefore, even in environments where heme is extremely low, a slight degree of hemolysis induced by the action of secreted virulence factors would significantly increase the levels of hemoglobin available to the bacterial pathogen. In *P. aeruginosa* secretion of the redox active pyocyanin virulence factor contributes to tissue damage and inflammation, increasing the availability of heme to the bacteria[1-3, 59]. Indeed, the levels of human HO-1 in the lungs of *P. aeruginosa* infected CF patients has been shown to be up-regulated in a cyto-protective response to bacterial induced oxidative stress and inflammation, highlighting the host's response in restricting access of the pathogen to heme[60]. Therefore, by effectively eliminating or restricting the ability of the pathogen to acquire and utilize heme, significant reduction in the virulence of the organism may be achieved by Applicants' invention.

Examples

In Silico Database Screening

Identification of putative inhibitors was performed by screening of a virtual database of over 800,000 compounds[36] against the heme binding site of nm-HO. The virtual database represents a collection of low molecular weight compounds that are commercially available and predominately have drug like characteristics[61]. This database has been used in the laboratory of Dr. Alexander D. MacKerrel for the identification of inhibitors of several proteins[35, 40, 41, 62]. To obtain multiple conformations of the heme binding site suitable for database screening, the apo form of the protein (i.e., without the heme) was subjected to an MD simulation; from this simulation three conformations which had significant solvent accessibilities of the heme binding site were selected for the database screening. MD simulations and related calculations were performed with the program CHARMM[63, 64] using the all-hydrogen protein force field parameters[65] including the CMAP enhancement[66, 67], and the TIP3P water model[68]. The CRYSTAL module[69] in CHARMM was used for the periodic boundary conditions, and electrostatic interactions were treated using the Particle Mesh Ewald method[70]. Real space electrostatic and Lennard-Jones cutoffs were 12 Å with a force switch smoothing function[71] from 10 to 12 Å for the Lennard-Jones term. The non-bond list was maintained to 12

Å and heuristically updated. An integration time step of 2 fs, a temperature of 300 K, and SHAKE to constrain the covalent bonds involving hydrogen atoms[72] were used during the NPT simulation, which were performed using the Langevin Piston algorithm[73].

Preparation of the protein for the simulation was initiated by obtaining the 3D structure of nm-HO complexed with heme from the Protein Databank (PDB)[74] (PDB identifier: 1P3T)[26] the amino acid numbering herein represents the full length sequence of the protein. The porphyrin moiety was removed and the resulting structure (3114 atoms) was solvated. Solvation was performed by overlaying the protein with a pre-equilibrated box of water containing sodium of dimensions 70.5×64.6×60.4 Å, which is approximately 10 Å larger than the protein in all directions. All water or sodium ions within 2.8 Å of the protein non-hydrogen atoms were then deleted. Energy minimization of the solvent molecules was performed for 300 Steepest-Descent (SD) steps in the presence of periodic boundary conditions with the protein atoms harmonically restrained. The system was then equilibrated via a 20 ps NVT simulation[75] with the harmonic restraints maintained on the protein. This was followed by initiation of the production NPT simulation. This simulation was extended for 20 ns with the initial 1 ns considered equilibration and with coordinates from the trajectory saved every 5 ps. Conformations from the MD simulations were then selected for database screening as described in the Results section.

Primary database screening was performed on a single nm-HO conformation corresponding to the 5575 ps snapshot from the MD simulation. Gasteiger charges were added to the protein using MOE (MOE; Chemical Computing Group Inc.: Montreal, Quebec, Canada, 2002). Docking calculations were carried out with the DOCK program[76] using flexible ligands based on the anchored search method[77] with posing based on the total ligand-protein interaction energy. The solvent-accessible surface[78] was calculated with the program DMS from the UCSF MIDAS package[79] using a probe radius of 1.4 Å. Sphere sets, required for initial placement of the ligand during database screening, were calculated with the program SPHGEN, part of the DOCK package. Spheres that lay inside of the binding pocket on each side of residue His-23 were selected for the search as each site may display separate binding affinities and specificities. Ligand-protein interaction energies were approximated by the sum of the electrostatic and van der Waals attractive components as calculated by the GRID method[80] implemented in DOCK using default values. The GRID box dimensions were 30×30×36 Å$^3$ centered on a point placed approximately in the center of the binding pocket. During docking the posing of the ligands was based on the total interaction energy with the target protein; however, for primary screening scoring was based on the attractive vdW interaction energy, as described in the results. Scoring for secondary screening used the total interaction energy.

The following operational parameters were applied in the docking runs. Database screening initially selected compounds containing 10 or less rotatable bonds and between 10 and 40 non-hydrogen atoms. Ligand flexibility was considered by dividing each compound into a collection of non-overlapping rigid segments. Individual rigid segments with five or more heavy atoms (e.g., aromatic rings) were selected as "anchors". Each anchor was individually docked into the binding site in 200 separate orientations, based on different overlap of the anchor atoms with the sphere set, and was then energy-minimized. The remainder of each molecule was built onto the anchor in a stepwise fashion until the entire molecule was constructed, with each step corresponding to a rotatable bond. At each successive step the dihedral angle about the rotatable bond, which connected the new segment to the previously constructed portion of the molecule, was sampled in 10° increments and the lowest energy conformation was then selected. During the build-up process, selected conformers were removed on both the basis of energetic considerations and maximization of diversity of the conformations being sampled, as previously described[77, 81]. The ligand orientation with the most favorable interaction energy was selected.

Previous studies in our laboratory have shown that the DOCK energy score is biased toward the selection of high molecular weight compounds because of the contribution of the compound size to the energy score[36]. Such biasing behavior was observed to depend on the shape and chemical properties of the binding pocket. Hence, a computationally efficient procedure was developed in which the energy score is normalized by the number of heavy atoms N in each respective compound or by a selected power of N. This normalization approach shifts the molecular weight distribution of the selected compounds into better agreement with that of the entire database.

Compounds selected from the primary screen were subjected to a secondary screen. This screen involved a more rigorous minimization that included simultaneous energy minimization of the anchor fragment during the iterative build-up procedure. In addition, three additional conformations of the protein obtained from snapshots at 16,405, 16,805 and 19,965 ps of the MD simulations were used, such that each compound was docked individually against four conformations with the best score from the four runs used for final ranking of that compound. From the secondary screen 1000 compounds were selected based on the total interaction energy using $N^{3/5}$ normalization.

Selection of the final compounds for experimental assay involved maximizing the chemical diversity of the compounds as well as consideration of their physical properties. This was performed by dividing the 1000 compounds from the secondary docking into chemically dissimilar clusters by applying the Tanimoto similarity indexes[82] using the program MOE. The clustering procedure started with the calculation of the molecular fingerprints, followed by the calculation of the pairwise Tanimoto similarity matrix A(i,j) containing the similarity metric between the molecular fingerprints of compounds i and j. From A(i,j), a binary matrix B was created such that B(i,j) has the value 1 if A(i,j) is equal to or greater than S, or 0 otherwise, where S is a user selected similarity threshold that determines if two compounds are defined as similar. The rows of the B matrix were then treated as fingerprints, where two molecules belong to the same cluster if the Tanimoto coefficient of their corresponding rows in B is greater than or equal to T, a user selected overlap threshold. This results in two molecules being clustered together if they are similar to the same set of molecules. In the present study the similarity threshold was set to 70% and the overlap threshold was set to 40%. Compounds for biological assay were selected from the dissimilar sets. This was performed by individually analyzing the clusters and selecting compounds from each cluster based on Lipinski's rule of 5[83], including solubility (ClogP≦5), molecular weight (≦500 Da) and the number of the hydrogen bond donors (≦5) and acceptors (≦10). In addition, the chemical stability was considered. From the 1,000 compounds a subset of 153 chemically diverse molecules were selected for biological assay and purchased from ChemBridge Corporation, San Diego, Calif.; ChemDiv Inc., San Diego, Calif.; Maybridge, Cornwall UK; and Specs, Cumberland, Md.

Bacterial Strains, Plasmids and Media.

*Pseudomonas aeruginosa* MPAO1 was obtained from the University of Washington, Genome Center, Seattle, Wash. The pa-HO and nm-HO genes cloned into pET21a were transformed into *E. coli* strain BL21 (DE3) pLysS [F⁻ ompT hsdS$_B$ (r$_B^-$m$_B^-$) gal dcm (DE3)] for protein expression as previously described[25, 53]. Luria Bertani (LB) broth was used for growth and maintenance of *E. coli* strains in the presence of ampicillin, 100 µg/ml. MinA minimal medium plates were used for growth and maintenance of the MPA01 strain. Succinate minimal (SM) media (pH 7.0) was used for all growth studies of *P. aeruginosa*.

General Methods.

A stock solution of hemoglobin was prepared in SM media (pH 7.0). Pyoverdine was purified as described by Dr. Jean-Marie Meyer, Department de Genetique Moleculaire, Denomique et Micorbiologie, Strasbourg, France. A single colony of MPAO1 was grown in 10 ml LB-media for 16 hrs. The culture was pelleted by centrifugation (4,000 rpm for 10 min at 4° C.) and re-suspended in 1 ml of SM media. A 1:1000 dilution was made into 1 L of SM and grown for 24 hrs. Subsequently, the culture was harvested by centrifugation in a Beckman JA-10 rotor (10,000 rpm for 15 min) at 4° C. and the resulting supernatant was acidified to pH 6.0. The acidified supernatant was applied to an Amberlite XAD-4 (Sigma) column (2.5×10 cm) previously washed with 50% methanol (MeOH) and extensively equilibrated with double distilled water. The column was washed with 3 volumes of water, and the pigment was eluted in 50% MeOH. The eluate was evaporated to dryness under vacuum and re-suspended in 5 ml of water. The concentration of iron-free pyoverdine (1:1000) was determined in 0.5 M acetic acid-sodium acetate buffer, pH 5.0 from the extinction coefficient at 340 nm of $\epsilon_{max}=16,500$ M⁻¹ cm⁻¹ [184].

A stock solution of FeCl₃ (4.5 mM) was prepared in 0.5 M sodium citrate for reconstitution of the holo-pyoverdine. A 2.5 µM stock solution of apo-pyoverdine was reconstituted with FeCl₃ at a 1:1 ratio to yield the resulting holo-pyoverdine. All inhibitors were prepared by solubilization in dimethyl sulfoxide (DMSO) and added directly to the cultures or purified protein in the concentrations stated. MPA01 growth inhibition assays were carried out in SM media with a range of inhibitor concentrations from 250-1500 µM.

Protein Purification.

The wild-type apo-nm-HO and pa-HO proteins were purified by the previously described procedures[25, 53]. Following purification of the apo-proteins residual biliverdin was removed by passage of the protein over a PBE 94® chromatofocusing column (1×20 cm) equilibrated in 0.025 M imidazole-HCl (pH 7.4). The apo-protein was eluted with a pH gradient from 7-4 with Polybuffer 74-HCl® (pH 4.0). The proteins eluted at their respective pI's and the Polybuffer was removed by ammonium sulfate precipitation and dialysis against 20 mM Tris-HCl (pH 7.5).

Measurement of the Binding Affinities (K$_D$) of the Selected Compounds.

The binding of the compounds to apo-nm-HO and apo-pa-HO were obtained by fluorescence titrations. Measurements were made on an ISS PC-1 spectrofluorimeter configured in the L format. Full excitation/emission spectra were recorded for each compound to determine the intrinsic fluorescence properties of the selected inhibitors. All experiments with either apo-nm-HO or apo-pa-HO were carried out in 20 mM Tris-HCl (pH 7.5). The titrations were performed by addition of increasing concentrations of the selected compound (0.05-500 µM) while maintaining the apo-nm-HO and apo-pa-HO protein concentrations at 1 µM. The optimal excitation wavelength for the apo-proteins was 295 nm and the fluorescence emission was monitored from 300 to 500 nm. The dissociation constants (K$_D$) were calculated from reciprocal plots of 1/ΔA vs 1/[I] where the decrease in fluorescence, ΔA, at the maximum emission (330 nm), represents the fraction of occupied binding sites, and [I] the concentration of the inhibitor. The slope of the curve equals the K$_D$ as described by the equilibrium equation (1):

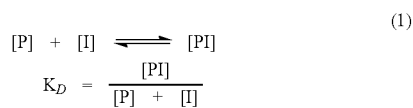

$$[P] + [I] \rightleftharpoons [PI] \qquad (1)$$
$$K_D = \frac{[PI]}{[P] + [I]}$$

The binding affinities (K$_D$) of each compound for both nm-HO and pa-HO were measured and calculated based on an average of three separate experiments.

Biliverdin Detection in an *E. coli* Expression System.

The nm-HO was expressed with modification of a previously reported method[53]. A single colony of freshly transformed *E. coli* BL21 (DE3) cells was cultured overnight in 10 ml of Luria-Bertani (LB) medium containing 100 µg/ml of ampicillin. The leaky expression of nm-HO in *E. coli* over a 16 hour period gives rise to green pigmentation in the pellet as a result of heme turnover and α-biliverdin production. The cells following overnight growth in the absence or presence of Compound 3 of FIG. 2 (1500 µM) were harvested by centrifugation (10,000 g for 15 min). The pelleted cells were lysed in 50 mM Tris-HCl buffer (pH 7.4) containing 1 mM EDTA, 2 mM desferroxamine and 1 mM PMSF, and the lysate had added to it purified (50 µM) β/δ-biliverdin as an internal standard. The soluble fraction was then extracted into chloroform and the organic layer was washed three times with water and dried down. The dried residue was resuspended in 500 µl methanol containing 4% sulfuric acid and incubated for 6-8 hours. The resulting biliverdin dimethyl esters were washed with water (×3) dried down and analyzed by HPLC as described previously[85].

Growth inhibition of *Pseudomonas aeruginosa* MPA01 in the Presence of Selected Compounds.

A 15 ml culture of MPAO1 was grown from a single colony for 8 hrs at 37° C. The culture was diluted in SM-media to an OD$_{600}$ of 0.05. A 96-well plate assay was set up with 200 µl MPAO1 cultures in SM-media either alone or containing 250-1500 µM compound, or 25 µM hemoglobin±250-1500 µM compound, or 40 µM holo-pyoverdine±250-1500 µM compound where indicated. The cultures were incubated for 10 hrs at 37° C. with aeration, at which point the OD$_{600}$ for all wells was recorded on a SpectraMax Plus 96-well plate reader (Molecular Devices Corporation).

To determine the growth characteristics of MPAO1, in the presence of compound, through log phase and entering early stationary phase, a 15 ml overnight culture was set up from a single colony of MPA01 in SM-media at 37° C. with shaking at 200 rpm. The following day the overnight culture was diluted to an OD$_{600}$ of 0.05 in 12 ml SM-media containing 500 µM compound, or 25 µM hemoglobin±500 µM compound or 40 µM holo-pyoverdine±500 µM compound where indicated. The cultures were grown with aeration at 37° C. and the OD$_{600}$ was measured every hour over a period of 12 hrs. At 0, 6, and 10 hour time points, 2 ml samples were collected for subsequent Western blot analysis. The pellets were lysed with approximately 350 µl of lysis buffer containing 50 mM Tris, 1 mM EDTA and 1 mM PMSF. The samples were incubated on ice for 15 minutes, sonicated briefly, and spun at 4° C. for 10 minutes to remove cell debris. The total protein concentration was determined by Bradford assay[86] (Bio-Rad Laboratories, Hercules, Calif.). For each time point a total of 5 μg of protein in a final volume of 15 μl was loaded on to a SDS-PAGE gel 12.5%. The expression of iron-regulated heme oxygenase, pa-HO was confirmed by Western Blotting as previously described[87] using a polyclonal antibody raised against pa-HO (Covance Research, Denver, Pa.).

REFERENCES

1. Currie, A. J.; Speert, D. P.; Davidson, D. J. *Pseudomonas aeruginosa*: role in the pathogenesis of the CF lung lesion. *Semin Respir Crit. Care Med* 2003, 24, 671-80.
2. Heijerman, H. Infection and inflammation in cystic fibrosis: A short review. *J Cyst Fibros* 2005, 4 Suppl 2, 3-5.
3. Elkin, S.; Geddes, D. Pseudomonal infection in cystic fibrosis: the battle continues. *Expert Rev Anti Infect Ther* 2003, 1, 609-18.
4. Oliveira, A. L.; de Souza, M.; Carvalho-Dias, V. M.; Ruiz, M. A.; Silla, L.; Tanaka, P. Y.; Simoes, B. P.; Trabasso, P.; Seber, A.; Lotfi, C. J.; Zanichelli, M. A.; Araujo, V. R.; Godoy, C.; Maiolino, A.; Urakawa, P.; Cunha, C. A.; de Souza, C. A.; Pasquini, R.; Nucci, M. Epidemiology of bacteremia and factors associated with multi-drug-resistant gram-negative bacteremia in hematopoietic stem cell transplant recipients. *Bone Marrow Transplant* 2007.
5. Braun, V. Iron uptake mechanisms and their regulation in pathogenic bacteria. *Int J Med Microbiol* 2001, 291, 67-79.
6. Braun, V. Bacterial iron transport related to virulence. *Contrib Microbiol* 2005, 12, 210-33.
7. Payne, S. M. Iron acquisition in microbial pathogenesis. *Trends Microbiol* 1993, 1, 66-9.
8. Wandersman, C.; Delepelaire, P. Bacterial iron sources: from siderophores to hemophores. *Annu Rev Microbiol* 2004, 58, 611-47.
9. Wandersman, C.; Stojiljkovic, I. Bacterial heme sources: the role of heme, hemoprotein receptors and hemophores. *Curr Opin Microbiol* 2000, 3, 215-20.
10. Ortiz de Montellano, P. R.; Wilks, A. Heme Oxygenase Structure and mechanism. *Advances in Inorganic Chemistry* 2000, 51, 359-402.
11. Wilks, A. Heme oxygenase: evolution, structure, and mechanism. *Antioxid Redox Signal* 2002, 4, 603-14.
12. Zhu, W.; Hunt, D. J.; Richardson, A. R.; Stojiljkovic, I. Use of heme compounds as iron sources by pathogenic neisseriae requires the product of the hemO gene. *J Bacteriol* 2000, 182, 439-47.
13. Sanders, J. D.; Cope, L. D.; Hansen, E. J. Identification of a locus involved in the utilization of iron by *Haemophilus influenzae*. *Infect Immun* 1994, 62, 4515-25.
14. Henderson, D. P.; Payne, S. M. Characterization of the *Vibrio cholerae* outer membrane heme transport protein HutA: sequence of the gene, regulation of expression, and homology to the family of TonB-dependent proteins. *J Bacteriol* 1994, 176, 3269-77.
15. Henderson, D. P.; Payne, S. M. *Vibrio cholerae* iron transport systems: roles of heme and siderophore iron transport in virulence and identification of a gene associated with multiple iron transport systems. *Infect Immun* 1994, 62, 5120-5.
16. Mills, M.; Payne, S. M. Genetics and regulation of heme iron transport in *Shigella dysenteriae* and detection of an analogous system in *Escherichia coli* O157:H7. *J Bacteriol* 1995, 177, 3004-9.
17. Mills, M.; Payne, S. M. Identification of shuA, the gene encoding the heme receptor of *Shigella dysenteriae*, and analysis of invasion and intracellular multiplication of a shuA mutant. *Infect Immun* 1997, 65, 5358-63.
18. Otto, B. R.; Verweij-van Vught, A. M.; MacLaren, D. M. Transferrins and heme-compounds as iron sources for pathogenic bacteria. *Crit. Rev Microbiol* 1992, 18, 217-33.
19. Lewis, L. A.; Gipson, M.; Hartman, K.; Ownbey, T.; Vaughn, J.; Dyer, D. W. Phase variation of HpuAB and HmbR, two distinct haemoglobin receptors of *Neisseria meningitidis* DNM2. *Mol Microbiol* 1999, 32, 977-89.
20. Ochsner, U. A.; Johnson, Z.; Vasil, M. L. Genetics and regulation of two distinct haem-uptake systems, phu and has, in *Pseudomonas aeruginosa*. *Microbiology* 2000, 146 (Pt 1), 185-98.
21. Hall-Stoodley, L.; Costerton, J. W.; Stoodley, P. Bacterial biofilms: from the natural environment to infectious diseases. *Nat Rev Microbiol* 2004, 2, 95-108.
22. Parsek, M. R.; Singh, P. K. Bacterial biofilms: an emerging link to disease pathogenesis. *Annu Rev Microbiol* 2003, 57, 677-701.
23. Costerton, J. W. Cystic fibrosis pathogenesis and the role of biofilms in persistent infection. *Trends Microbiol* 2001, 9, 50-2.
24. Costerton, J. W.; Stewart, P. S.; Greenberg, E. P. Bacterial biofilms: a common cause of persistent infections. *Science* 1999, 284, 1318-22.
25. Ratliff, M.; Zhu, W.; Deshmukh, R.; Wilks, A.; Stojiljkovic, I. Homologues of Neisserial Heme Oxygenase in Gram-Negative Bacteria: Degradation of Heme by the Product of the pigA Gene of *Pseudomonas aeruginosa*. *J Bacteriol* 2001, 183, 6394-403.
26. Friedman, J.; Lad, L.; Deshmukh, R.; Li, H.; Wilks, A.; Poulos, T. L. Crystal structures of the NO- and CO-bound heme oxygenase from *Neisseriae meningitidis*. Implications for O2 activation. *J Biol Chem* 2003, 278, 34654-9.
27. Friedman, J.; Lad, L.; Li, H.; Wilks, A.; Poulos, T. L. Structural basis for novel delta-regioselective heme oxygenation in the opportunistic pathogen *Pseudomonas aeruginosa*. *Biochemistry* 2004, 43, 5239-45.
28. Schuller, D. J.; Wilks, A.; Ortiz de Montellano, P. R.; Poulos, T. L. Crystal structure of human heme oxygenase-1. *Nat Struct Biol* 1999, 6, 860-7.
29. Schuller, D. J.; Zhu, W.; Stojiljkovic, I.; Wilks, A.; Poulos, T. L. Crystal structure of heme oxygenase from the gram-negative pathogen *Neisseria meningitidis* and a comparison with mammalian heme oxygenase-1. *Biochemistry* 2001, 40, 11552-8.
30. Braun, V.; Braun, M. Active transport of iron and siderophore antibiotics. *Curr Opin Microbiol* 2002, 5, 194-201.
31. Gohlke, H.; Klebe, G. Statistical potentials and scoring functions applied to protein-ligand binding. *Curr Opin Struct Biol* 2001, 11, 231-5.
32. Leach, A. R.; Shoichet, B. K.; Peishoff, C. E. Prediction of protein-ligand interactions. Docking and scoring: Successes and gaps. *Journal of Medicinal Chemistry* 2006, 49, 5851-5855.
33. Chen, I.-J.; Neamati, N.; MacKerell, A. D., Jr. Structure-Based Inhibitor Design Targeting HIV-1 Integrase. *Current Drug Targets—Infectious Disorders* 2002, 2, 217-234.
34. Markowitz, J.; Chen, I.; Gitti, R.; Baldisseri, D. M.; Pan, Y.; Udan, R.; Carrier, F.; MacKerell, A. D., Jr.; Weber, D. J. Identification and Characterization of Small Molecule Inhibitors of the Calcium-Dependent S100B-p53 Tumor Suppressor Interaction. *J Med Chem* 2004, 47, 5085-5093.
35. Hancock, C. N.; Macias, A. T.; Lee, E. K.; Yu, S. Y.; MacKerell, A. D., Jr.; Shapiro, P. Identification of novel extracellular signal-regulated kinase (ERK) docking domain inhibitors. *J. Med. Chem.* 2005, 48, 4586-4595.

36. Pan, Y.; Huang, N.; Cho, S.; MacKerell, A. D., Jr. Consideration of Molecular Weight During Compound Selection in Virtual Target-Based Database Screening. *J. Chem. Inf. Comp. Sci.* 2003, 43, 267-272.
37. Teague, S. J.; Davis, A. M.; Leeson, P. D.; Oprea, T. The Design of Leadlike Combinatorial Libraries. *Angew Chem Int Ed Engl* 1999, 38, 3743-3748.
38. Oprea, T. I. Property distribution of drug-related chemical databases. *J. Comput.-Aided Mol. Des.* 2000, 14, 251-264.
39. Oprea, T. I.; Davis, A. M.; Teague, S. J.; Leeson, P. D. Is There a Difference between Leads and Drugs? A Historical Perspective. *J. Chem. Inf. Comp. Sci.* 2001, 41, 1308-1315.
40. Huang, N.; Nagarsekar, A.; Xia, G.; Hayashi, J.; MacKerell Jr., A. D. Identification of Inhibitors Targeting the pY+3 Binding Site of the Tyrosine Kinase p53lck SH2 domain. *J. Med. Chem.* 2004, 47, 3502-3511.
41. Chen, F.; Hancock, C. N.; Macias, A. T.; Joh, J.; Still, K.; Zhong, S.; MacKerell, A. D., Jr.; Shapiro, P. Characterization of ATP-independent ERK inhibitors identified through in silico analysis of the active ERK2 structure. *Bioorg Med Chem Lett* 2006, 16, 6281-6287.
42. Drummond, G. S.; Kappas, A. Prevention of neonatal hyperbilirubinemia by tin protoporphyrin IX, a potent competitive inhibitor of heme oxidation. *Proc Natl Acad Sci USA* 1981, 78, 6466-70.
43. Vreman, H. J.; Cipkala, D. A.; Stevenson, D. K. Characterization of porphyrin heme oxygenase inhibitors. *Can J Physiol Pharmacol* 1996, 74, 278-85.
44. Vreman, H. J.; Ekstrand, B. C.; Stevenson, D. K. Selection of metalloporphyrin heme oxygenase inhibitors based on potency and photoreactivity. *Pediatr Res* 1993, 33, 195-200.
45. Vreman, H. J.; Rodgers, P. A.; Stevenson, D. K. Zinc protoporphyrin administration for suppression of increased bilirubin production by iatrogenic hemolysis in rhesus neonates. *J Pediatr* 1990, 117, 292-7.
46. Trakshel, G. M.; Sluss, P. M.; Maines, M. D. Comparative effects of tin- and zinc-protoporphyrin on steroidogenesis: tin-protoporphyrin is a potent inhibitor of cytochrome P-450-dependent activities in the rat adrenals. *Pediatr Res* 1992, 31, 196-201.
47. Luo, D.; Vincent, S. R. Metalloporphyrins inhibit nitric oxide-dependent cGMP formation in vivo. *Eur J Pharmacol* 1994, 267, 263-7.
48. Glaum, S. R.; Miller, R. J. Zinc protoporphyrin-IX blocks the effects of metabotropic glutamate receptor activation in the rat nucleus tractus solitarii. *Mol Pharmacol* 1993, 43, 965-9.
49. Vlahakis, J. Z.; Kinobe, R. T.; Bowers, R. J.; Brien, J. F.; Nakatsu, K.; Szarek, W. A. Imidazole-dioxolane compounds as isozyme-selective heme oxygenase inhibitors. *J Med Chem* 2006, 49, 4437-41.
50. Walker, K. A.; Kertesz, D. J.; Rotstein, D. M.; Swinney, D. C.; Berry, P. W.; So, O. Y.; Webb, A. S.; Watson, D. M.; Mak, A. Y.; Burton, P. M.; et al. Selective inhibition of mammalian lanosterol 14 alpha-demethylase: a possible strategy for cholesterol lowering. *J Med Chem* 1993, 36, 2235-7.
51. Chu, G. C.; Katakura, K.; Zhang, X.; Yoshida, T.; Ikeda-Saito, M. Heme degradation as catalyzed by a recombinant bacterial heme oxygenase (Hmu O) from *Corynebacterium diphtheriae*. *J Biol Chem* 1999, 274, 21319-25.
52. Wilks, A.; Torpey, J.; Ortiz de Montellano, P. R. Heme oxygenase (HO-1). Evidence for electrophilic oxygen addition to the porphyrin ring in the formation of alpha-meso-hydroxyheme. *J Biol Chem* 1994, 269, 29553-6.
53. Zhu, W.; Wilks, A.; Stojiljkovic, I. Degradation of Heme in Gram-Negative Bacteria: the Product of the hemO Gene of Neisseriae Is a Heme Oxygenase. *J Bacteriol* 2000, 182, 6783-6790.
54. Lansky, I. B.; Lukat-Rodgers, G. S.; Block, D.; Rodgers, K. R.; Ratliff, M.; Wilks, A. The Cytoplasmic Heme-binding Protein (PhuS) from the Heme Uptake System of *Pseudomonas aeruginosa* Is an Intracellular Heme-trafficking Protein to the {delta}-Regioselective Heme Oxygenase. *J Biol Chem* 2006, 281, 13652-62.
55. Bhakta, M. N.; Wilks, A. The Mechanism of Heme Transfer from the Cytoplasmic Heme Binding Protein PhuS to the delta-Regioselective Heme Oxygenase of *Pseudomonas aeruginosa*. *Biochemistry* 2006, 45, 11642-9.
56. Skaar, E. P.; Humayun, M.; Bae, T.; DeBord, K. L.; Schneewind, O. Iron-source preference of *Staphylococcus aureus* infections. *Science* 2004, 305, 1626-8.
57. Cope, L. D.; Yogev, R.; Muller-Eberhard, U.; Hansen, E. J. A gene cluster involved in the utilization of both free heme and heme:hemopexin by *Haemophilus influenzae* type b. *J Bacteriol* 1995, 177, 2644-53.
58. Olczak, T.; Simpson, W.; Liu, X.; Genco, C. A. Iron and heme utilization in *Porphyromonas gingivalis*. *FEMS Microbiol Rev* 2005, 29, 119-44.
59. Ran, H.; Hassett, D. J.; Lau, G. W. Human targets of *Pseudomonas aeruginosa* pyocyanin. *Proc Natl Acad Sci USA* 2003, 100, 14315-20.
60. Zhou, H.; Lu, F.; Latham, C.; Zander, D. S.; Visner, G. A. Heme oxygenase-1 expression in human lungs with cystic fibrosis and cytoprotective effects against *Pseudomonas aeruginosa* in vitro. *Am J Respir Crit. Care Med* 2004, 170, 633-40.
61. Sirois, S.; Hatzakis, G.; Wei, D.; Du, Q.; Chou, K. C. Assessment of chemical libraries for their druggability. *Comput. Chem. Biol.* 2005, 29, 55-67.
62. Markowitz, J.; MacKerell, A. D., Jr.; Carrier, F.; Charpentier, T. H.; Weber, D. J. Design of Inhibitors of S100B. *Curr Top Med Chem* 2005, 5, 1093-1108.
63. Brooks, B. R.; Bruccoleri, R. E.; Olafson, B. D.; States, D. J.; Swaminathan, S.; Karplus, M. CHARMM: A Program for Macromolecular Energy, Minimization, and Dynamics Calculations. *J. Comput. Chem.* 1983, 4, 187-217.
64. MacKerell, A. D., Jr.; Brooks, B.; Brooks, C. L., III; Nilsson, L.; Roux, B.; Won, Y.; Karplus, M. CHARMM: The Energy Function and Its Paramerization with an Overview of the Program. In *Encyclopedia of Computational Chemistry*, Schleyer, P. v. R.; Allinger, N. L.; Clark, T.; Gasteiger, J.; Kollman, P. A.; Schaefer, H. F., III; Schreiner, P. R., Eds. John Wiley & Sons: Chichester, 1998; Vol. 1, pp 271-277.
65. MacKerell, A. D., Jr.; Bashford, D.; Bellott, M.; Dunbrack Jr., R. L.; Evanseck, J.; Field, M. J.; Fischer, S.; Gao, J.; Guo, H.; Ha, S.; Joseph, D.; Kuchnir, L.; Kuczera, K.; Lau, F. T. K.; Mattos, C.; Michnick, S.; Ngo, T.; Nguyen, D. T.; Prodhom, B.; Reiher, I., W. E.; Roux, B.; Schlenkrich, M.; Smith, J.; Stote, R.; Straub, J.; Watanabe, M.; Wiorkiewicz-Kuczera, J.; Yin, D.; Karplus, M. All-atom empirical potential for molecular modeling and dynamics studies of proteins. *J. Phys. Chem. B* 1998, 102, 3586-3616.
66. MacKerell, A. D., Jr.; Feig, M.; Brooks, C. L., III. Accurate treatment of protein backbone conformational energetics in empirical force fields. *J Am Chem Soc* 2004, 126, 698-699.
67. MacKerell, A. D., Jr.; Feig, M.; Brooks, C. L., III. Extending the treatment of backbone energetics in protein force fields: limitations of gas-phase quantum mechanics in reproducing protein conformational distributions in molecular dynamics simulations. *J. Comp. Chem.* 2004, 25, 1400-1415.
68. Jorgensen, W. L.; Chandrasekhar, J.; Madura, J. D.; Impey, R. W.; Klein, M. L. Comparison of Simple Potential Functions for Simulating Liquid Water. *Journal of Chemical Physics* 1983, 79, 926-935.

69. Field, M. J.; Karplus, M. *CRYSTAL Module of CHARMM*, 22; Harvard University: Cambridge, Mass., 1992.
70. Darden, T. A.; York, D.; Pedersen, L. G. Particle mesh Ewald: An N log(N) method for Ewald sums in large systems. *J. Chem. Phys.* 1993, 98, 10089-10092.
71. Steinbach, P. J.; Brooks, B. R. New Spherical-Cutoff Methods of Long-Range Forces in Macromolecular Simulations. *J. Comp. Chem.* 1994, 15, 667-683.
72. Ryckaert, J.-P.; Ciccotti, G.; Berendsen, H. J. C. Numerical Integration of the Cartesian Equations of Motion of a System with Constraints: Molecular Dynamics of n-Alkanes. *J. Comp. Physics* 1977, 23, 327-341.
73. Feller, S. E.; Zhang, Y.; Pastor, R. W.; Brooks, R. W. Constant Pressure Molecular Dynamics Simulation The Langevin Piston Method. *J. Chem. Phys.* 1995, 103, 4613-4621.
74. Berman, H. M.; Westbrook, J.; Feng, Z.; Gilliland, G.; Bhat, T. N.; Weissig, H.; Shindyalov, I. N.; Bourne, P. E. The Protein Data Bank. *Nucleic Acids Res* 2000, 28, 235-242.
75. Nosé, S. A unified formulation of the constant temperature molecular dynamics method. *J. Chem. Phys.* 1984, 81, 511-519.
76. Meng, E. C.; Shoichet, B. K.; Kuntz, I. D. Automated Docking with Grid-Based Energy Evaluation. *Journal of Computational Chemistry* 1992, 13, 505-524.
77. Leach, A. R.; Kuntz, I. D. Conformational analysis of flexible ligands in macromolecular receptor sites. *J. Comput. Chem.* 1992, 13, 730-748.
78. Connolly, M. L. Solvent-Accessible Surfaces of Proteins and Nucleic Acids. *Science* 1983, 221, 709-713.
79. Ferrin, T. E.; Huang, C. C.; Jarvis, L. E.; Langridge, R. The MIDAS display system. *J. Mol. Graphics.* 1988, 6, 13-27.
80. Goodford, P. J. A computational procedure for determining energetically favorable binding sites on biologically important macromolecules. *J. Med. Chem.* 1984, 28, 849-857.
81. Ewing, T. J. A.; Kuntz, I. D. Critical evaluation of search algorithms used in automated molecular docking. *J. Comput. Chem.* 1997, 18, 1175-1189.
82. Godden, J. W.; Stahura, F. L.; Bajorath, J. Variability of molecular descriptors in compound databases revealed by Shannon entropy calculations. *J Chem Inf Comput Sci* 2000, 40, 796-800.
83. Lipinski, C. A. Drug-like properties and the causes of poor solubility and poor permeability. *J. Pharmacol. Toxicol. Methods* 2000, 44, 235-249.
84. Demange, P.; Bateman, A.; Mertz, C.; Dell, A.; Piemont, Y.; Abdallah, M. A. Bacterial siderophores: structures of pyoverdins Pt, siderophores of *Pseudomonas tolaasii* NCPPB 2192, and pyoverdins Pf, siderophores of *Pseudomonas fluorescens* CCM 2798. Identification of an unusual natural amino acid. *Biochemistry* 1990, 29, 11041-51.
85. Sakamoto, H.; Omata, Y.; Adachi, Y.; Palmer, G.; Noguchi, M. Separation and identification of the regioisomers of verdoheme by reversed-phase ion-pair high-performance liquid chromatography, and characterization of their complexes with heme oxygenase. *J Inorg Biochem* 2000, 82, 113-21.
86. Bradford, M. M. A rapid and sensitive method for the quantitation of microgram quantities of protein utilizing the principle of protein-dye binding. *Anal Biochem* 1976, 72, 248-54.
87. Sambrook, J.; Fritsch, E. F.; Maniatis, T. Molecular Cloning: A Laboratory Manual, Cold Spring Harbor Laboratory, Cold Spring Harbor, N.Y. 1989.

All of the cited references herein are hereby specifically incorporated by reference in their entirety.

ABBREVIATIONS heme, iron-protoporphyrin IX in any oxidation state;
pa-HO, *Pseudomonas aeruginosa* heme oxygenase;
nm-HO, *Neisseria meningitidis* heme oxygenase;
MPAO1; *Pseudomonas aeruginosa* PAO1 strain;
sGC; soluble guanylate cyclase;
CYP, cytochrome P450;
NOS, Nitric oxide synthase;
CADD, computer aided drug design.

While the invention has been described with reference to certain particular embodiments thereof, the invention is not to be limited to the specific embodiments described and those skilled in the art will appreciate that various modifications may be made without departing from the spirit and scope of the invention.

TABLE 1

Binding affinities and inhibition of nm-HO activity by Compounds 1-8 of FIG. 2.

| | Binding affinity ($K_D$) (□M) | | E. coli assay biliverdin |
|---|---|---|---|
| Inhibitor | pa-HO | Nm-HO | pigmentation |
| 1 | 15.9 ± 1.1 | 12.2 ± 1.0 | − |
| 2 | 15.8 ± 1.0 | 14.1 ± 2.6 | − |
| 3 | 20.9 ± 1.8 | 15.6 ± 1.9 | − |
| 4 | 6.1 ± 0.5 | 20.9 ± 4.5 | − |
| 5 | 30 ± 2.8 | 22.9 ± 2.8 | − |
| 6 | 72.8 ± 5.3 | 28.8 ± 3.3 | + |
| 7 | 44.7 ± 6.9 | 33.5 ± 4.1 | + |
| 8 | 187.3 ± 14 | 239 ± 21 | Nd |

+ biliverdin observed in cell pellet
− biliverdin not observed
nd—not determined due to toxicity of the compound

TABLE 2

| Compound | Comments |
|---|---|
| 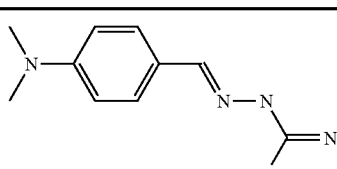<br>1; 5173151; 205 (MW); 2.00 (a10); 3.0 (d5); 3.77 (logP) | Alias: CB-5 Compound 5 in the manuscript.<br>fluorescence binding: yes<br>minimum inhibition conc: >160 ug/ml<br>NMR sat. transfer: yes, bind paHO<br>E. coli assay: white pellet<br>C. elegans assay: yes |

TABLE 2-continued

| Compound | Comments |
|---|---|
| 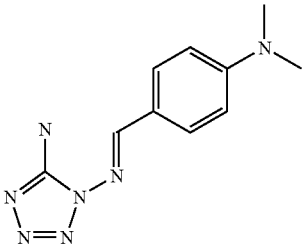 [SMILES: CN(C)c1ccc(/C=N/n2nnnc2N)cc1]<br>2; 0779-0005; 231; 4.00; 1.0; 0.76 | Alias:<br>fluorescence binding:<br>minimum inhibition conc:<br>NMR sat. transfer: |
| 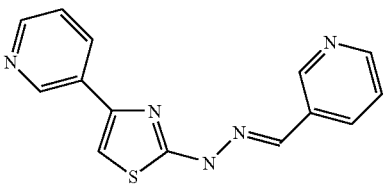 [SMILES: C(=N\Nc1nc(-c2cccnc2)cs1)/c1cccnc1]<br>3; 5773916; 281; 4.00; 1.0; 4.24 | Alias: CB-28<br>fluorescence binding: nd<br>minimum inhibition conc: nd<br>NMR sat. transfer: does not bind paHO |
| 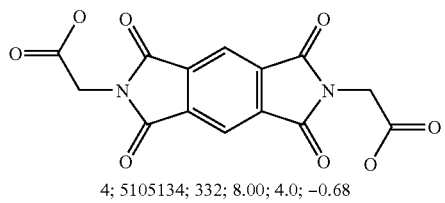<br>4; 5105134; 332; 8.00; 4.0; −0.68 | Alias: CB-2<br>fluorescence binding: nd<br>minimum binding conc: nd<br>NMR sat. transfer: do not bind paHO |
| 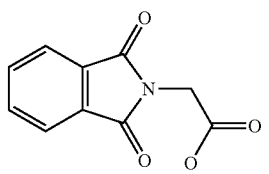 [SMILES: O=C(O)CN1C(=O)c2ccccc2C1=O]<br>5; 5140501; 205; 4.00; 2.0; 0.58 | Alias: CB-4<br>fluorescence binding: nd<br>minimum inhibition conc: nd<br>NMR sat. transfer: binds paHO |
| 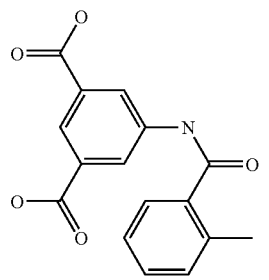 [SMILES: Cc1ccccc1C(=O)Nc1cc(C(=O)O)cc(C(=O)O)c1]<br>6; 5469632; 299; 5.00; 2.62 | Alias: CB-17<br>fluorescence binding: nd<br>minimum inhibition conc: nd<br>NMR sat. transfer: binds paHO |
| 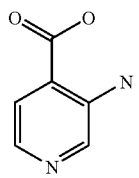<br>7; AJ-333/25006093; 138; 3.00; 3.0-0.32 | Alias:<br>fluorescence binding:<br>minimum inhibition conc:<br>NMR sat. transfer: |

TABLE 2-continued

| Compound | Comments |
|---|---|
| 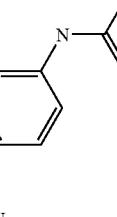<br>8; 6633579; 268; 4.00; 4.0; 0.79 | Alias: CB-38<br>fluorescence binding: nd<br>minimum inhibition conc: >750 ug/ml<br>NMR sat. transfer: nd<br>*E. coli* assay: green pellet |
| 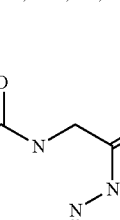<br>9; 2235-0060; 283; 5.00; 2.0; 0.32 | Alias: CD-21<br>fluorescence binding: nd<br>minimum inhibition conc: nd<br>NMR sat. transfer: do not bind paHO |
| 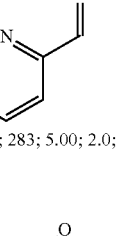<br>10; 2181-0037; 304; 3.00; 2.0; 3.16 | Alias: CD-8<br>fluorescence binding: nd<br>minimum inhibition conc: nd<br>NMR sat. transfer: do not bind paHO |
| 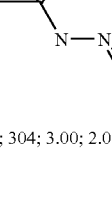<br>11; 0795-0144; 257; 5.00; 3.0; 1.88 | Alias: CD-20<br>fluorescence binding: nd<br>minimum inhibition conc: nd<br>NMR sat. transfer: do not bind paHO |
| 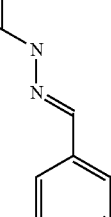<br>12; AG-205/33147035; 255; 4.00; 3.0; 3.28 | Alias:<br>fluorescence binding:<br>minimum inhibition conc:<br>NMR sat. transfer: |

TABLE 2-continued

| Compound | Comments |
|---|---|
| 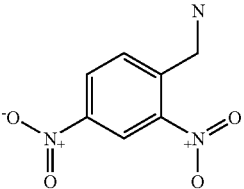<br>13; AF-628/30886065; 197; 1.00; 1.0; 1.07 | Alias: Spec-1 (Compound 8 in manuscript)<br>fluorescence binding: yes<br>minimum inhibition conc: nd<br>NMR sat. transfer: nd<br>*E. coli* assay: toxic to cells |
| 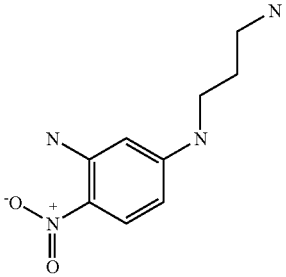<br>14; 5691472; 210; 1.00; 3.0; 0.38 | Alias:<br>fluorescence binding:<br>minimum inhibition conc:<br>NMR sat. transfer: |
| 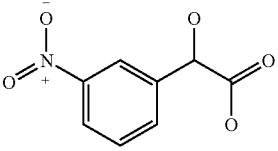<br>15; RJC 00897; 197; 3.00; 3.0; 0.98 | Alias:<br>fluorescence binding:<br>minimum inhibition conc:<br>NMR sat. transfer: |
| 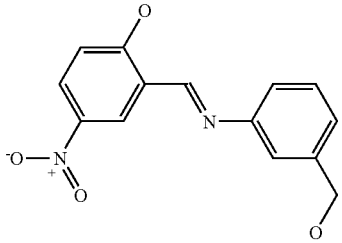<br>16; 8007-8333; 272; 3.00; 2.0; 2.71 | Alias: CD-23<br>fluorescence binding: nd<br>minimum inhibition conc: nd<br>NMR sat. transfer: do not bind paHO |
| 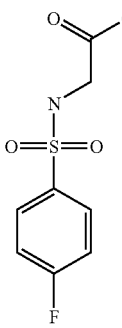<br>17; 4182-0978; 233; 4.00; 3.0; 0.66 | Alias:<br>fluorescence binding:<br>minimum inhibition conc:<br>NMR sat. transfer: |
| 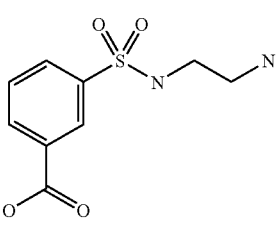 [SMILES: NCCNS(=O)(=O)c1cccc(C(=O)O)c1]<br>18; AO-623/37372005; 244; 5.00; 4.0; −0.20 | Alias: Spec-7<br>fluorescence binding: nd<br>minimum inhibition conc: nd<br>NMR sat. transfer: do not bind paHO |

TABLE 2-continued

| Compound | Comments |
|---|---|
| 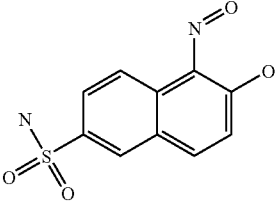 [SMILES: NS(=O)(=O)c1ccc2c(N=O)c(O)ccc2c1]<br>19; 5195223; 252; 5.00; 2.0; 1.30 | Alias:<br>fluorescence binding:<br>minimum inhibition conc:<br>NMR sat. transfer: |
| 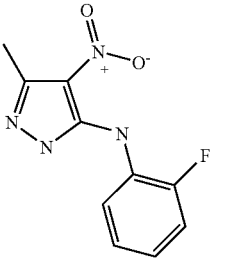<br>20; 1824-0926; 236; 1.00; 2.0; 2.63 | Alias: CD-6<br>fluorescence binding: nd<br>minimum inhibition conc: nd<br>NMR sat. transfer: do not bind paHO |
| 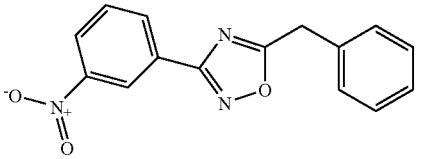<br>21; 4335-0782 21 O 281 2.00 0.0 3.33 | Alias: CD-11<br>fluorescence binding: nd<br>minimum inhibition conc: nd<br>NMR sat. transfer: do not bind paHO |
| 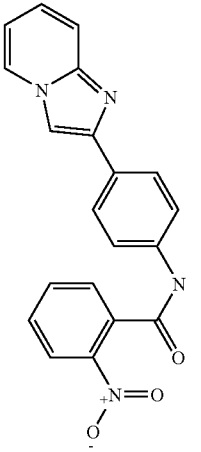<br>22; 6141274; 358; 2.00; 1.0; 3.56 | Alias: CB-35 Compound 4 in manuscript<br>fluorescence binding: yes<br>minimum inhibition conc: >380 ug/ml<br>NMR sat. transfer:<br>*E. coli* assay: white pellet |
| 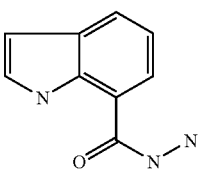 [SMILES: NNC(=O)c1cccc2cc[nH]c12]<br>23; SB 02108; 175; 2.00; 3.0; 0.80 | Alias: MB-9<br>fluorescence binding: nd<br>minimum inhibition conc: nd<br>NMR sat. transfer: nd |

TABLE 2-continued

| Compound | Comments |
| --- | --- |
| 24; K781-2231; 242; 4.00; 2.0; 0.05 | Alias: CD-18 (Compound 7 in manuscript)<br>fluorescence binding: yes<br>minimum inhibition conc: nd<br>NMR sat. transfer: nd<br>*E. coli* assay: green pellet |
| 25; 8006-5721; 178; 3.00; 1.0; 1.22 | Alias:<br>fluorescence binding:<br>minimum inhibition conc:<br>NMR sat. transfer: |
| 26; 8007-9340; 188; 2.00; 0.0; 1.95 | Alias:<br>fluorescence binding:<br>minimum inhibition conc:<br>NMR sat. transfer: |
| 27; AL-968/11987315; 278; 5.00; 2.0; −0.66 | Alias:<br>fluorescence binding:<br>minimum inhibition conc:<br>NMR sat. transfer: |
| 28; 1762-0550; 300; 2.00; 1.0; 0.92 | Alias:<br>fluorescence binding:<br>minimum inhibition conc:<br>NMR sat. transfer: |
| 29; 5190300; 253; 3.00; 0.0; 2.77 | Alias:<br>fluorescence binding:<br>minimum inhibition conc:<br>NMR sat. transfer: |
| 30; 5646855; 236; 4.00; 3.0; 1.34 | Alias:<br>fluorescence binding:<br>minimum inhibition conc:<br>NMR sat. transfer: |

TABLE 2-continued

| Compound | Comments |
|---|---|
| 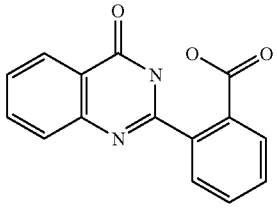 [SMILES: O=C(O)c1ccccc1-c1nc2ccccc2c(=O)[nH]1]<br>31; 12296; 266; 4.00; 3.0; 2.25 | Alias:<br>fluorescence binding:<br>minimum inhibition conc:<br>NMR sat. transfer: |
| 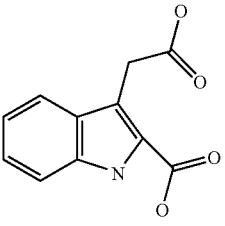 [SMILES: O=C(O)Cc1c(C(=O)O)[nH]c2ccccc12]<br>32; 6772246; 219; 4.00; 5.0; 1.67 | Alias:<br>fluorescence binding:<br>minimum inhibition conc:<br>NMR sat. transfer: |
| 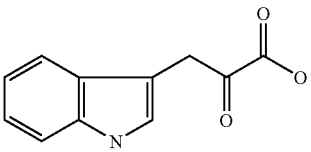 [SMILES: O=C(O)C(=O)Cc1c[nH]c2ccccc12]<br>33; JFD 01266; 203; 3.00; 3.0; 1.59 | Alias: MB-1<br>fluorescence binding: yes<br>minimum inhibition conc: nd<br>NMR sat. transfer: |
| 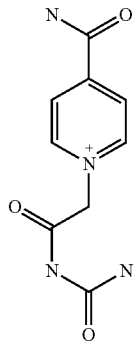<br>34; 0173-0031; 223; 3.00; 3.0; −1.11 | Alias: CD-3<br>fluorescence binding: nd<br>minimum inhibition conc: nd<br>NMR sat. transfer: do not bind paHO |
| 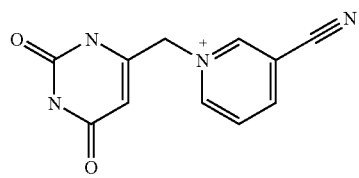<br>35; AI-204/3167006; 229; 3.00; 2.0; 0.38 | Alias:<br>fluorescence binding:<br>minimum inhibition conc:<br>NMR sat. transfer: |
| 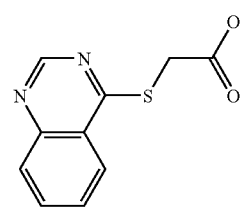 [SMILES: O=C(O)CSc1ncnc2ccccc12]<br>36; 5509623; 220; 4.00; 2.0; 1.46 | Alias: CB-21<br>fluorescence binding: nd<br>minimum inhibition conc: no antibacterial activity<br>NMR sat. transfer: binds paHO |

TABLE 2-continued

| Compound | Comments |
|---|---|
| 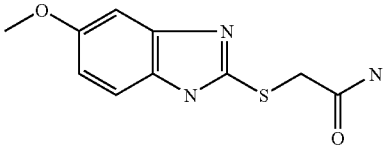 [SMILES: COc1ccc2[nH]c(SCC(N)=O)nc2c1]<br>37; 8009-6712; 237; 3.00; 3.0; 1.01 | Alias:<br>fluorescence binding:<br>minimum inhibition conc:<br>NMR sat. transfer: |
| 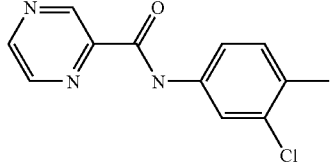 [SMILES: Cc1ccc(NC(=O)c2cnccn2)cc1Cl]<br>38; 5549127; 247; 3.00 1.0 1.48 | Alias: CB-24<br>fluorescence binding: nd<br>minimum inhibition conc: nd<br>NMR sat. transfer: does not bind paHO |
| 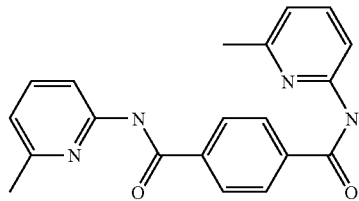 [SMILES: Cc1cccc(NC(=O)c2ccc(C(=O)Nc3cccc(C)n3)cc2)n1]<br>39; 5491548; 346; 4.00; 2.0; 2.68 | Alias: CB-20<br>fluorescence binding: nd<br>minimum inhibition conc: nd<br>NMR sat. transfer: tested, ambiguous |
| 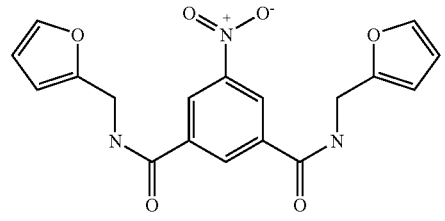<br>40; 5614227; 369; 2.00; 2.0; 1.56 | Alias: CB-25<br>fluorescence binding: nd<br>minimum inhibition conc: nd<br>NMR sat. transfer: does not bind paHO |
| 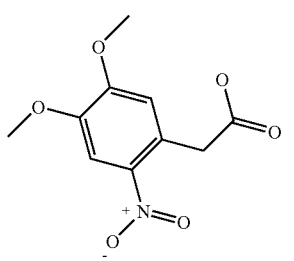<br>41; CD 01521; 241; 2.00; 2.0; 1.3 | Alias: MB-5<br>fluorescence binding: nd<br>minimum inhibition conc: nd<br>NMR sat. transfer: nd |
| 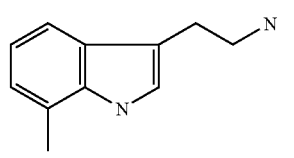<br>42; 5102414; 174; 1.00; 2.0; 1.9 | Alias:<br>fluorescence binding:<br>minimum inhibition conc:<br>NMR sat. transfer: |

TABLE 2-continued

| Compound | Comments |
|---|---|
| 43: 1988-0303; 318; 5.00; 3.0; 0.86 | Alias: CD-7<br>fluorescence binding: nd<br>minimum inhibition conc: nd<br>NMR sat. transfer: do not bind paHO |
| 44; 5538509; 299; 3.00; 2.0; 3.41 | Alias: CB-22<br>fluorescence binding: nd<br>minimum inhibition conc: nd<br>NMR sat. transfer: tested, ambiguous |
| 45; 2214-0019; 313; 2.00; 1.0; 3.67 | Alias:<br>fluorescence binding:<br>minimum inhibition conc:<br>NMR sat. transfer: |
| 46; 6157486; 288; 3.00; 2.0; 2.6 | Alias: CB-36<br>fluorescence binding: nd<br>minimum inhibition conc: nd<br>NMR sat. transfer: nd |
| 47; 5128372; 298; 2.00; 0.0; 2.53 | Alias: CB-3<br>fluorescence binding: nd<br>minimum inhibition conc: nd<br>NMR sat. transfer: do not bind paHO |

TABLE 2-continued

| Compound | Comments |
|---|---|
| 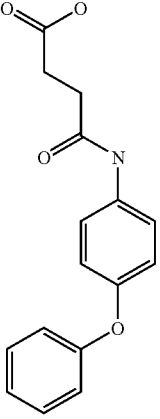 [SMILES: O=C(O)CCC(=O)Nc1ccc(Oc2ccccc2)cc1]<br>48; AE-641/00427005; 285; 3.00; 3.0; 2.36 | Alias: Spec-3<br>fluorescence binding: nd<br>minimum inhibition conc: nd<br>NMR sat. transfer: do not bind paHO<br>*E. coli* assay: white pellet |
| 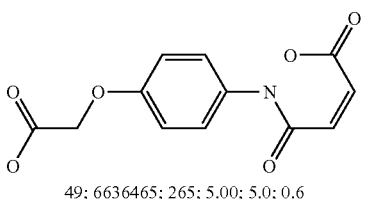<br>49; 6636465; 265; 5.00; 5.0; 0.6 | Alias: CB-39<br>fluorescence binding: nd<br>minimum inhibition conc: nd<br>NMR sat. transfer: nd |
| 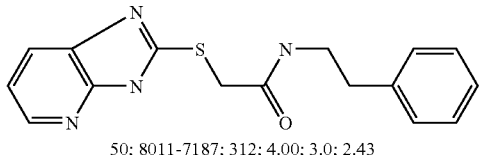<br>50; 8011-7187; 312; 4.00; 3.0; 2.43 | Alias:<br>fluorescence binding:<br>minimum inhibition conc:<br>NMR sat. transfer: |
| 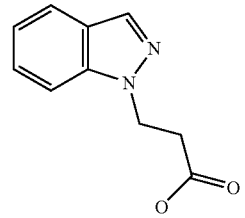 [SMILES: O=C(O)CCn1ncc2ccccc21]<br>51; 1300-0270; 190; 3.00; 2.0; 0.91 | Alias: CD-5<br>fluorescence binding: nd<br>minimum inhibition conc: nd<br>NMR sat. transfer: do not bind paHO |
| 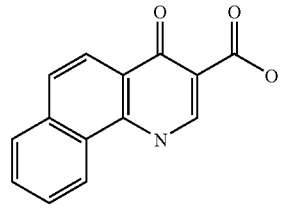 [SMILES: O=C(O)c1c[nH]c2c(ccc3ccccc32)c1=O]<br>52; AE-641/12845537; 239; 3.00; 3.0; 1.87 | Alias: Spec-2<br>fluorescence binding: nd<br>minimum inhibition conc: nd<br>NMR sat. transfer: do not bind paHO |
| 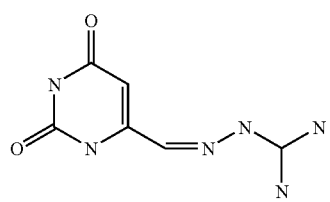 [SMILES: NC(N)N/N=C\c1cc(=O)[nH]c(=O)[nH]1]<br>53; NRB 04430; 198; 5.00; 5.0; −1.79 | Alias:<br>fluorescence binding:<br>minimum inhibition conc:<br>NMR sat. transfer: |

TABLE 2-continued

| Compound | Comments |
|---|---|
| 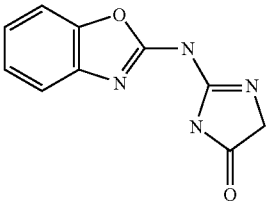 [SMILES: O=C1CN=C(Nc2nc3ccccc3o2)N1]<br>54; 5662878; 216; 3.00; 2.0; 0.62 | Alias:<br>fluorescence binding:<br>minimum inhibition conc:<br>NMR sat. transfer: |
| 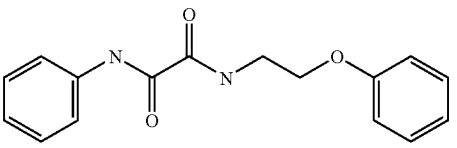 [SMILES: O=C(NCCOc1ccccc1)C(=O)Nc1ccccc1]<br>55; 6526505; 284; 2.00; 2.0; 1.77 | Alias: CB-37<br>fluorescence binding: nd<br>minimum inhibition conc: nd<br>NMR sat. transfer: nd |
| 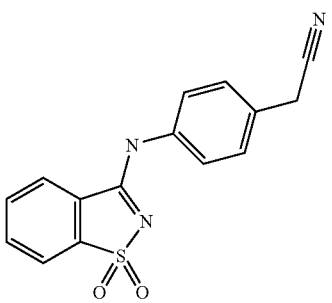 [SMILES: N#CCc1ccc(NC2=NS(=O)(=O)c3ccccc32)cc1]<br>56; 8010-5978; 297; 4.00; 1.0; 2.81 | Alias: CD-16<br>fluorescence binding: nd<br>minimum inhibition conc: nd<br>NMR sat. transfer: do not bind paHO |
| 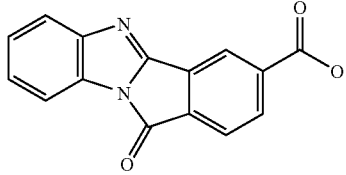 [SMILES: O=C(O)c1ccc2c(c1)-c1nc3ccccc3n1C2=O]<br>57; 0812-1008; 264; 4.00; 2.0; 2.52 | Alias: CD-4<br>fluorescence binding: nd<br>minimum inhibition conc: nd<br>NMR sat. transfer: do not bind paHO |
| 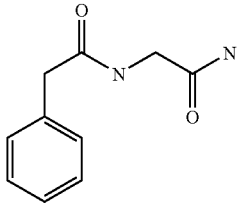 [SMILES: NC(=O)CNC(=O)Cc1ccccc1]<br>58; 8006-6118; 192; 2.00; 2.0; 0.06 | Alias:<br>fluorescence binding:<br>minimum inhibition conc:<br>NMR sat. transfer: |
| 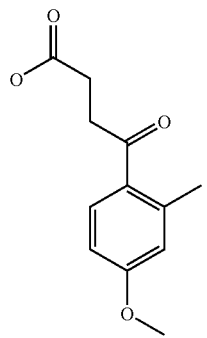 [SMILES: COc1ccc(C(=O)CCC(=O)O)c(C)c1]<br>59; 4696-0935; 222; 3.00; 2.0; 1.60 | Alias: CD-12<br>fluorescence binding: yes<br>minimum inhibition conc: >1000 ug/ml<br>NMR sat. transfer: yes, bind paHO |

TABLE 2-continued

| Compound | Comments |
|---|---|
| 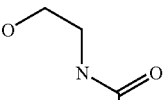<br>60; 4748-0824; 311; 3.00; 4.0; 1.4 | Alias:<br>fluorescence binding:<br>minimum inhibition conc:<br>NMR sat. transfer: |
| 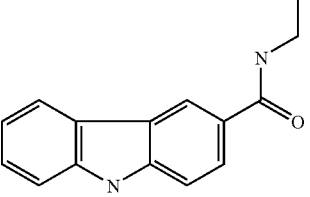<br>61; 5940661; 256; 3.00; 2.0; 3.51 | Alias: CB-32<br>fluorescence binding: nd<br>minimum inhibition conc: no antibacterial activity<br>NMR sat. transfer: yes, bind to paHO |
| 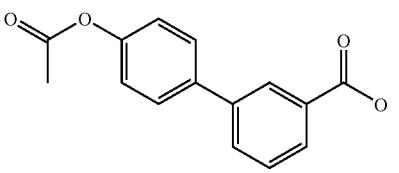 [SMILES: CC(=O)Oc1ccc(-c2cccc(C(=O)O)c2)cc1]<br>62; 5546064; 250; 4.00; 2.0; 2.51 | Alias: CB-23<br>fluorescence binding: nd<br>minimum inhibition conc: nd<br>NMR sat. transfer: does not bind paHO |
| 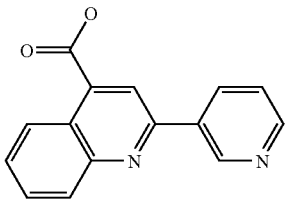 [SMILES: O=C(O)c1cc(-c2cccnc2)nc2ccccc12]<br>63; SB 00515; 108; 2.00; 1.0; −0.11 | Alias:<br>fluorescence binding:<br>minimum inhibition conc:<br>NMR sat. transfer: |
| 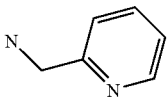<br>64; AG-390/2510001; 199; 3.00; 1.0; 1.01 | Alias: Spec-12<br>fluorescence binding: nd<br>minimum inhibition conc: nd<br>NMR sat. transfer: do not bind paHO |
| 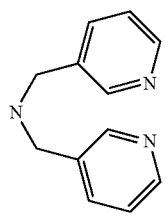<br>65; 5182313; 221; 2.00; 5.0; 1.46 | Alias:<br>fluorescence binding:<br>minimum inhibition conc:<br>NMR sat. transfer: |
| 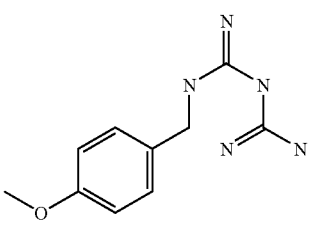 [SMILES: COc1ccc(CNC(=N)NC(=N)N)cc1]<br>66; RJC 00448; 218; 2.00; 2.0; 3.22 | Alias:<br>fluorescence binding:<br>minimum inhibition conc:<br>NMR sat. transfer: |

TABLE 2-continued

| Compound | Comments |
|---|---|
| 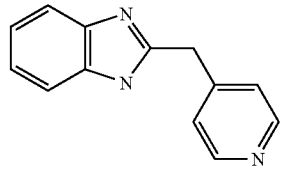 [SMILES: c1ccc2[nH]c(Cc3ccncc3)nc2c1]<br>67; AP-044/15268049; 209; 3.00; 2.0; 2.14 | Alias:<br>fluorescence binding:<br>minimum inhibition conc:<br>NMR sat. transfer: |
| 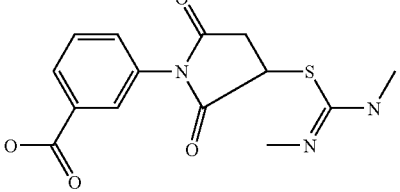<br>68: 8010-6092; 321; 5.00; 3.0; 1.25 | Alias:<br>fluorescence binding:<br>minimum inhibition conc:<br>NMR sat. transfer: |
| 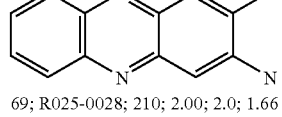<br>69; R025-0028; 210; 2.00; 2.0; 1.66 | Alias:<br>fluorescence binding:<br>minimum inhibition conc:<br>NMR sat. transfer: |
| 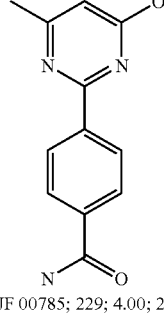<br>70; RJF 00785; 229; 4.00; 2.0; 0.86 | Alias: MB-3<br>fluorescence binding: nd<br>minimum inhibition conc: nd<br>NMR sat. transfer: nd |
| 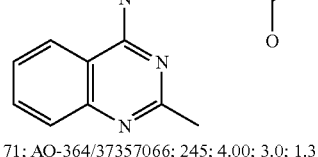<br>71; AO-364/37357066; 245; 4.00; 3.0; 1.38 | Alias: Spec-6<br>fluorescence binding: nd<br>minimum inhibition conc: nd<br>NMR sat. transfer: do not bind paHO |
| 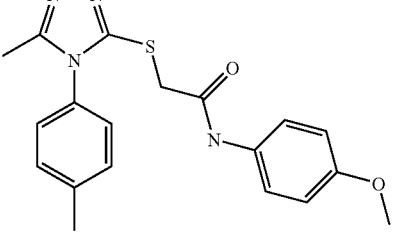<br>72; AG-690/40753661; 368; 3.00; 1.0; 3.95 | Alias:<br>fluorescence binding:<br>minimum inhibition conc:<br>NMR sat. transfer: |

TABLE 2-continued

| Compound | Comments |
| --- | --- |
| 73; 0091-0260; 341; 4.00; 3.0; 2.13 | Alias: CD-1<br>fluorescence binding: nd<br>minimum inhibition conc: nd<br>NMR sat. transfer: do not bind paHO |
| 74; 5101730; 296; 2.00; 0.0; 3.7 | Alias: CB-1<br>fluorescence binding: nd<br>minimum inhibition conc: nd<br>NMR sat. transfer: do not bind paHO |
| 75; 5191821; 282; 3.00; 4.0; 2.60 | Alias: CB-7 Compound 3 in manuscript<br>fluorescence binding: yes<br>minimum inhibition conc: >1000 ug/ml<br>NMR sat. transfer:<br>*E. coli* assay: white pellet |
| 76; GK 01678; 204; 2.00; 2.0; 1.07 | Alias: MB-2<br>fluorescence binding: yes<br>minimum inhibition conc: nd<br>NMR sat. transfer: |
| 77; 5405901; 301; 4.00; 2.0; 3.03 | Alias: CB-16<br>fluorescence binding: nd<br>minimum inhibition conc: nd<br>NMR sat. transfer: binds paHO |
| 78; AG-227/37195034; 325; 4.00; 2.0; 3.60 | Alias:<br>fluorescence binding:<br>minimum inhibition conc:<br>NMR sat. transfer: |

TABLE 2-continued

| Compound | Comments |
|---|---|
| 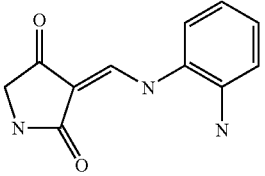 [SMILES: Nc1ccccc1N/C=C1/C(=O)CNC1=O]<br>79; 5473222; 217; 2.00; 3.0; −0.57 | Alias:<br>fluorescence binding:<br>minimum inhibition conc:<br>NMR sat. transfer: |
| 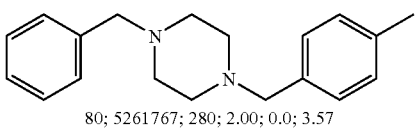<br>80; 5261767; 280; 2.00; 0.0; 3.57 | Alias: CB-10<br>fluorescence binding: nd<br>minimum inhibition conc: nd<br>NMR sat. transfer: binds paHO |
| 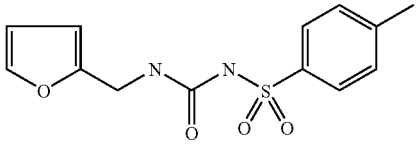 [SMILES: Cc1ccc(S(=O)(=O)NC(=O)NCc2ccco2)cc1]<br>81; SEW 0444; 294; 3.00; 2.0; 1.20 | Alias: MB-8<br>fluorescence binding: nd<br>minimum inhibition conc: nd<br>NMR sat. transfer: nd |
| 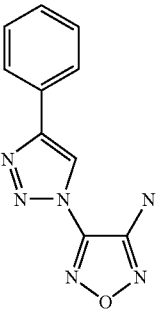 [SMILES: Nc1nonc1-n1cc(-c2ccccc2)nn1]<br>82; 1307-0011; 228; 4.00; 1.0; 1.15 | Alias:<br>fluorescence binding:<br>minimum inhibition conc:<br>NMR sat. transfer: |
| 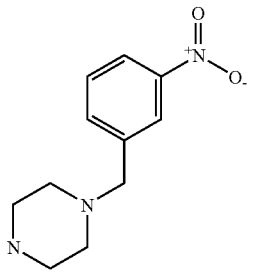 [SMILES: O=[N+]([O-])c1cccc(CN2CCNCC2)c1]<br>83; 5881261; 221; 2.00; 1.0; 1.18 | Alias: CB-29<br>fluorescence binding: nd<br>minimum inhibition conc: no antibacterial activity<br>NMR sat. transfer: yes, bind paHO |
| 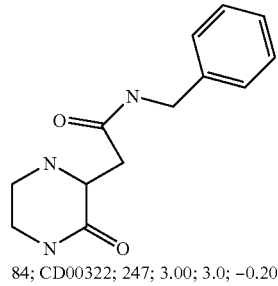<br>84; CD00322; 247; 3.00; 3.0; −0.20 | Alias:<br>fluorescence binding:<br>minimum inhibition conc:<br>NMR sat. transfer: |

TABLE 2-continued

| Compound | Comments |
|---|---|
| 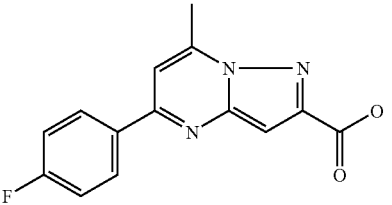 [SMILES: Cc1cc(-c2ccc(F)cc2)nc2cc(C(=O)O)nn12]<br>85; AK-968/37055109; 271; 4.00; 2.0; 2.08 | Alias: Spec-9 (SpecA)<br>fluorescence binding: nd<br>minimum inhibition conc: no antibacterial activity<br>NMR sat. transfer: yes, bind paHO |
| 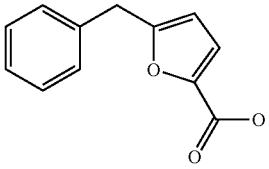 [SMILES: O=C(O)c1ccc(Cc2ccccc2)o1]<br>86: 5182404; 202; 2.00; 2.0; 2.22 | Alias:<br>fluorescence binding:<br>minimum inhibition conc:<br>NMR sat. transfer: |
| 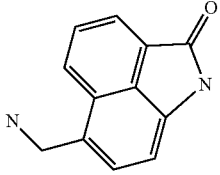 [SMILES: NCc1ccc2c3c(cccc13)C(=O)N2]<br>87: AF-399/40768858; 198; 2.00; 2.0; 1.36 | Alias: Spec-13 (SpecH)<br>fluorescence binding: nd<br>minimum inhibition conc: >125 ug/ml<br>NMR sat. transfer: yes, bind paHO<br>*C. elegans*: ongoing study |
| 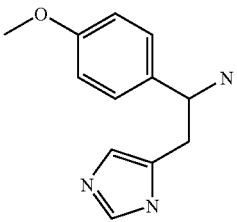 [SMILES: COc1ccc(C(N)Cc2cnc[nH]2)cc1]<br>88; AM-814/41092503; 217; 3.00; 3.0; 0.81 | Alias:<br>fluorescence binding:<br>minimum inhibition conc:<br>NMR sat. transfer: |
| 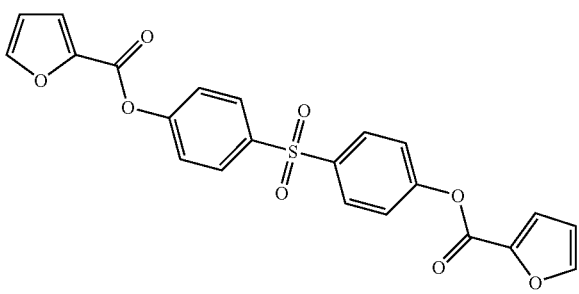 [SMILES: O=C(Oc1ccc(S(=O)(=O)c2ccc(OC(=O)c3ccco3)cc2)cc1)c1ccco1]<br>89; 0606-3241; 438; 4.00; 0.0; 3.38 | Alias:<br>fluorescence binding:<br>minimum inhibition conc:<br>NMR sat. transfer: |
| 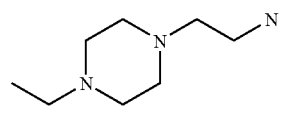<br>90; R152-0479; 157; 3.00; 1.0; −0.88 | Alias: CD-19<br>fluorescence binding: nd<br>minimum inhibition conc: nd<br>NMR sat. transfer: do not bind paHO |

TABLE 2-continued

| Compound | Comments |
|---|---|
| 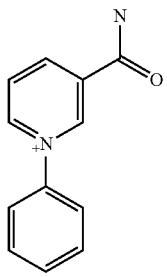 [SMILES: NC(=O)c1ccc[n+](-c2ccccc2)c1]<br>91; AC-907/25005164; 199; 1.00; 1.0; 2.15 | Alias: Spec-10<br>fluorescence binding: nd<br>minimum inhibition conc: nd<br>NMR sat. transfer: do not bind paHO |
| 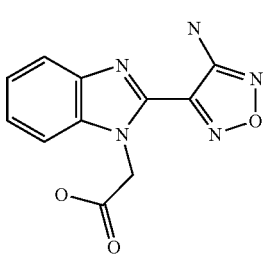 [SMILES: Nc1nonc1-c1nc2ccccc2n1CC(=O)O]<br>92; 2144-0684; 259; 5.00; 3.0; 1.08 | Alias:<br>fluorescence binding:<br>minimum inhibition conc:<br>NMR sat. transfer: |
| 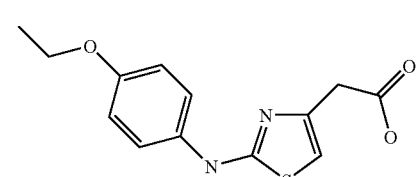<br>93; 6264623; 278; 3.00; 3.0; 2.29 | Alias:<br>fluorescence binding:<br>minimum inhibition conc:<br>NMR sat. transfer: |
| 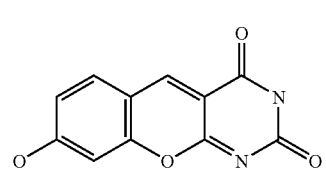 [SMILES: O=c1nc2oc3cc(O)ccc3cc-2c(=O)[nH]1]<br>94; AG-205/14142069; 230; 4.00; 2.0; 1.25 | Alias:<br>fluorescence binding:<br>minimum inhibition conc:<br>NMR sat. transfer: |
| 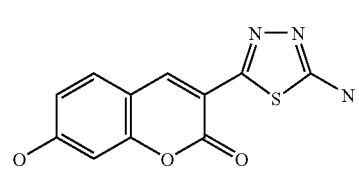 [SMILES: Nc1nnc(-c2cc3ccc(O)cc3oc2=O)s1]<br>95; AH-034/11696213; 261; 4.00; 2.0; 2.05 | Alias:<br>fluorescence binding:<br>minimum inhibition conc:<br>NMR sat. transfer: |
| 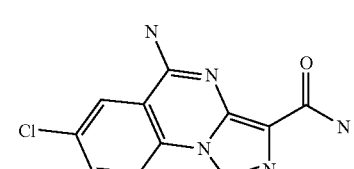<br>96; 4048-4309; 262; 4.00; 2.0; −0.14 | Alias:<br>fluorescence binding:<br>minimum inhibition conc:<br>NMR sat. transfer: |
| 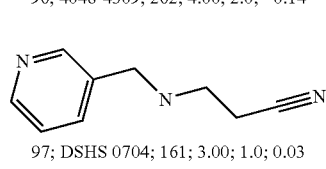<br>97; DSHS 0704; 161; 3.00; 1.0; 0.03 | Alias:<br>fluorescence binding:<br>minimum inhibition conc:<br>NMR sat. transfer: |

TABLE 2-continued

| Compound | Comments |
|---|---|
| 98; 5345917; 242; 2.00; 0.0; 3.05 | Alias: CB-12<br>fluorescence binding: nd<br>minimum inhibition conc: nd<br>NMR sat. transfer: binds paHO |
| 99; 6139643; 247; 2.00; 1.0; 1.46 | Alias: CB-34<br>fluorescence binding: nd<br>minimum inhibition conc: nd<br>NMR sat. transfer: nd |
| 100; 4534-0084; 255; 3.00; 1.0; 2.61 | Alias:<br>fluorescence binding:<br>minimum inhibition conc:<br>NMR sat. transfer: |
| 101; 5173235; 343; 1.00; 1.0; 4.62 | Alias: CB-6<br>fluorescence binding: nd<br>minimum inhibition conc: no antibacterial activity<br>NMR sat. transfer: 02/05/07; binds paHO |
| 102; 1514-0057; 240; 3.00; 0.0; 0.89 | Alias:<br>fluorescence binding:<br>minimum inhibition conc:<br>NMR sat. transfer: |
| 103; AI-942/25034862; 171; 1.00; 1.0; 2.88 | Alias: Spec-11 (or SpecC)<br>fluorescence binding: nd<br>minimum inhibition conc: >250 ug/ml<br>NMR sat. transfer: yes, bind paHO |
| 104; 8005-4121; 231; 2.00; 1.0; 2.07 | Alias: CD-13<br>fluorescence binding: nd<br>minimum inhibition conc: nd<br>NMR sat. transfer: do not bind paHO |

TABLE 2-continued

| Compound | Comments |
|---|---|
| 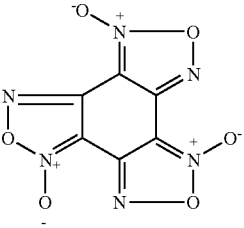<br>105; 8010-7497; 252; 6.00; 0.0; 0.64 | Alias:<br>fluorescence binding:<br>minimum inhibition conc:<br>NMR sat. transfer: |
| 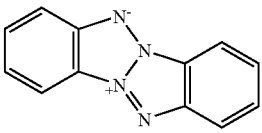 [SMILES: c1ccc2c(c1)n[n+]1c3ccccc3[n-]n21]<br>106; 1350-0012; 208; 1.00; 0.0; 2.00 | Alias:<br>fluorescence binding:<br>minimum inhibition conc:<br>NMR sat. transfer: |
| 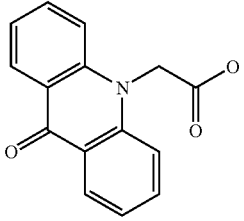 [SMILES: O=C(O)Cn1c2ccccc2c(=O)c2ccccc21]<br>107; 2825-0171; 253; 3.00; 2.0; 2.67 | Alias: CD-10<br>fluorescence binding: nd<br>minimum inhibition conc: no antibacterial activity<br>NMR sat. transfer: yes, bind paHO |
| 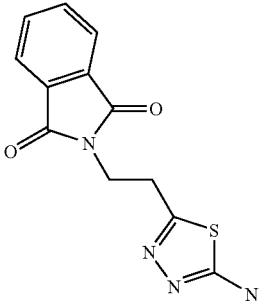 [SMILES: Nc1nnc(CCN2C(=O)c3ccccc3C2=O)s1]<br>108; 5139581; 274; 4.00; 1.0; 1.39 | Alias:<br>fluorescence binding:<br>minimum inhibition conc:<br>NMR sat. transfer: |
| 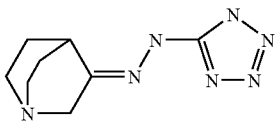<br>109; 1269-3861; 207; 5.00; 2.0; 1.56 | Alias:<br>fluorescence binding:<br>minimum inhibition conc:<br>NMR sat. transfer: |
| 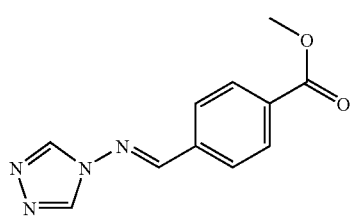 [SMILES: COC(=O)c1ccc(/C=N/n2cnnc2)cc1]<br>110; 5485930; 230; 4.00; 0.0; 1.55 | Alias:<br>fluorescence binding:<br>minimum inhibition conc:<br>NMR sat. transfer: |

TABLE 2-continued

| Compound | Comments |
|---|---|
| 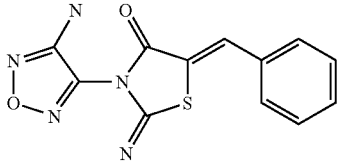 [SMILES: N=C1S/C(=C\c2ccccc2)C(=O)N1c1nonc1N]<br>111; 8010-9844; 287; 4.00; 2.0; 2.40 | Alias:<br>fluorescence binding:<br>minimum inhibition conc:<br>NMR sat. transfer: |
| 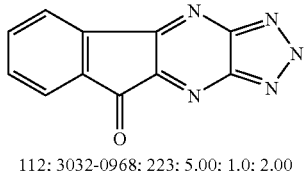<br>112; 3032-0968; 223; 5.00; 1.0; 2.00 | Alias:<br>fluorescence binding:<br>minimum inhibitiopn conc:<br>NMR sat. transfer: |
| 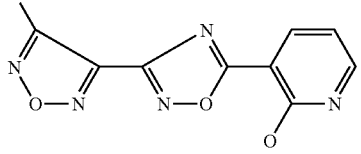<br>113; 8012-4154; 246; 6.00; 2.0; 0.04 | Alias: CD-17<br>fluorescence binding: nd<br>minimum inhibition conc: nd<br>NMR sat. transfer: do not bind paHO |
| 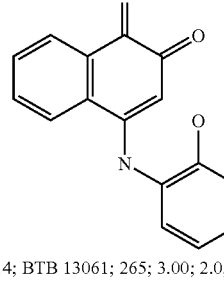<br>114; BTB 13061; 265; 3.00; 2.0; 2.80 | Alias: MB-6 Compound 6 in manuscript.<br>fluorescence binding: yes<br>minimum inhibition conc: nd<br>NMR sat. transfer:<br>*E. coli* assay: toxic to cells |
| 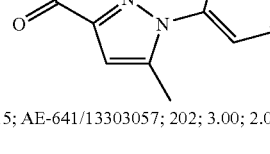<br>115; AE-641/13303057; 202; 3.00; 2.0; 1.47 | Alias: Spec-14 (or Spec G)<br>fluorescence binding: nd<br>minimum inhibition conc: no antibacterial activity<br>NMR sat. transfer: yes, bind paHO |
| 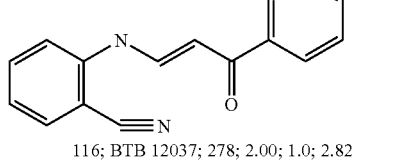<br>116; BTB 12037; 278; 2.00; 1.0; 2.82 | Alias: MB-7<br>fluorescence binding: nd<br>minimum inhibition conc: nd<br>NMR sat. transfer: nd |
| 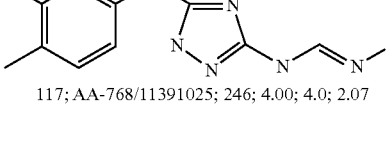<br>117; AA-768/11391025; 246; 4.00; 4.0; 2.07 | Alias:<br>fluorescence binding:<br>minimum inhibition conc:<br>NMR sat. transfer: |

TABLE 2-continued

| Compound | Comments |
|---|---|
| 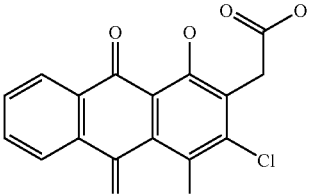<br>118; 0053-0043; 332; 6.00; 4.0; 2.69 | Alias:<br>fluorescence binding:<br>minimum inhibition conc:<br>NMR sat. transfer: |
| 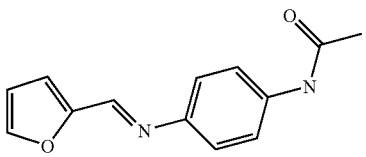 [SMILES: CC(=O)Nc1ccc(/N=C/c2ccco2)cc1]<br>119; 8003-8606; 228; 2.00; 1.0; 1.54 | Alias: CD-22<br>fluorescence binding: yes<br>minimum inhibition conc: nd<br>NMR sat. transfer: do not bind paHO |
| 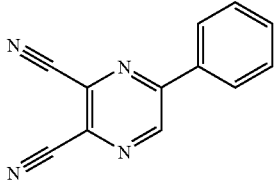 [SMILES: N#Cc1ncc(-c2ccccc2)nc1C#N]<br>120; AN-885/41077119; 206; 4.00; 0.0; 0.80 | Alias: Spec-15<br>fluorescence binding: nd<br>minimum inhibition conc: nd<br>NMR sat. transfer: do not bind paHO |
| 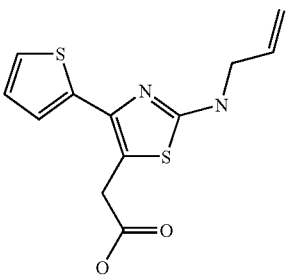 [SMILES: C=CCNc1nc(-c2cccs2)c(CC(=O)O)s1]<br>121: 2650-8681; 280; 3.00; 3.0; 2.29 | Alias:<br>fluorescence binding:<br>minimum inhibition conc:<br>NMR sat. transfer: |
| 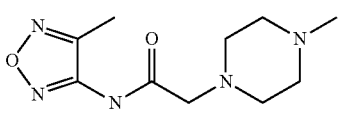 [SMILES: Cc1nonc1NC(=O)CN1CCN(C)CC1]<br>122; 4596-0330; 239; 5.00; 1.0; −1.04 | Alias:<br>fluorescence binding:<br>minimum inhibition conc:<br>NMR sat. transfer: |
| 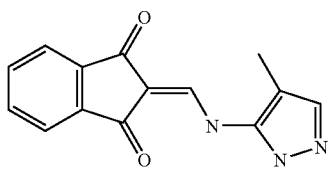 [SMILES: Cc1cn[nH]c1NC=C1C(=O)c2ccccc2C1=O]<br>123; AP-982/40918815; 253; 3.00; 2.0; 1.79 | Alias:<br>fluorescence binding:<br>minimum inhibition conc:<br>NMR sat. transfer: |
| 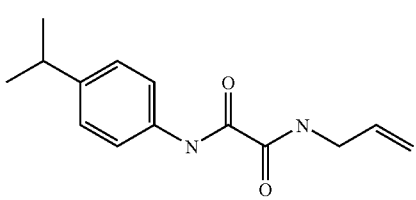 [SMILES: C=CCNC(=O)C(=O)Nc1ccc(C(C)C)cc1]<br>124; 5914078; 246; 2.00; 2.0; 2.00; | Alias: CB-30<br>fluorescence binding: nd<br>minimum inhibition conc: nd<br>NMR sat. transfer: tested, ambiguous |

TABLE 2-continued

| Compound | Comments |
|---|---|
| 125; NH 00373; 244; 3.00; 1.0; 1.15 | Alias: MB-10<br>fluorescence binding: nd<br>minimum inhibition conc: nd<br>NMR sat. transfer: nd |
| 126; 5474974; 311; 2.00; 2.0; 4.74 | Alias: CB-18 (Compound 2 in manuscript<br>fluorescence binding: yes<br>minimum inhibition conc: no antibacterial activity<br>NMR sat. transfer:<br>*E. coli* assay: white pellet |
| 127; AM-814/41093338; 180; 3.00; 2.0; 0.19 | Alias: Spec-8 (or SpecJ)<br>fluorescence binding: nd<br>minimum inhibition conc: >1000 ug/ml<br>NMR sat. transfer: yes, bind paHO |
| 128; AJ-292/13046020; 293; 3.00; 0.0; 2.29 | Alias: Spec-4<br>fluorescence binding: nd<br>minimum inhibition conc: nd<br>NMR sat. transfer: do not bind paHO |
| 129; S 12327; 210; 1.00; 2.0; 2.27 | Alias:<br>fluorescence binding:<br>minimum binding conc:<br>NMR sat. transfer: |
| 130; BTB 02612; 314; 4.00; 3.0; −0.72 | Alias: MB-4<br>fluorescence binding: nd<br>minimum inhibition conc: nd<br>NMR sat. transfer: nd |

TABLE 2-continued

| Compound | Comments |
|---|---|
| 131; 8010-0630; 282; 2.00; 2.0; 3.63 | Alias: CD-14<br>fluorescence binding: nd<br>minimum inhibition conc: >250 ug/ml<br>NMR sat. transfer: yes, bind paHO |
| 132; 5350435; 262; 3.00; 1.0; 1.93 | Alias: CB-13<br>fluorescence binding: nd<br>minimum inhibition conc: nd<br>NMR sat. transfer: tested, ambiguous |
| 133; 5242836; 233; 4.00; 0.0; −0.96 | Alias: CB-9<br>fluorescence binding: nd<br>minimum inhibition conc: nd<br>NMR sat. transfer: nd<br>*E. coli* assay: green pellet |
| 134; 6098968; 285; 5.00; 5.0; 1.62 | Alias: CB-33<br>fluorescence binding: nd<br>minimum inhibition conc: nd<br>NMR sat. transfer: nd |
| 135; 5852138; 266; 4.00; 3.0; −0.43 | Alias:<br>fluorescence binding:<br>minimum inhibition conc:<br>NMR sat. transfer: |
| 136; AE-641/30177008; 259; 1.00; 1.0; 3.92 | Alias:<br>fluorescence binding:<br>minimum inhibition conc:<br>NMR sat. transfer: |
| 137; 8011-1056; 267; 3.00; 2.0; 1.92 | Alias: CD-24<br>fluorescence binding: yes<br>minimum inhibition conc: nd<br>NMR sat. transfer: do not bind paHO |

TABLE 2-continued

| Compound | Comments |
|---|---|
| 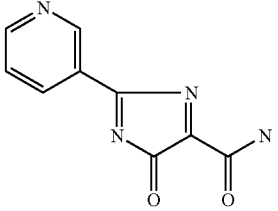 [SMILES: NC(=O)C1=NC(c2cccnc2)=NC1=O]<br>138; SEW 00623; 202; 5.00; 1.0; −1.12 | Alias:<br>fluorescence binding:<br>minimum inhibition conc:<br>NMR sat. transfer: |
| 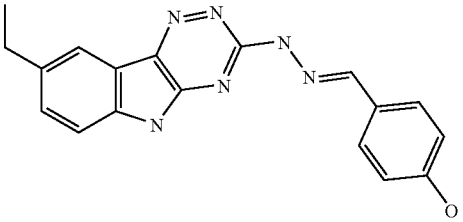 [SMILES: CCc1ccc2[nH]c3nc(N/N=C/c4ccc(O)cc4)nnc3c2c1]<br>139; 5753479; 332; 5.00; 3.0; 7.15 | Alias: CB-27<br>fluorescence binding: nd<br>minimum inhibition conc: nd<br>NMR sat. transfer: does not bind paHO |
| 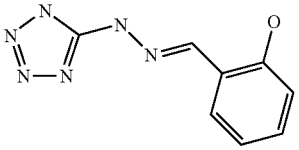 [SMILES: Oc1ccccc1/C=N/Nc1nnn[nH]1]<br>140; 5317991; 204; 5.00; 3.0; 3.23 | Alias: CB-11<br>fluorescence binding: nd<br>minimum inhibition conc: nd<br>NMR sat. transfer: binds paHO |
| 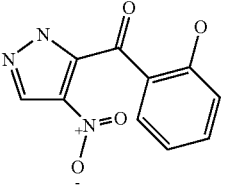<br>141; 8010-7768; 233; 3.00; 2.0; 1.60 | Alias:<br>fluorescence binding:<br>minimum inhibition conc:<br>NMR sat. transfer: |
| 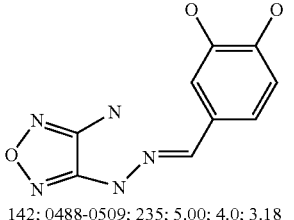<br>142; 0488-0509; 235; 5.00; 4.0; 3.18 | Alias:<br>fluorescence binding:<br>minimum inhibition conc:<br>NMR sat. transfer: |
| 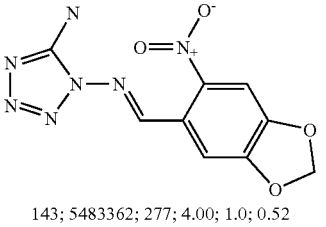<br>143; 5483362; 277; 4.00; 1.0; 0.52 | Alias: CB-19<br>fluorescence binding: nd<br>minimum inhibition conc: nd<br>NMR sat. transfer: binds paHO |

TABLE 2-continued

| Compound | Comments |
|---|---|
| 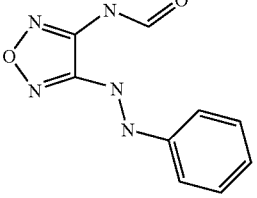<br>144; 5373938; 219; 3.00; 3.0; 0.89 | Alias: CB-15<br>fluorescence binding: nd<br>minimum inhibition conc: nd<br>NMR sat. transfer: tested, ambiguous |
| 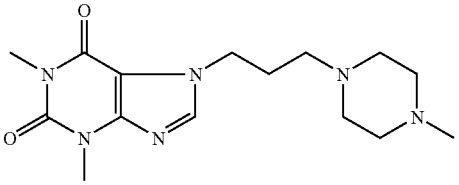<br>145; 5351316; 320; 5.00; 0.0; −0.76 | Alias: CB-14<br>fluorescence binding: nd<br>minimum inhibition conc: nd<br>NMR sat. transfer: tested, ambiguous |
| 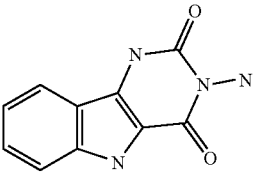 [SMILES: Nn1c(=O)[nH]c2c([nH]c3ccccc32)c1=O]<br>146; 5647215; 216 3.00 3.0 0.26 | Alias:<br>fluorescence binding:<br>minimum inhibition conc:<br>NMR sat. transfer: |
| 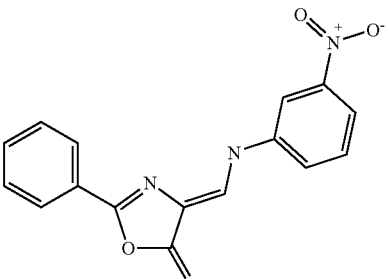<br>147; 5650366; 309; 2.00; 1.0; 3.05 | Alias: CB-26<br>fluorescence binding: nd<br>minimum inhibition conc: nd<br>NMR sat. transfer: does not bind paHO |
| 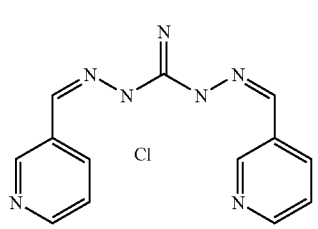 [SMILES: N=C(N/N=C\c1cccnc1)N/N=C\c1cccnc1 ; Cl]<br>148; 5928257; 303; 5.00; 3.0; 7.05 | Alias: CB-31 Compound 1 in manuscript<br>fluorescence binding: yes<br>minimum inhibition conc: no antibacterial activity<br>NMR sat. transfer:<br>*E. coli* assay: white pellet |
| 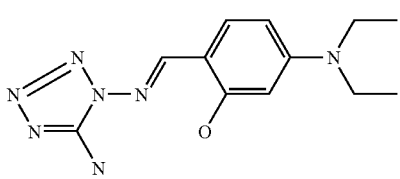 [SMILES: CCN(CC)c1ccc(/C=N/n2nnnc2N)c(O)c1]<br>149; 8010-3066; 275; 5.00; 2.0; 1.17 | Alias: CD-15<br>fluorescence binding: yes<br>minimum inhibition conc: nd<br>NMR sat. transfer: do not bind paHO |

TABLE 2-continued

| Compound | Comments |
|---|---|
| 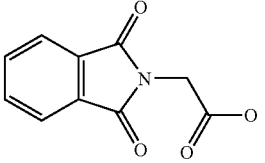 [SMILES: O=C(O)CN1C(=O)c2ccccc2C1=O]150; 0139-0251; 205; 4.00; 2.0; 0.58 | Alias: CD-2<br>fluorescence binding: yes<br>minimum inhibition conc: no antibacterial activity<br>NMR sat. transfer: yes, bind paHO |
| 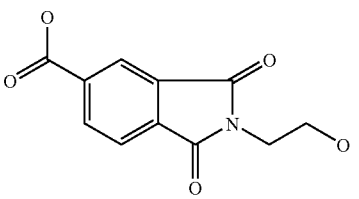 [SMILES: O=C(O)c1ccc2c(c1)C(=O)N(CCO)C2=O]151; 523381; 235; 5.00; 3.0; 0.09 | Alias: CB-8<br>fluorescence binding: nd<br>minimum inhibition conc: nd<br>NMR sat. transfer: binds paHO |
| 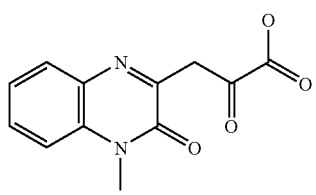 [SMILES: Cn1c(=O)c(CC(=O)C(=O)O)nc2ccccc21]152; AB-323/13887454; 246; 5.00 2.0 −0.29 | Alias: Spec-5 (or SpecD)<br>fluorescence binding: nd<br>minimum inhibition conc: no antibacterial activity<br>NMR sat. transfer: yes, bind paHO |
| 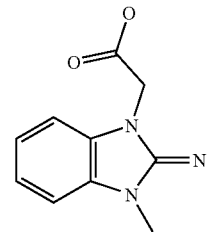153; 2226-0401; 205; 3.00; 3.0; 1.60 | Alias: CD-9<br>fluorescence binding: nd<br>minimum inhibition conc: nd<br>NMR sat. transfer: do not bind paHO | nd—not determined.

The following are some example embodiments of the present invention.

Embodiment 1

A method for treating microbial infection in a subject in need thereof comprising administering to said subject a therapeutically effective amount of an inhibitor of bacterial heme oxygenase.

Embodiment 2

The method for treating microbial infection of Embodiment 1, wherein said microbial infection is at least one infection selected from the group consisting of fungal, viral, protist and bacterial.

Embodiment 3

The method for treating microbial infection of Embodiment 1, wherein said subject is an animal.

Embodiment 4

The method for treating microbial infection of Embodiment 1, wherein said subject is a human.

Embodiment 5

The method for treating microbial infection of Embodiment 1, wherein said inhibitor inhibits at least one of pa-HO and nm-HO.

Embodiment 6

The method for treating microbial infection of Embodiment 1, wherein said inhibitor inhibits nm-HO.

Embodiment 7

The method for treating microbial infection of Embodiment 1, wherein said inhibitor inhibits pa-HO.

Embodiment 8

The method for treating microbial infection of Embodiment 1, wherein said inhibitor inhibits pa-HO and nm-HO.

Embodiment 9

The method for treating microbial infection of Embodiment 1, wherein said inhibitor is more specific against bacterial HO than against mammalian HO.

Embodiment 10

The method for treating microbial infection of Embodiment 1, wherein said inhibitor disrupts at least one pathway selected from the group consisting of:
(i) heme transfer from PhuS to pa-HO;
(ii) heme attachment to PhuS; and
(iii) heme attachment to pa-HO.

Embodiment 11

A method for treating an infection in a patient in need thereof comprising administering to said patient a therapeutically effective amount of at least one compound selected from the group consisting of compounds of General Formulae I-XIII.

Embodiment 12

A method for treating an infection in a patient in need thereof comprising administering to said patient a therapeutically effective amount of at least one compound selected from the group consisting of Compounds 1-153 and derivatives thereof.

Embodiment 13

The method for treating an infection of Embodiment 12, wherein said infection is at least one infection selected from the group consisting of fungal, viral, protist and bacterial.

Embodiment 14

The method for treating an infection of Embodiment 13, wherein said inhibitor is at least one selected from the group consisting of Compounds 1, 13, 22, 24, 75, 114, 126, and 148 [compounds 1-8 of FIG. 2] and derivatives thereof.

Embodiment 15

The method for treating an infection of Embodiment 14, wherein said inhibitor is at least one selected from the group consisting of Compounds 1, 75 and 126 [Compounds 2, 3 or 5 of FIG. 2] and derivatives thereof.

Embodiment 16

The method for treating an infection of Embodiment 1 or 12, wherein said bacterial infection is an antibiotic-resistant organism.

Embodiment 17

The method for treating an infection of Embodiment 1 or 12, wherein said infection is due to *Pseudomonas aeruginosa, N. meninigitidis, C. diphtheriae, Haemophilus influenzae* and/or *Porphyromonas gingivalis*.

Embodiment 18

The method for treating an infection of Embodiment 1 or 12, wherein said infection is due to *Pseudomonas aeruginosa* and/or *N. meninigitidis*.

Embodiment 19

The method for treating an infection of Embodiment 1 or 12, wherein said patient has cystic fibrosis.

Embodiment 20

The method for treating an infection of Embodiment 1 or 12, wherein said at least one compound is administered to treat microbial infection in a lung.

Embodiment 21

The method for treating an infection of Embodiment 1 or 12, comprising administering said at least one compound is administered to the lung cavity.

Embodiment 22

A method of decreasing an amount of an undesired organism comprising contacting a cell of the undesired organism with an inhibitor of microbial heme oxygenase having a structure of General Formulae I-XIII, wherein the compound inhibits heme oxygenase thereby decreasing the amount of the undesired organism.

Embodiment 23

The method of decreasing an amount of an undesired organism of Embodiment 22, wherein the contacting occurs in vivo, in situ, ex vivo, or in vitro.

Embodiment 24

A pharmaceutical composition comprising a therapeutically effective amount of an inhibitor of microbial heme oxygenase having a molecular weight of less than 500 Da, and a pharmaceutically acceptable carrier, diluent or excipient.

Embodiment 25

The pharmaceutical composition as claimed in Embodiment 24, wherein said inhibitor of microbial heme oxygenase is an inhibitor of bacterial-HO.

Embodiment 26

The pharmaceutical composition as claimed in Embodiment 24, wherein said inhibitor of microbial heme oxygenase is an inhibitor of nm-HO or pa-HO.

Embodiment 27

A pharmaceutical composition comprising a therapeutically effective amount of an inhibitor of non-mammalian heme oxygenase having a molecular weight of less than 500 Da, and a pharmaceutically acceptable carrier, diluent or excipient.

Embodiment 28

A pharmaceutical composition comprising a therapeutically effective amount of an inhibitor of heme oxygenase having a molecular weight of less than 500 Da, and a pharmaceutically acceptable carrier, diluent or excipient.

Embodiment 29

The pharmaceutical composition as claimed in Embodiment 24, wherein said inhibitor of microbial heme oxygenase is an inhibitor of fungal, viral, protist and/or bacterial heme oxygenase.

Embodiment 30

A pharmaceutical composition comprising a therapeutically effective amount of at least one inhibitor of microbial heme oxygenase compound selected from the group consisting of compounds of General Formulae I-XIII.

Embodiment 31

A pharmaceutical composition comprising a therapeutically effective amount of at least one inhibitor of microbial heme oxygenase compound selected from the group consisting of Compounds 1-153, and a pharmaceutically acceptable carrier, diluent or excipient.

Embodiment 32

The pharmaceutical composition as claimed in Embodiment 31, wherein said compound is at least one selected from the group consisting of Compounds 1, 13, 22, 24, 75, 114, 126, and 148 [compounds 1-8 of FIG. 2].

Embodiment 33

The pharmaceutical composition as claimed in Embodiment 31, said compound is at least one selected from the group consisting of Compounds 1, 75 and 126. [Compounds 2, 3 or 5 of FIG. 2.]

Embodiment 34

The pharmaceutical composition as claimed in Embodiment 31, further comprising an antibiotic agent.

Embodiment 35

A method for screening compounds for ability to bind to a heme pocket of a microbial-HO comprising:

obtaining at least one conformation of a heme binding pocket in an apo form of the microbial-HO via a molecular dynamics (MD) simulation of the apo protein from the crystal structure of the microbial-HO;

selecting at least one of said at least one conformation for database screening calculations from a plot of the His-23 to Gly-116 distance as a function of time;

screening a database of compounds with a single conformation of at least one of said at least one conformation; and selecting compounds based on the N normalized van der Waals attraction interaction energy.

Embodiment 36

The method for screening compounds of Embodiment 35, wherein said single conformation is at 5,575 ps.

Embodiment 37

The method for screening compounds of Embodiment 35, further comprising subjecting said selected compounds to a secondary screen with multiple conformations.

Embodiment 38

The method for screening compounds of Embodiment 37, wherein said multiple conformations are four protein conformations at 5,575, 16,455, 16,805, and 19965 ps.

Embodiment 39

The method for screening compounds of Embodiment 35, further comprising grouping said compound from said secondary screen based on chemical fingerprints into one or more clusters of compounds that have chemical diversity.

Embodiment 40

The method for screening compounds of Embodiment 39, further comprising selecting one or two compounds from each cluster for testing with at least one biological assay.

Embodiment 41

The method for screening compounds of Embodiment 40, wherein said one or two compounds from each cluster are selected following Lipinski's rule of 5.

Embodiment 42

The method for screening compounds of Embodiment 40, further comprising testing for solubility in buffer or DMSO.

Embodiment 43

The method for screening compounds of Embodiment 40, further comprising testing said one or two compounds from each cluster to in vitro testing for ability to bind to said microbial-HO.

Embodiment 44

The method for screening compounds of Embodiment 40, further comprising testing said one or two compounds from each cluster to in vivo testing for ability to inhibit said microbial-HO.

Embodiment 45

The method for screening compounds of Embodiment 40, further comprising testing said one or two compounds from each cluster to in vitro testing for binding affinity to said microbial-HO and testing said one or two compounds from each cluster to in vivo testing for ability to inhibit said microbial-HO.

Embodiment 46

The method for screening compounds of Embodiment 41, comprising testing for binding affinity and ability to inhibit enzymatic activity of both nm-HO and pa-HO.

Embodiment 47

The method for screening compounds of Embodiment 39, wherein said in vitro testing for the ability to bind to said microbial-HO comprises testing of fluorescence quenching of the microbial-HO protein.

Embodiment 48

The method for screening compounds of Embodiment 47, wherein said in vitro testing for the ability to bind to said microbial-HO comprises testing the ability to inhibit the production of α-biliverdin in *E. coli* cells expressing said microbial-HO.

Embodiment 49

The method for screening compounds of Embodiment 44, wherein said in vivo testing for ability to inhibit said microbial-HO comprises testing for ability to inhibit the growth of MPA01 when given heme as the sole source of iron.

Embodiment 50

The method for screening compounds of Embodiment 45, further comprising testing additional compounds of a cluster based on results of said one or two compounds of a cluster.

We claim:

1. A method for treating a bacterial infection in a patient in need thereof comprising administering to said patient a therapeutically effective amount of at Compound 75:

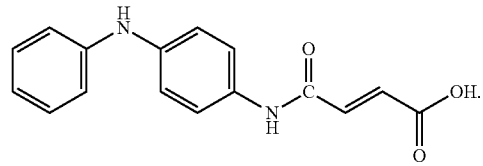

Compound 75

2. The method for treating the bacterial infection of claim 1, wherein said bacterial infection is an antibiotic-resistant organism.

3. The method for treating the bacterial infection of claim 1, wherein said bacterial infection is due to one or more bacteria selected from the group consisting of *Pseudomonas aeruginosa, N. meninigitidis, C. diphtheriae, Haemophilus influenzae* and *Porphyromonas gingivalis*.

4. The method for treating the bacterial infection of claim 1, wherein said bacterial infection is due to one or more bacteria selected from the group consisting of *Pseudomonas aeruginosa* and *N. meninigitidis*.

5. The method for treating the bacterial infection of claim 1, wherein said bacterial infection is a microbial infection in a lung.

* * * * *

UNITED STATES PATENT AND TRADEMARK OFFICE
CERTIFICATE OF CORRECTION

PATENT NO. : 8,450,368 B2  
APPLICATION NO. : 12/374964  
DATED : May 28, 2013  
INVENTOR(S) : Angela Wilks et al.

Page 1 of 1

It is certified that error appears in the above-identified patent and that said Letters Patent is hereby corrected as shown below:

In the Specification

In Column 1, lines 11-14, the statement regarding federally sponsored research or development

This invention was made with the support of the U.S. government under Grant Number AI055912 from the National Institute of Health (NIH). The U.S. government has certain rights in this invention.

Should read

This invention was made with government support under Grant Number AI055912 awarded by the National Institutes of Health. The government has certain rights in the invention.

Signed and Sealed this  
Third Day of September, 2013

Teresa Stanek Rea  
*Acting Director of the United States Patent and Trademark Office*